(12) United States Patent
Lee et al.

(10) Patent No.: US 12,037,529 B2
(45) Date of Patent: Jul. 16, 2024

(54) LUMINESCENT LAYERED COMPOSITION AND A METHOD FOR USING THE COMPOSITION

(71) Applicant: Rutgers, the State University of New Jersey, New Brunswick, NJ (US)

(72) Inventors: Ki-Bum Lee, Piscataway, NJ (US); Hudifah Rabie, Piscataway, NJ (US); Nicholas Pasquale, Piscataway, NJ (US); Yixiao Zhang, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 826 days.

(21) Appl. No.: 17/137,813

(22) Filed: Dec. 30, 2020

(65) Prior Publication Data
US 2021/0139772 A1    May 13, 2021

Related U.S. Application Data

(63) Continuation of application No. PCT/US2019/040387, filed on Jul. 2, 2019.
(Continued)

(51) Int. Cl.
*C09K 11/08* (2006.01)
*A61K 31/203* (2006.01)
(Continued)

(52) U.S. Cl.
CPC ........ *C09K 11/0833* (2013.01); *A61K 31/203* (2013.01); *A61K 49/0013* (2013.01);
(Continued)

(58) Field of Classification Search
CPC .. A61K 31/203; A61K 49/0013; C09K 11/02; C12N 5/0696; C12N 15/115; B82Y 5/00; B82Y 40/00
(Continued)

(56) References Cited

U.S. PATENT DOCUMENTS

| 6,363,090 B1 | 3/2002 | Pierschbacher et al. |
| 10,295,467 B2 | 5/2019 | Han et al. |

(Continued)

FOREIGN PATENT DOCUMENTS

| WO | WO 2010/014236 | 2/2010 |
| WO | WO 2020/010133 | 1/2020 |

OTHER PUBLICATIONS

Ding et al., "Highly enhanced upconversion luminescence in lanthanide-doped active-core/luminescent-shell/active-shell nanoarchitectures," *Journal of Materials Chemistry C* 4(13):2432-2437, 2016.
(Continued)

*Primary Examiner* — Anita Nassiri-Motlagh
(74) *Attorney, Agent, or Firm* — Klarquist Sparkman, LLP

(57) ABSTRACT

Disclosed herein are embodiments of a composition comprising at least three layers. Layers one and two each either comprises a sensitizer or an emitter, typically a metal ion or a dye, and the third layer may or may not comprise a sensitizer or emitter. Upon exposure to light, such as infrared light, the composition produces visible and/or UV light. The composition may further comprise a capping moiety, a therapeutic agent, an uptake enhancer, a detection moiety that binds to a desired target, a quenching moiety, or a combination thereof. The composition may be a particle, such as a nanoparticle, or it may be a planar composition. Also disclosed are embodiments of a method for using the composition, including, but not limited to, a method for delivering a therapeutic agent, or a method for detecting a target, such as a biological target.

20 Claims, 25 Drawing Sheets
Specification includes a Sequence Listing.

Related U.S. Application Data

(60) Provisional application No. 62/693,853, filed on Jul. 3, 2018.

(51) Int. Cl.
  *A61K 49/00* (2006.01)
  *B82Y 5/00* (2011.01)
  *B82Y 40/00* (2011.01)
  *C09K 11/02* (2006.01)
  *C12N 5/074* (2010.01)
  *C12N 15/115* (2010.01)

(52) U.S. Cl.
  CPC ............ *C09K 11/02* (2013.01); *C12N 5/0696* (2013.01); *C12N 15/115* (2013.01); *B82Y 5/00* (2013.01); *B82Y 40/00* (2013.01); *C12N 2310/16* (2013.01); *C12N 2500/05* (2013.01); *C12N 2506/03* (2013.01); *C12N 2529/10* (2013.01)

(58) Field of Classification Search
  USPC .................................................. 252/301.4 H
  See application file for complete search history.

(56) References Cited

U.S. PATENT DOCUMENTS

| | | |
|---|---|---|
| 2004/0002089 A1 | 1/2004 | Dubertret et al. |
| 2007/0258926 A1 | 11/2007 | Yamaguchi et al. |
| 2008/0213377 A1 | 9/2008 | Bhatia et al. |
| 2012/0040282 A1 | 2/2012 | Heuft et al. |
| 2012/0270221 A1 | 10/2012 | Bruno et al. |
| 2013/0040305 A1 | 2/2013 | Kiel et al. |
| 2015/0086479 A1 | 3/2015 | Barbe et al. |
| 2015/0353821 A1 | 12/2015 | Zhang et al. |
| 2016/0122635 A1 | 5/2016 | Liu et al. |

OTHER PUBLICATIONS

International Search Report and Written Opinion dated Oct. 1, 2019 from International Application No. PCT/US2019/040387.

Rabie et al., "Energy Back-Transfer Mitigation Using Core-Shell Architecture for Enhanced Upconversion Efficiency," I2018 MRS Spring Meeting& Exhibition, 1 page, Apr. 2-6, 2018, Phoenix, AZ.

Wang et al., "Giant enhancement of upconversion emission in $NaYF_4:Er^{3+}@NaYF_4:Yb^{3+}$ active-core/active-shell nanoparticles," *RSC Advances* 24:22845-22851, 2016 (Abstract Only).

Ye et al., "Tuning upconversion through a sensitizer/activator-isolated $NaYF_4$ core/shell structure," *Nanoscale* 7:3976-3985, 2015.

Zhang et al., "Remote Control of Neural Stem Cell Fate Using NIR-Responsive Photoswitching Upconversion Nanoparticle Constructs," *ACS Applied Materials & Interfaces* 12(36):40031-40041, Sep. 2020 (Abstract Only).

Zuo et al., "Precisely Tailoring Upconversion Dynamics via Energy Migration in Core-Shell Nanostructures," *Angewandte Chemie International Edition* 57(12):3054-3058, 2018.

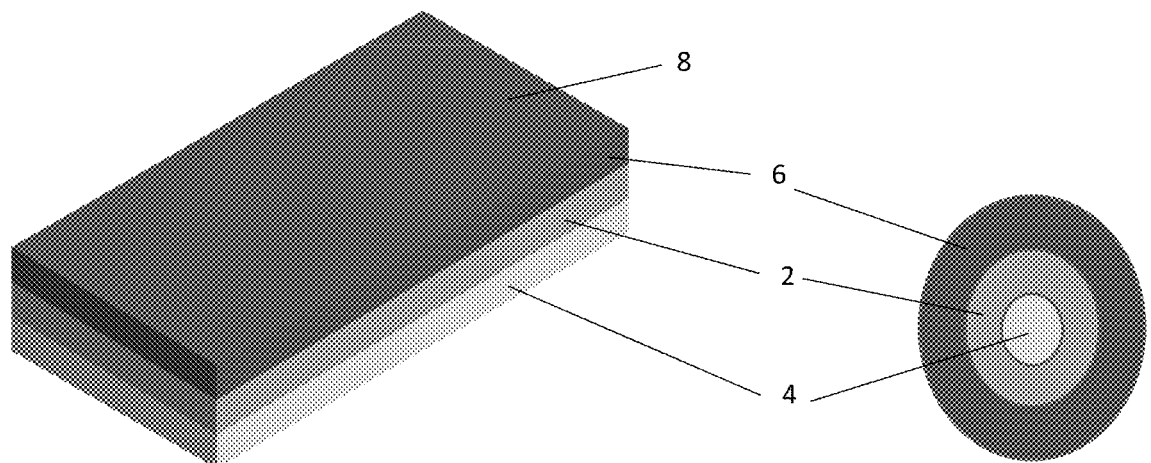
FIG. 3A
FIG. 3B
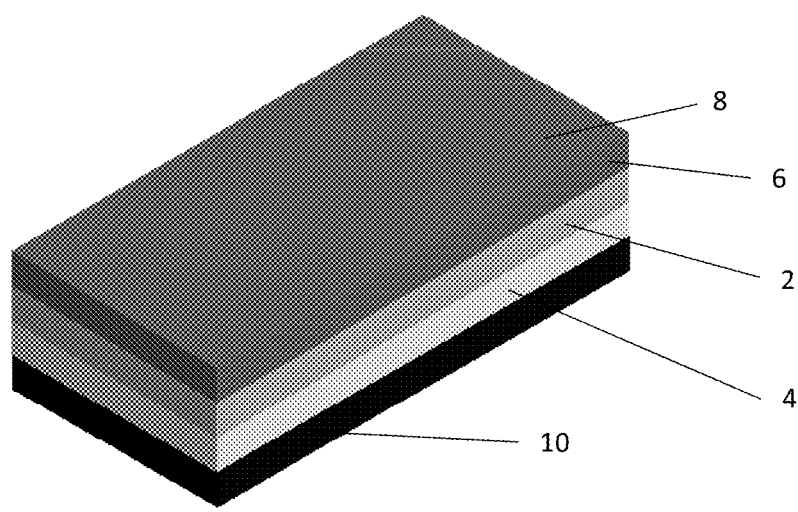
FIG. 4

| | 366 nm [μs] | 420 nm [μs] | 475 nm [μs] | 543 nm [μs] | 660 nm [μs] | 800 nm [μs] |
|---|---|---|---|---|---|---|
| NaYF$_4$(0.3%Tm,30%Yb)@NaYF$_4$(30%Yb) | 314 ± 14 | - | 541 ± 3 | - | - | 763 ± 6 |
| NaYF$_4$(2%Er, 20%Yb)@NaYF$_4$(20%Yb) | - | 210 ± 8 | - | 228 ± 14 | 345 ± 3 | - |
| NaYF$_4$(30%Yb)@NaYF$_4$(1.5%Tm)@NaYF$_4$(30%Yb) | 413 ± 22 | - | 517 ± 2 | - | - | 1017 ± 2 |
| NaYF$_4$(20%Yb)@NaYF$_4$(2%Er)@ NaYF$_4$(20%Yb) | | 642 ± 20 | | 904 ± 5 | 979 ± 7 | |

FIG. 19

LUMINESCENT LAYERED COMPOSITION AND A METHOD FOR USING THE COMPOSITION

CROSS REFERENCE TO RELATED APPLICATIONS

This is a continuation of International Application No. PCT/US2019/040387, filed Jul. 2, 2019, which was published in English under PCT Article 21(2), which in turn claims the benefit of the earlier filing date of U.S. provisional patent application No. 62/693,853, filed Jul. 3, 2018, both of which are incorporated herein by reference in their entireties.

ACKNOWLEDGMENT OF GOVERNMENT SUPPORT

This invention was made with government support under the Director's Innovator Award No. 1DP20D006462-01 awarded by National Institutes for Health, and under grant No. CHE-1429062 awarded by the National Science Foundation. The government has certain rights in the invention.

FIELD

Certain disclosed embodiments concern a composition comprising at least three layers, at least two of which separately comprise either a sensitizer moiety or an emitter moiety, and a method for using the composition.

BACKGROUND

Lanthanide-doped upconversion nanoparticles (UCNPs) are a unique class of inorganic phosphors capable of absorbing near-infrared (NIR) excitations and converting it, through the sequential absorption of NIR photons, to ultraviolet (UV) and/or visible emissions. Coupled with their high photostability, weak background auto-fluorescence, and the ability of NIR excitation to deeply penetrate biological tissues, UCNPs are advancing the fields of sub-cellular labeling, in vivo bio-imaging, bio-sensing and optogenetics. However, despite their enormous potential, co-doped $NaYF_4$:Yb/Ln (where Ln is a lanthanide activator) (FIG. 1), exhibits relatively poor upconversion efficiencies, especially in response to low-intensity laser excitations. This is due to several major factors including: i) the low absorption cross-section of $Yb^{3+}$, which sensitizes the UCNPs to the absorption of 980 nm NIR light; ii) the parity forbidden nature of the 4f-4f transitions of the lanthanides; and iii) the use of relatively low concentrations of luminescent lanthanides to prevent quenching. As such, UCNPs are typically irradiated with relatively high-power density excitations, exceeding safe thresholds for biological applications due to significant heating caused by 980 nm NIR excitation in aqueous systems.

There have been many attempts to overcome the efficiency limitations and advance UCNP-based biomedical technologies, including: host material selections, crystal field tuning, dopant selection and concentration tuning, and the mitigation of surface-related deactivations. However, these methods all remain unsuitable for use as biosensors. Another method for increasing upconversion nanoparticle efficiency involves the utilization of core@shell architectures. A representative example of such an architecture would be the use of a sensitizing $Yb^{3+}$ doped "active shell" $NaYF_4$ shell (FIG. 2). This method uses a $Yb^{3+}$-doped shell around a Yb/Ln-doped core, where Ln is a lanthanide activator. This method increases the absorption of 980 nm NIR excitation by supplying the activator with more photon flow resulting from an expansion of the $Yb^{3+}$ sub-lattice, without increasing $Yb^{3+}$ concentration in the UCNP which would be severely detrimental due to $Yb^{3+}$—$Yb^{3+}$ cross-relaxation; however, this approach still requires relatively high-power laser excitation, and therefore heating effect. Additionally, in both the co-doped core and "active shell" examples, lanthanide-$Yb^{3+}$ energy back-transfer is major deleterious pathway. This back transfer has a profound impact on the spectral profile, causing red emissions to occur at the expense of the more desirable higher order green emissions, and thereby decreasing the overall luminescent intensity.

SUMMARY

Disclosed herein are embodiments of a composition that mitigates energy back transfer thereby allowing brighter visible and/or UV light responses that result from lower light excitation. This can enable the disclosed composition to be used in therapeutic delivery, bio-imaging, sub-cellular labeling and/or sensing without the risk of inducing thermal toxicity, as is often the case for existing technologies. Additionally, certain disclosed embodiments absorb 808 nm light, that produces significantly less, if any, heating in aqueous systems, compared to 980 nm light, and also penetrates biological tissue to a greater depth.

In some embodiments, the composition comprises a first layer comprising a first substrate and a first dopant, a second layer in direct physical contact with the first layer, the second layer comprising a second substrate and a second dopant, and a third layer in direct physical contact with the second layer and not in direct physical contact with the first layer, the third layer comprising a third substrate and optionally a third dopant. Each of the first, second and third dopants independently may be a lanthanide ion, an NIR emitting dye, or a combination thereof, and the second dopant may be different from the first and third dopants, if present, and/or each dopant may be different. Each of the first, second and third substrates may be selected from $NaYF_4$, $CaF_2$, $ZrO_2$, $YVO_4$, $Y_2O_2S$, GdOCl, GdOF, $Y_2O_3$, $NaPrF_4$, $NaPmF_4$, $NaSmF_4$, $NaEuF_4$, $NaGdF_4$, $NaTbF_4$, $NaDyF_4$, $NaHoF_4$, $NaTmF_4$, $NaErF_4$, $NaCeF_4$, $NaNdF_4$, $NaLuF_4$, $NaYbF_4$, or a combination thereof.

In some examples, the first dopant is an emitter dopant and the second dopant is a sensitizer dopant. In such embodiments, the third layer may or may not comprise the third dopant. In alternative embodiments, the first dopant is a sensitizer dopant, the second dopant is an emitter dopant, and the third layer may or may not comprise the third dopant. In other embodiments, the first dopant and the third dopant are sensitizer dopants, and the second dopant is an emitter dopant. The sensitizer dopant(s) may be selected to absorb light having a wavelength of from 600 nm to 1300 nm, and in particular embodiments, the light may comprise light having a wavelength of 980 nm and/or 808 nm. Additionally, or alternatively, the emitter dopant may be selected to emit light having a wavelength of from 300 nm to 560 nm or more, such as from 330 nm to 560 nm. In certain embodiments, the emitter dopant may be selected to emit light having a wavelength of from 340 nm to 375 nm, from 425 nm to 480 nm and/or from 500 nm to 560 nm. In certain disclosed embodiments, the emitted light has one or more wavelengths selected from 347 nm, 360 nm, 450 nm, 474 nm, 540 nm, or a combination thereof. In some embodiments, each of the sensitizer dopants independently is or comprises a ytterbium ion, neodymium ion, an NIR emitting dye, or a combination thereof, and may be a ytterbium ion or ytterbium ion/neodymium ion combination. In embodiments comprising more than one sensitizer dopants, the dopants may be the same dopant or different dopants. In certain embodiments, the first and third dopants both comprise, consist essentially of, or consist of $Yb^{3+}$. And in other embodiments, the sensitizer dopant comprises, consists essentially of, or consists of, $Yb^{3+}$ and $Nd^{3+}$.

The emitter dopant may be a praseodymium ion, promethium ion, samarium ion, europium ion, terbium ion, dysprosium ion, holmium ion, erbium ion, thulium ion, ytterbium ion, or a combination thereof, and in certain embodiments, the emitter dopant comprises, consists essentially of, or consists of $Er^{3+}$. In alternative embodiments, the emitter dopant comprises, consists essentially of, or consists of $Yb^{3+}$ and $Tm^{3+}$. The first layer may comprise from greater than zero to 50 mol % of the first dopant, such as from 20 mol % to 30 mol %. Additionally, or alternatively, the second layer may comprise from greater than zero to 50 mol % of the second dopant, such as from 0.1 mol % to 30 mol %. In some embodiments, the second layer comprises from greater than zero to 5 mol % of the second dopant, such as from 0.1 mol % to 4 mol %, but in alternative examples, the second layer comprises from 10 mol % to 30 mol % of the second dopant, such as from 15 mol % to 25 mol %. In any embodiments, the third layer may comprise from zero to 50 mol % of the third dopant, such as zero mol % or from greater than zero to 50 mol %, or from 20 mol % to 30 mol %.

In some embodiments, the composition is a particle. In such embodiments, the particle's first layer is a particle core, the second layer is an inner layer at least partially coating the core, and the third layer is an outer layer at least partially coating the inner layer. The particle may be a nanoparticle and/or may have a core having at least one dimension of from 5 to 50 nm, such as from 10 nm to 50 nm.

In other embodiments, the composition is a planar composition, and may comprise a fourth substrate, such as a base or support substrate, in direct physical contact with the first layer. The fourth substrate may be optically transparent. In some embodiments, the fourth substrate may be silica; a transparent conductive oxide, such as indium tin oxide or zinc aluminum oxide; a photocatalytic substrate, such as titanium oxide; $NaYF_4$; $CaF_2$; $ZrO_2$; $YVO_4$; $Y_2O_2S$; $GdOCl$; $GdOF$; $Y_2O_3$; $NaPrF_4$; $NaPmF_4$; $NaSmF_4$; $NaEuF_4$; $NaGdF_4$; $NaTbF_4$; $NaDyF_4$; $NaHoF_4$; $NaTmF_4$; $NaErF_4$; $NaCeF_4$; $NaNdF_4$; $NaLuF_4$; $NaYbF_4$; or a combination thereof.

In any embodiments, the first layer may have a thickness of from 5 to 50 nm, such as from 10 to 50 nm. The second layer may have a thickness of from greater than zero to 20 nm, such as from 5 to 10 nm. And/or the third layer may have a thickness of from 5 nm to 50 nm. In some examples, a particle composed of three layers has a thickness (e.g., diameter if spherical) of at least 15 nm, at least 20 nm, or at least 25 nm, such as from 15 nm to 100 nm or more, or from 20 nm to 100 nm.

In a particular embodiment, the first layer comprises $NaYF_4$ doped with 25 mol % $Yb^{3+}$ and 0.3 mol % $Tm^{3+}$, the second layer comprises $NaYF_4$ doped with 10 mol % $Yb^{3+}$ and 10 mol % $Nd^{3+}$, and the third layer comprises $NaYF_4$ without a dopant. In another embodiment, the first layer and the third layer each comprise $NaYF_4$ doped with 20 mol % $Yb^{3+}$, and the second layer comprises $NaYF_4$ doped with 2 mol % $Er^{3+}$.

The composition may further comprise a fourth layer in direct physical contact with the third layer. The fourth layer may comprise silica, an amphiphilic polymer, $NaYF_4$, $CaF_2$, $ZrO_2$, $YVO_4$, $Y_2O_2S$, $GdOCl$, $GdOF$, $Y_2O_3$, $NaPrF_4$, $NaPmF_4$, $NaSmF_4$, $NaEuF_4$, $NaGdF_4$, $NaTbF_4$, $NaDyF_4$, $NaHoF_4$, $NaTmF_4$, $NaErF_4$, $NaCeF_4$, $NaNdF_4$, $NaLuF_4$, $NaYbF_4$, or any combination thereof, and may be doped or undoped. In some embodiments, the fourth layer comprises silica and may be a non-porous or porous layer, such as a mesoporous silica layer.

The composition may further comprise a capping moiety attached and/or conjugated to the fourth layer. The capping moiety may comprise an azo derivative, heteroaryl azo derivative, diarylethene, imines derivative, acylhydrazone, hydrazone, hemithioindigo derivative, donor-acceptor Stenhouse adduct, or a combination thereof, and in certain examples, the capping moiety comprises

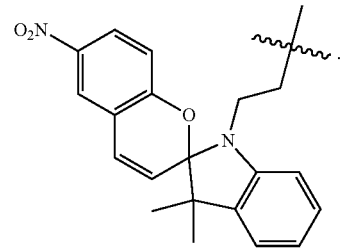 [SMILES: *CCN1c2ccccc2C(C)(C)C12C=Cc1cc([N+](=O)[O-])ccc1O2]

The composition may comprise a therapeutic agent, such as a differentiation factor, chemotherapeutic agent, anti-inflammatory agent, antibiotic, antiviral, anesthetic agent, antipyretic, antiseptic, hormone, stimulant, depressant, statin, beta blocker, anticoagulant, anti-fungal, growth factor, vaccine, diagnostic composition, psychiatric medication, psychoactive compound, or a combination thereof. In certain embodiments, the therapeutic agent is or comprises retinoic acid. And/or the composition may comprise an uptake enhancer. The uptake enhancer may be a peptide, such as Arg-Gly-Asp.

Additionally, or alternatively, the composition may comprise a detection moiety, such as an oligonucleotide, a polypeptide, antibody, antigen, or a combination thereof. The oligonucleotide may be an aptamer, such as a dopamine aptamer. The detection moiety may be conjugated to the fourth layer, if present.

The composition may further comprise a quenching moiety. The quenching moiety may be selected to absorb at least a portion of light emitted from the second layer. The quenching moiety may comprise graphene and may be graphene oxide. In some embodiments, the quenching moiety is adsorbed onto the detection layer.

Also disclosed are embodiments of a mixed composition comprising two or more of the disclosed layered compositions. Such a mixed composition may comprise a first composition as disclosed herein having a first detection moiety, and a second composition as disclosed herein having a second detection moiety that is different from the first detection moiety. The first detection moiety may detect a first target and the second detection moiety may detect a second target that is different from the first target.

Also disclosed are embodiments of a method of using the disclosed composition. The method may comprise exposing the disclosed composition to incident light having a wavelength of from 600 nm to 1300 nm. The incident light may be near infrared (NIR) light. The method may further comprise administering the composition to a subject prior to exposing the composition to the incident light. And in embodiments where the composition comprises a capping moiety and a therapeutic agent, administering the composition may comprise administering the composition to a subject in need of the therapeutic agent.

The method may comprise detecting the presence or absence of emitted light from the composition upon exposure of the composition to the incident light. The emitted light, if present, may comprise visible light, UV light, or both, and/or may comprise light having a wavelength of from 500 nm to 560 nm. In embodiments where the composition comprises a detection moiety, the method may comprise exposing a sample suspected of containing a target recognizable by the detection moiety to the composition prior to exposing the composition to the incident light, and determining the presence or absence of the target based on the presence or absence of emitted light. The sample may be a biological sample, such as a tissue sample or a bodily fluid sample, and/or may comprise saliva, blood, urine, plasma, cerebrospinal fluid, amniotic fluid, pleural fluid, muscle tissue, fat, brain cells, bone marrow, cancer cells, antibodies, or a combination thereof.

In some embodiments, administering the composition to a subject may comprise administering the composition to a particular site on the subject's body that is suspected of continuing a target recognizable by the detection moiety and determining the presence or absence of the target based on the presence or absence of the emitted light.

In any embodiments, the target may be a DNA strand, an RNA strand, a polypeptide, a signaling molecule, a hormone, a steroid, a lipid, a phospholipid, an amino acid, a nucleic acid, antibody, antigen, vitamin, recreational drug, medicinal drug, poison, virus, cancer marker, or a combination thereof.

Further disclosed is a method for detecting dopamine. The method comprises contacting a sample suspected of containing dopamine with a nanoparticle comprising a particle core comprising $NaYF_4$ and $Yb^{3+}$, a first layer substantially coating the particle core and comprising $NaYF_4$ and $Er^{3+}$, a second layer substantially coating the first layer and comprising $NaYF_4$ and $Yb^{3+}$, a silica layer substantially coating the second layer, a dopamine aptamer attached to the silica layer, and graphene oxide sheets adsorbed onto the dopamine aptamer. The method further comprises exposing the nanoparticle to incident light comprising light having a wavelength of 980 nm and determining the presence or absence of dopamine in the sample, by detecting for the presence of emitted light having a wavelength of 540 nm.

The foregoing and other objects and features of the disclosure will become more apparent from the following detailed description, which proceeds with reference to the accompanying figures.

BRIEF DESCRIPTION OF THE DRAWINGS

FIGS. 3A-3B are schematic diagrams showing two exemplary configurations of an embodiment of the disclosed technology. FIG. 3A illustrates a planar configuration, and FIG. 3B illustrates a particle configuration.

FIG. 4 is a schematic diagram illustrating the planar configuration including a fourth substrate in contact with the first layer.

FIG. 5A illustrates a planar configuration, and FIG. 5B illustrates a particle configuration.

FIG. 19 is a table providing the life-time measurements of exemplary embodiments of the disclosed structure compared with the life-time measurements from "active shell" structures, when excited by a 980 nm (200 mW, CW) laser.

SEQUENCE LISTING

Figure 1:
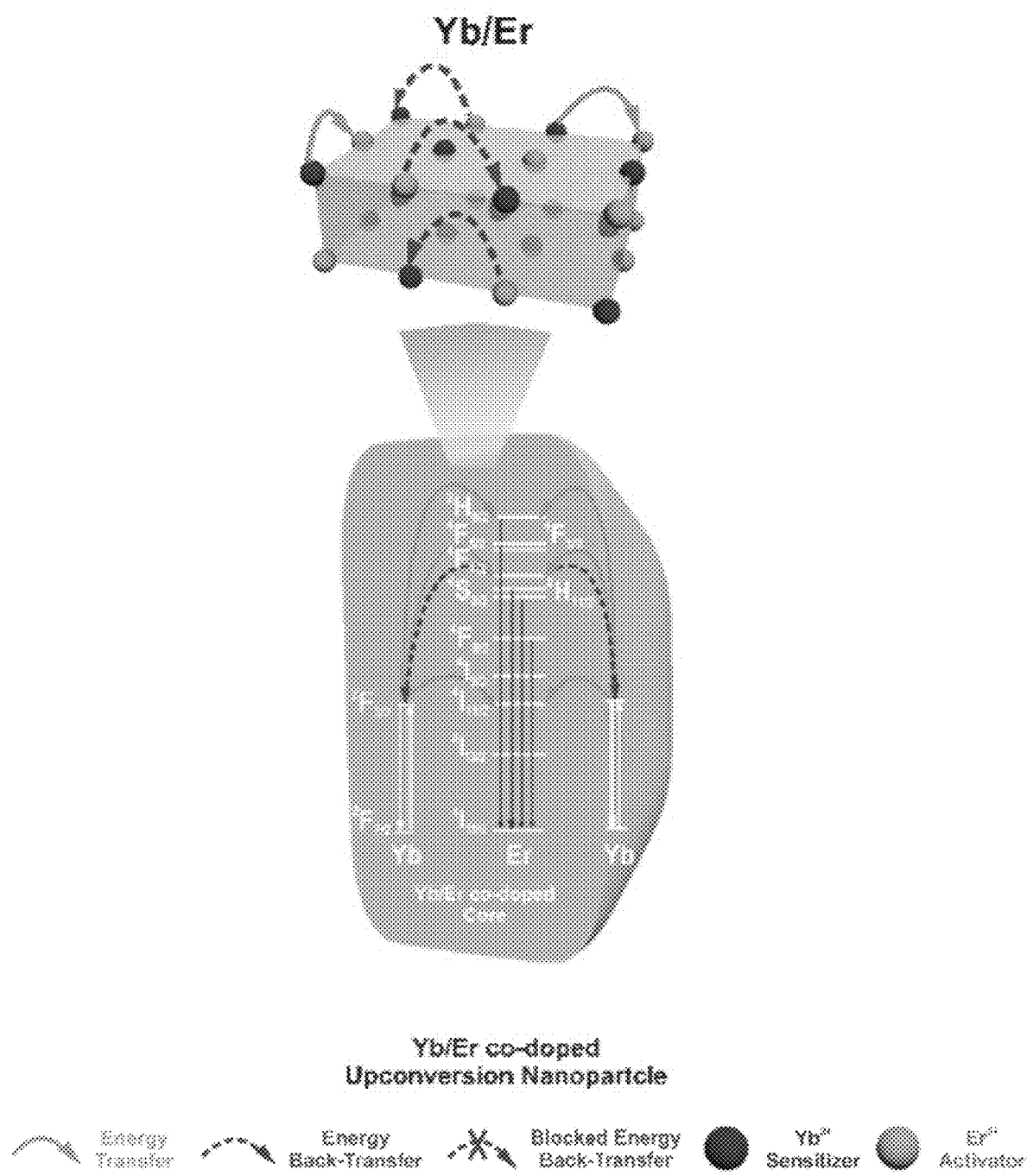
FIG. 1 is a schematic energy level diagram illustrating the energy migration mechanism for a co-doped Yb/Er upconversion nanoparticle (UCNP), and showing that energy back transfer (red/dashed arrows) from $Er^{3+}$ to $Yb^{3+}$ exists throughout the nanoparticle.
Figure 2:
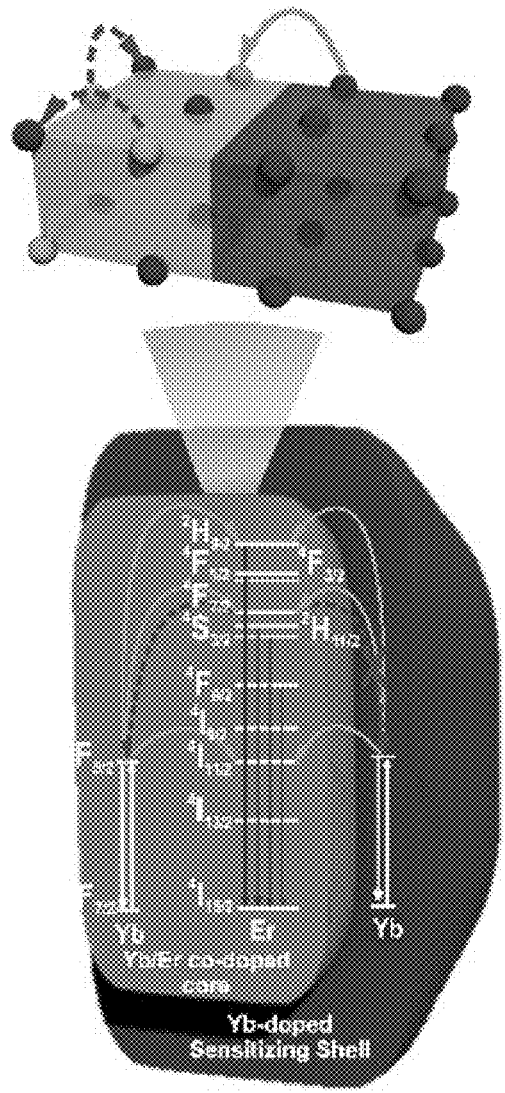
FIG. 2 is a schematic energy level diagram illustrating the energy migration mechanism for an "active shell" Yb/Er@Yb UCNPs and showing that energy back transfer (red/dashed arrows) from $Er^{3+}$ to $Yb^{3+}$ exists majorly in the $Yb^{3+}$ and $Er^{3+}$ co-doped core.

The nucleic and amino acid sequences listed in the accompanying sequence listing are shown using standard letter abbreviations for nucleotide bases, and three letter code for amino acids, as defined in 37 C.F.R. § 1.822. Only one strand of each nucleic acid sequence is shown, but the complementary strand is understood as included by any reference to the displayed strand. The Sequence Listing is submitted as an ASCII text file, created on Dec. 23, 2020, 4 KB, which is incorporated by reference herein.

SEQ ID NO: 1 is a modified aptamer nucleic acid sequence that binds dopamine.

SEQ ID NOS: 2 and 3 are forward and reverse primers, respectively. used to amplify GAPDH.

SEQ ID NOS: 4 and 5 are forward and reverse primers, respectively. used to amplify TUJ1.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/ methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

I. Composition

Disclosed herein is a novel at least 3-layered "sandwich" composition that, in some embodiments, may be a core-shell-shell structured nanoparticle. In some embodiments, the first layer comprises a first substrate and a first dopant, the second layer comprises a second substrate and a second dopant, and the third layer comprises a third substrate and optionally a third dopant. In some embodiments, the first and third dopants are the same or different sensitizer dopants and the second dopant is an emitter dopant. In certain alternative embodiments, the first dopant is an emitter dopant, the second dopant is a sensitizer dopant, and the third layer does not comprise a dopant.

The second layer is located between the first and third layers, such that the second layer is in direct physical contact with both the first and third layers, but typically, the first and third layers are not in direct physical contact with each other. The second layer at least partially covers the first layer, and may substantially cover the first layer. And the third layer at least partially covers the second layer, and may substantially cover the second layer. FIGS. 3A and 3B provides two exemplary configurations of the disclosed composition: a planar structure in FIG. 3A, and a particle structure in FIG. 3B. As shown in FIGS. 3A and 3B, in both the planar configuration and the particle configuration, the second layer 2 is in direct physical contact with both the first layer 4 and the third layer 6, but the first layer 4 and third layer 6 are not in direct physical contact with each other.

Without being bound to a particular theory, this architecture may serve to minimize the probability of energy back-transfer from excited state emitter ions to adjacent sensitizer ions by spatially separating them in different layers to significantly enhance desired two photon emissions, while discouraging the higher three photon energy pathways, from the disclosed composition in response to low power density NIR excitation. The design uses spatial separation as a method of limiting resonant energy transfer (RET) to a two-photon process by making distances long enough so that three-photon processes are significantly decreased, favoring green emissions over blue emissions deleterious back-transfer based red emissions, which also is a three-photon process. This was accomplished by isolating the sensitizers and activators in separate layers, thereby decreasing the number of sensitizer ions that are in close proximity to emitters, and therefore, decreasing the probability of energy back transfer from the emitters to the sensitizers without decreasing the sensitizer ion count. The results demonstrated that the disclosed "sandwich" structure provided significantly more intense, two-photon process emissions than traditional co-doped core structures, such as $\beta$-NaYF$_4$: Yb$^{3+}$/Er$^{3+}$ (Yb/Er), or co-doped cores coated with sensitizing shells, such as $\beta$-NaYF$_4$: Yb$^{3+}$/Er$^{3+}$ @ $\beta$-NaYF$_4$: Yb$^{3+}$ (Yb/Er@Yb). Additionally, the disclosed structure allowed the sandwich UCNPs to produce intense upconversion emissions at a lower power excitations density than conventional Yb/Er and the Yb/Er@Yb UCNPs.

In some embodiments, the first and third layers comprise the same or different sensitizer dopant, and the second layer comprises an emitter dopant. For example, with respect to FIGS. 3A and 3B, a 3-layered structure may comprise two sensitizer layers (4 and 6 in FIGS. 3A and 3B) with an emitter layer 2 in between. Typically, the two sensitizer layers each independently comprise a substrate that is doped with sensitizer dopant, such as sensitizer ions, and the emitter layer comprises a substrate that is doped with emitter dopant, such as emitter ions.

In alternative embodiments, the first layer comprises an emitter dopant, such as emitter ions, (4 in FIGS. 3A and 3B), and the second layer comprises a sensitizer dopant, such as sensitizer ions (2 in FIGS. 3A and 3B). The third layer may comprise only the substrate without any dopant. i.e., the third layer does not comprise either sensitizer or emitter ions. In such embodiments, the third layer may be an inert layer and/or may protect against surface quenching. Alternatively, the third layer may comprise a dopant, such as in NaYF4: Tm@NaYF4 Yb@ NaYF4: Nd.

Suitable substrates for the layers include any substrate that can encompass the sensitizers and emitters, and can facilitate photon transfer between the sensitizers and emitters. Also, the substrate typically is optically transparent, to facilitate incident light exciting the sensitizers and emitted light leaving the emitters. In some embodiments, a substrate has a crystal lattice with a cutoff phonon energy of less than 1000 cm$^{-1}$. Suitable substrates include, but are not limited to, NaYF$_4$, CaF$_2$, ZrO$_2$, YVO$_4$, Y$_2$O$_2$S, GdOCl, GdOF, Y$_2$O$_3$, NaPrF$_4$, NaPmF$_4$, NaSmF$_4$, NaEuF$_4$, NaGdF$_4$, NaTbF$_4$, NaDyF$_4$, NaHoF$_4$, NaTmF$_4$, NaErF$_4$, NaCeF$_4$, NaNdF$_4$, NaLuF$_4$, NaYbF$_4$, or a combination thereof. The three layers may comprise the same substrate; or the first and third layers may comprise a first substrate and the second layer may comprise a second substrate that is different from the first substrate; or the first and third layers may comprise different substrates from each other, and the second layer may comprise a substrate that is the same as the first layer, the same as the third layer, or different from both the first and third layers. In certain disclosed embodiments, all three layers comprise a NaYF$_4$ substrate.

The sensitizer dopant may be any sensitizer dopant that absorbs the incident light and can transfer one or more photons to the emitter dopant. Suitable incident light includes any light having a wavelength of from 600 nm or less to 1300 nm or more, such as from 600 nm to 1300 nm, from 700 nm to 1,000 nm, or from 800 nm to 1,000 nm. In some embodiments, the light is, or comprises a wavelength of from 800 nm to 900 nm, such as from 800 nm to 850 nm, and in certain embodiments, the light is, or comprises a wavelength of 808 nm. In other embodiments, the light is, or comprises a wavelength of from 900 nm to 1,000 nm, such as from 900 nm to 1,000 nm, and in certain embodiments, the light is, or comprises a wavelength of 980 nm. In certain embodiments, the incident light is, or comprises, near infrared (NIR) light. Suitable sensitizer dopants include, but are not limited to, Yb ions, such as Yb$^{3+}$ ion; Nd ions, such as $Nd^{3+}$ ions; organic dyes, such as NIR emitting dyes including IR-806; or combinations thereof. In some embodiments, the sensitizer dopant comprises $Yb^{3+}$ ions and $Nd^{3+}$ ions. The organic dye may be suitable for broadband sensitization, i.e., the organic dye may be capable of absorbing photons covering a wide spectral range to achieve high conversion efficiency. In embodiments where the first and third layers each comprise sensitizer ions, the first and third layers may comprise the same sensitizer ions, or they may comprise different sensitizer ions. In some disclosed embodiments, the first and third layers each comprise the same sensitizer ions.

The sensitizer ions may comprise, consist essentially of, or consist of $Yb^{3+}$ ions. In alternative embodiments, the sensitizer ions comprise, consist essentially of, or consist of $Yb^{3+}/Nd^{3+}$ ions. In such embodiments, the ratio between $Yb^{3+}$ and $Nd^3$ ions may be 1:1, or there may be an excess of $Yb^{3+}$ ions compared to $Nd^{3+}$ ions, such as from greater than 1:1 to 2:1, 3:1, 4:1, 5:1 or more, with respect to $Yb^{3+}$ ions. Alternatively, the ratio may comprise an excess of $Nd^{3+}$ ions compared to $Yb^{3+}$ ions, such as from 1: greater than 1 to 1:@, 1:3, 1:4, 1:5 or more with respect to $Nd^{3+}$ ions.

The concentration of sensitizer dopant in the respective layer(s) may be any concentration suitable to facilitate energy transfer to the emitter layer. The concentration in the respective substrate may be from greater than zero to 100% or less, such as from greater than zero to 50 mol % or more, from greater than zero to 40 mol %, from 10 mol % to 40 mol %, from 10 mol % to 30 mol %, or from 20 mol % to 30 mol %. In some embodiments, the sensitizer has a concentration of 20 mol % in the substrate, such as 20 mol % $Yb^{3+}$, or 10 mol % $Yb^{3+}$/10 mol % $Nd^{3+}$.

The emitter, or activator, may be any emitter that can receive one or more photons from a sensitizer and emit light. Suitable emitters include, but are not limited to, praseodymium ions, promethium ions, samarium ions, europium ions, terbium ions, dysprosium ions, holmium ions, erbium ions, thulium ions, ytterbium ions, or a combination thereof. In some embodiments, the emitter comprises, consists essentially of, or consists of erbium, thulium, holmium, dysprosium, europium ions, or a combination thereof. In some embodiments, the emitter ions are 3+ ions. In certain disclosed embodiments, the emitter dopant comprises, consists essentially of, or consists of $Er^{3+}$ ions. However, in alternative embodiments, the emitter dopant comprises, consists essentially of, or consists of $Yb^{3+}/Tm^{3+}$ ions. In such embodiments, the ratio between $Yb^{3+}$ and $Tm^{3+}$ ions may be 1:1, or there may be an excess of $Yb^{3+}$ ions compared to $Tm^{3+}$ ions, or an excess of $Tm^{3+}$ ions compared to $Yb^{3+}$ ions.

The emitter may be selected to emit light of any desired wavelength. In some embodiments, the emitter is selected to emit visible and/or UV light. The emitter may be selected to minimize red light emissions and/or maximize green light emissions. In some embodiments, the emitted light has a wavelength of from 500 nm or less to 560 nm or more, such as from 500 nm to 560 nm. In certain disclosed embodiments, the emitted light comprises light having a wavelength of 540 nm, and may have a peak maximum at 540 nm.

The concentration of emitter in the respective layer may be any concentration suitable to receive energy from the sensitizer layer(s) and emit light of the desired wavelength and intensity. The concentration in the respective substrate may be from greater than zero to 100% or less, such as from greater than zero to 50 mol % or more, from greater than zero to 40 mol %, from 0.1 mol % to 40 mol %, or from 0.1 mol % to 30 mol %. In some embodiments, the emitter has a concentration of from greater than zero to 5 mol % in the substrate, such as from 0.1 mol % to 4 mol %. However, in alternative embodiments, the emitter has a concentration of from 10 mol % to 30 mol % in the substrate, such as from 20 mol % to 27 mol %, or from 25 mol % to 27 mol %. In certain embodiments where the composition comprises a detection moiety, the emitter concentration may be from greater than zero to 5 mol % in the substrate, such as from 0.1 mol % to 4 mol %, for example, 2 mol % $Er^{3+}$. In certain other embodiments where the composition comprises a capping moiety, the emitter concentration may be from 10 mol % to 30 mol % in the substrate, such as from 20 mol % to 27 mol %, or from 25 mol % to 27 mol %, for example, 25 mol % $Yb^{3+}$/0.3 mol % $Tm^{3+}$.

Each of the first, second and third layers independently has a thickness suitable to facilitate a special separation between the sensitizers and emitter, while facilitating photon transfer between the sensitizers and emitter. In some embodiments, each of the first and third layers independently have a thickness of from greater than zero to 50 nm or more, such as from 5 nm to 50 nm, from 10 nm to 50 nm, or from 20 nm to 50 nm. And the second layer may have a thickness of from greater than zero to 20 nm or more, such as from 5 nm to 20 nm or from 5 nm to 10 nm. And in some embodiments, the combination of the first, second and third layers have a combined thickness of from 15 nm to 110 nm, such as from 15 nm to 100 nm, 20 nm to 110 nm, or 20 nm to 100 nm.

A. Configuration

In some embodiments, the disclosed composition is a particle, such as a nanoparticle. The particle may have any suitable shape, and may be substantially spherical, or have a non-spherical shape, such as a hexagonal cuboid or rhombohedron shape. Typically, a nanoparticle has at least one dimension, and may have one, two or three dimensions, of less than 1000 nm, such as 750 nm or less, 500 nm or less, 250 nm or less, 200 nm or less, or 100 nm or less. In some embodiments, the nanoparticle has at least one dimension, and may have one, two or three dimensions, of from 15 nm to 100 nm, such as from 20 nm to 100 nm. And in any such particle embodiments, the first layer is the particle core, as illustrated in FIG. 3B.

In other embodiments, the disclosed composition has a planar configuration, as illustrated in FIG. 3A. In such embodiments, the planar configuration may be substantially flat, as shown in FIG. 3A, or it may be a non-flat planar configuration. With respect to FIG. 3A, face 8 may be any size suitable to facilitate absorption and emission of the light. Although face 8 is depicted as being rectangular in FIG. 3A, face 8 may be any desired shape, and in some embodiments, face 8 is rectangular and may be substantially square. In some embodiments, face 8 is from 5 mm to 100 mm or more by 5 mm to 100 mm or more, such as from 10 mm to 50 mm by from 10 mm to 50 mm, and in certain embodiments, face 8 is 25 mm by 25 mm.

The planar configuration may further comprise a fourth substrate 10 in direct physical contact with the first layer 4, as shown in FIG. 4. Typically, the fourth substrate is an optically transparent substrate, such that incident light can pass through to reach the first layer, and optionally, so that the emitted light will also pass through. The fourth substrate 10 may be any substrate suitable for use as a base and/or support for the layered composition, and/or to provide protection to the first layer and potentially, the composition as a whole, such as protection from physical interactions, such as knocks, and potential chemical, biological, or other interactions. Exemplary materials suitable for use as the fourth substrate include, but are not limited to, silica, including silica wafers, or glass slides; indium tin oxide; $NaYF_4$, $CaF_2$, $ZrO_2$, $YVO_4$, $Y_2O_2S$, GdOCl/F, $Y_2O_3$, $NaPrF_4$, $NaPmF_4$, $NaSmF_4$, $NaEuF_4$, $NaGdF_4$, $NaTbF_4$, $NaDyF_4$, $NaHoF_4$, $NaTmF_4$, $NaErF_4$, $NaCeF_4$, $NaNdF_4$, $NaLuF_4$, $NaYbF_4$, optionally undoped; or any combination thereof. In certain embodiments, the fourth substrate comprises, consists essentially of, or consists of, silica, indium tin oxide, or a combination thereof. Fourth substrate 10 may have any thickness suitable to provide support and/or protection to the first layer while still permitting sufficient light to pass through to the layered composition. Fourth substrate 10 may have a thickness of from greater than zero to 50 mm or more, such as from greater than zero to 25 mm, from greater than zero to 10 mm, from 0.5 mm to 5 mm, or from 0.5 mm to 2.5 mm.

Figures 5A, 5B:
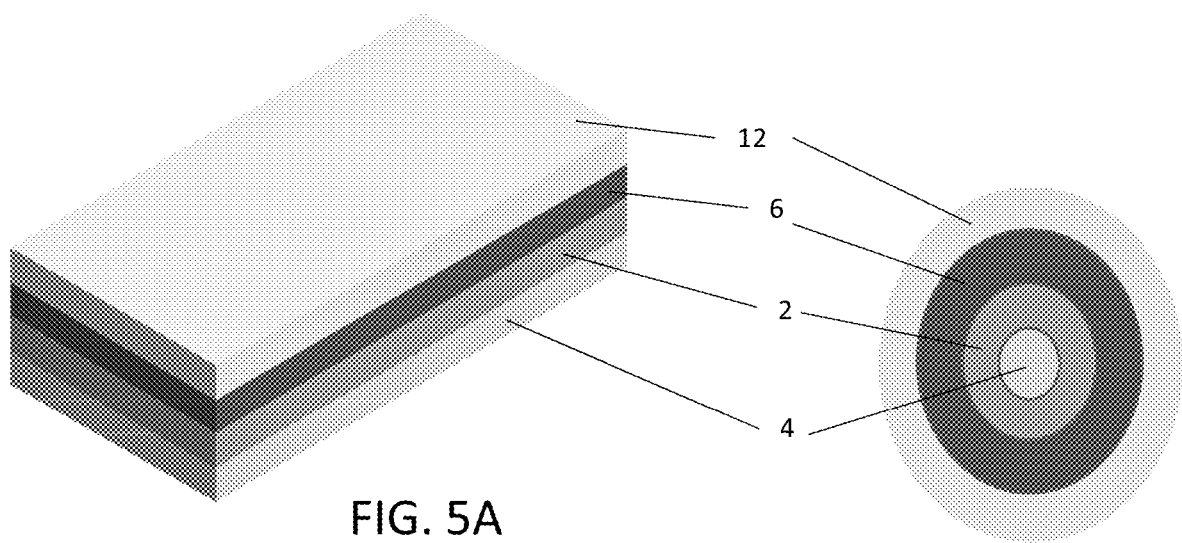
FIGS. 5A-5B are schematic diagrams showing two exemplary configurations of an embodiment of the disclosed technology that includes a fourth layer in direct physical contact with the third layer.

Additionally, or alternatively, the composition may further comprise a fourth layer 12 in direct physical contact with the third layer 6 (FIGS. 5A and 5B). FIG. 5A illustrates the planar configuration comprising layer 12, and FIG. 5B illustrates the particle configuration. Typically, layer 12 is optically transparent, such that both incident and emitted light can pass. Layer 12 may have a thickness of from greater than zero to 50 nm such as from greater than zero to 25 mm, from greater than zero to 10 mm, from 0.5 mm to 5 mm, or from 0.5 mm to 2.5 mm.

Additionally, layer 12 may comprise a material suitable to provide protection to the third layer and/or whole composition, such as protection from physical interactions, such as knocks, and potential chemical, biological, or other interactions. Additionally, or alternatively, layer 12 may be selected to facilitate attachment of an additional moiety, such as a capping moiety and/or a detection moiety. In some embodiments, layer 12 is, or comprises, silica; a polymer, such as an amphiphilic polymer; $NaYF_4$, $CaF_2$, $ZrO_2$, $YVO_4$, $Y_2O_2S$, GdOCl/F, $Y_2O_3$, $NaPrF_4$, $NaPmF_4$, $NaSmF_4$, $NaEuF_4$, $NaGdF_4$, $NaTbF_4$, $NaDyF_4$, $NaHoF_4$, $NaTmF_4$, $NaErF_4$, $NaCeF_4$, $NaNdF_4$, $NaLuF_4$, $NaYbF_4$, optionally undoped; or any combination thereof. In certain embodiments, layer 12 is, or comprises, silica, a polymer, or a combination thereof. In particular embodiments, layer 12 is a silica layer and may be a non-porous silica layer, or a porous silica layer. In certain embodiments, layer 12 is a mesoporous silica layer, comprising pores of from 2 nm to 50 nm in diameter.

B. Detection Moiety

In some embodiments, the composition further comprises a detection moiety. The detection moiety may be any moiety suitable for detecting a desired target, such as biological or non-biological target. Suitable detection moieties include, but are not limited to, an oligonucleotide, polypeptide, antibody, antigen, or a combination thereof. The oligonucleotide may be DNA, such as single or double strand DNA; RNA; a functional nucleic acid, such as an aptamer; or a combination thereof. The polypeptide may be a protein, enzyme, or fragment thereof. Typically, the detection moiety is selected to detect a desired target. Exemplary targets include, but are not limited to, a DNA strand, an RNA strand, a polypeptide, a signaling molecule, a hormone, a steroid, a lipid, a phospholipid, an amino acid, a nucleic acid, antibody, antigen, vitamin, recreational drug, medicinal drug, poison, virus, cancer marker, or a combination thereof. In some embodiments, the composition may comprise two or more different detection moieties, such as 2, 3, 4, 5, or more detection moieties. The two or more detection moieties may be selected to detect two or more targets, such as 2, 3, 4, 5, or more targets. Additionally, or alternatively, two or more detection moieties may be included in the composition to detect the same target, for example, in examples where there is more than one way to detect a single target.

In certain examples, the target is a small molecule (such as a drug, protein, or metal), the detection moiety may be a functional nucleic acid molecule, such as an aptamer or aptazyme (e.g., DNAzyme or RNAzyme). Functional nucleic acids can also contain native or modified nucleotides. Functional nucleic acids may be selected to bind to a wide range of analytes with high affinity and specificities.

Aptamers are nucleic acids (such as DNA or RNA) that recognize targets with high affinity and specificity. For example, the dompamine aptamer binds dopamine as its corresponding target. Aptazymes (also called allosteric DNA/RNAzymes or allosteric (deoxy) ribozymes) are DNA/RNAzymes regulated by an effector (the target molecule). They typically contain an aptamer domain that recognizes an effector and a catalytic domain. The effector can either decrease or increase the catalytic activity of the aptazyme through specific interactions between the aptamer domain and the catalytic domain. Therefore, the activity of the aptazyme can be used to monitor the presence and quantity of the effector (i.e., target).

Methods of identifying a functional DNA that is specific for a particular target agent have been described in several patents (e.g., U.S. Pat. Nos. 7,192,708; 7,332,283; 7,485, 419; 7,534,560; and 7,612,185, and US Patent Publication Nos. 20070037171 and 20060094026, describe methods of identifying functional DNA molecules that can bind to particular ions, such as lead and cobalt). In vitro selection methods can be used to obtain aptamers for a wide range of target molecules with exceptionally high affinity, having dissociation constants as high as in the picomolar range. For example, aptamers have been developed to recognize metal ions such as Zn(II) and Ni(II); nucleotides such as adenosine triphosphate (ATP); and guanine; co-factors such as NAD and flavin; antibiotics such as viomycin and streptomycin; proteins such as HIV reverse transcriptase and hepatitis C virus RNA-dependent RNA polymerase; toxins such as cholera whole toxin and staphylococcal enterotoxin B; and bacterial spores such as the anthrax. Aptamers are also available for other targets, including lysozyme, thrombin, human immunodeficiency virus trans-acting responsive element (HIV TAR), hemin, interferon γ, vascular endothelial growth factor (VEGF), prostate specific antigen (PSA) dopamine, and heat shock factor 1 (HSF1). Aptamers are also available for cells, such as cancer cells and bacteria. In addition, general strategies to design DNA aptazymes, by introducing aptamer motifs close to the catalytic core of DNAzymes, are available. In certain disclosed embodiments, the detection moiety is an aptamer, such as a dopamine aptamer.

The detection moiety is attached to the layered composition by a suitable technique known to persons of ordinary skill in the art. In some embodiments, the detection moiety is covalently attached to the composition. The detection moiety may be attached to the third layer 6 or to fourth layer 12, and may be directly attached, or attached though a conjugating moiety. Suitable conjugating moieties include any moiety that can attach to the third layer 6 or to fourth layer 12 and also to the detection moiety. A conjugating moiety is typically bifunctional, with one functional group suitable to attach to the third or fourth layer of the composition, such as a thiol moiety, and the second moiety suitable to attach to the detection moiety, for example, a silane moiety. In some embodiments, the conjugating moiety is a mercaptoalkyl silane, with an alkyl moiety having a length of from 1 to 25 carbons or more, such as from 1 to 15 carbon atoms, from 1 to 10 carbon atoms, or from 1 to 6 carbon atoms. Alternatively, the conjugating moiety may be a mercapto(heteroalkyl)silane, where the heteroalkyl moiety is from 2-25 atoms in length, such as from 2-15, 2-10 or 106 atoms and one or more of the carbon atoms in the alkyl chain are replaced by a heteroatom, such as O, S or N. In certain disclosed embodiments, the conjugating moiety was (3-mercaptopropyl) trimethoxysilane. Additional information concerning conjugating moieties can be found in *Bioconjugate Techniques*, by Greg Hermanson (3$^{rd}$ edition, Academic Press) which is incorporated herein by reference in its entirety.

The disclosed composition may further comprise a quenching moiety. The quenching moiety may be selected to reduce or substantially prevent observable emitted light from the composition. Additionally, or alternatively, the quenching agent may be selected to attach to the detection moiety, optionally through a non-covalent attachment, such as adsorption, and to be released when the detection moiety binds to the target of interest. In some embodiments, a higher concentration of the target in a sample, results in a larger amount of the quenching moiety being released from the detection moieties. This process can provide a quantitative as well as qualitative measure of the amount of the target present in the test system, due to the increasing amount of emitted light as the concentration of target increases.

Figure 20:
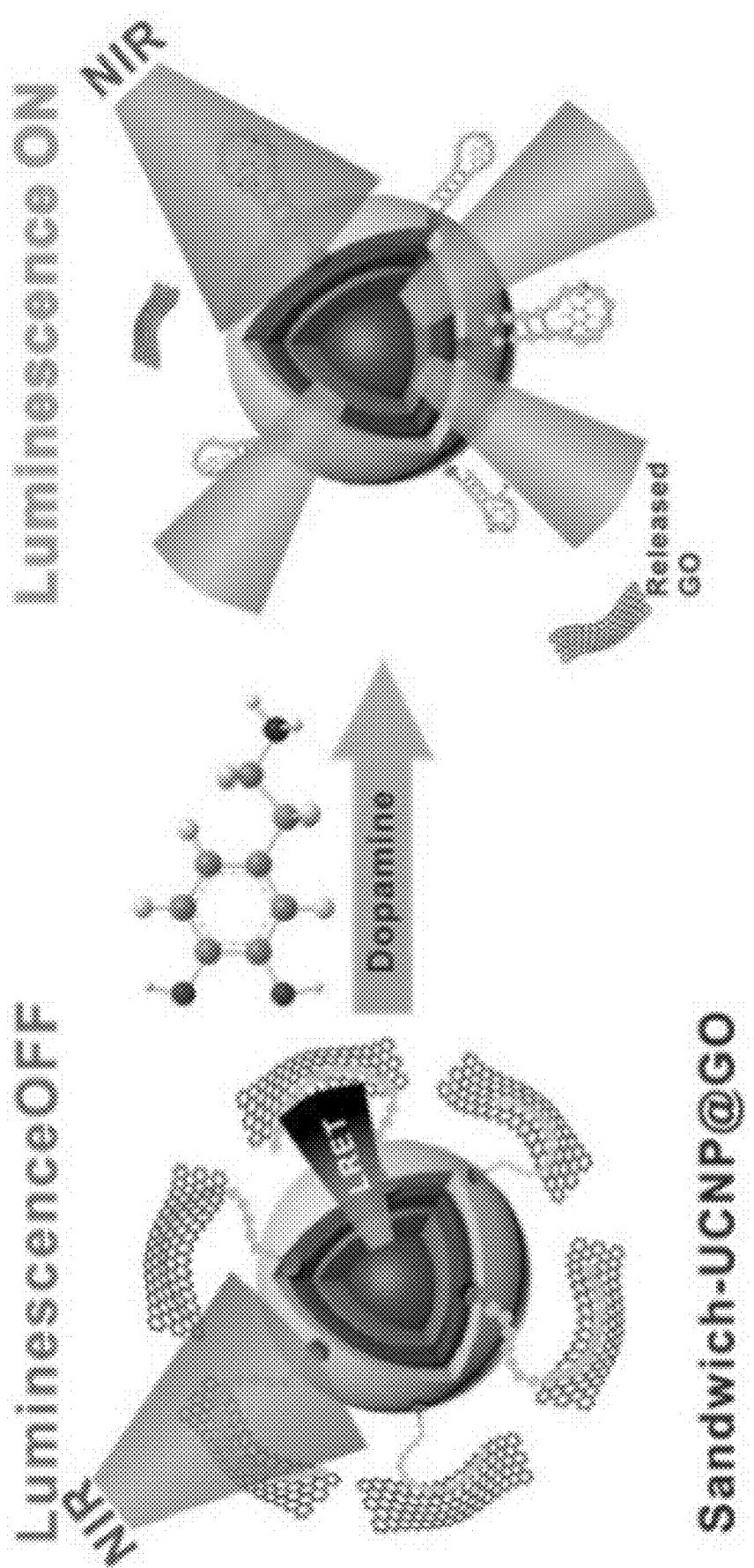
FIG. 20 is a schematic diagram illustrating how embodiments of the disclosed layered composition can be used as an upconversion luminescence sensor.

In some embodiments, the detection moiety is an oligonucleotide, such as a functional nucleic acid, and the quenching moiety associates with the nucleic acid in the absence of the target. However, when the target is present, the nucleic acid forms a particular secondary and/or tertiary structure when the target is bound, for example, as illustrated in FIG. 20. The quenching moiety is released as this secondary and/or tertiary structure is formed.

The quenching moiety may be any moiety suitable to reduce or prevent emissions. In some embodiments, the quenching moiety is graphene, graphene oxide, $MnO_2$, $MoS_2$, gold, such as gold nanoparticles, or a combination thereof. In certain embodiments, graphene or graphene oxide is used.

Also provided are mixtures of the disclosed compositions containing a detection moiety. In some examples, for example when multiple different targets are to be detected with the disclosed methods, the mixture includes a plurality of the disclosed compositions (e.g., disclosed particles). In such a mixture, each sub-population of compositions is specific for a target of interest (e.g., each subpopulation of compositions in the mixture contains a detection moiety specific for a different target of interest). Each sub-population may comprise at least one of the disclosed compositions, and may comprise two or more compositions, such as at least 2, at least 5, at least 10, at least 20, at least 30, or at least 50 compositions (e.g., disclosed particles), optionally all having the same composition, or all having detection moieties selected to detect the same target. In some examples, the mixture includes from 2 to 10 or more different sub-populations, such as at least 2, at least 3, at least 4, at least 5, or at least 10 different sub-populations of the disclosed compositions, and may include from 2 to 10 or more different detection moieties, such as at least 2, at least 3, at least 4, at least 5, or at least 10 different detection moieties, respectively, to detect from 2 to 10 or more, such as at least 2, at least 3, at least 4, at least 5, or at least 10 different targets. Each sub-population may comprise a different chemical profile. For example, each sub-population may comprise a different sensitizer, a different substrate in any or all of the first, second and third layers, a different emitter, or a combination thereof. The various combinations of sensitizers, substrates and/or emitters may be selected to provide different emitted signals, such as light having different wavelengths, or wavelength profiles, such that the presence or absence of different targets in a single sample can be determined. The disclosed compositions containing a detection moiety in such a mixture may include one or more quenching moieties. In some examples, such a mixture is used to detect multiple targets simultaneously or contemporaneously, for example in the same sample.

C. Capping Moiety

In some embodiments, the composition comprises a porous outer layer, such as layer 12 in FIGS. 5A and 5B. The porous layer may be a porous silica layer and/or may be a mesoporous layer, such as a mesoporous silica layer. Such embodiments may be used in therapeutic compositions, such as those described herein, where a therapeutic agent may be loaded into at least a portion of the pores of the outer layer. In such embodiments, the disclosed composition may further comprise a capping moiety. The capping moiety may be any moiety suitable to inhibit and/or substantially prevent early release of the therapeutic agent from the pores. Exemplary capping moieties include, but are not limited to: azo derivatives, heteroaryl azo derivatives, diarylethenes, imines derivatives, acylhydrazones, hydrazones, hemithioindigo and derivatives thereof, donor-acceptor Stenhouse adducts, or a combination thereof. In certain disclosed embodiments, the capping moiety is a hydrazone and/or may comprise a spiropyran moiety, such as

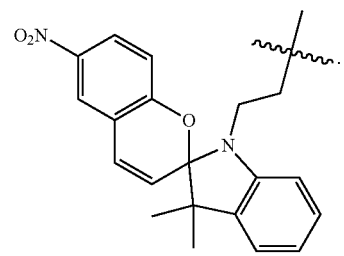 [SMILES: *CCN1c2ccccc2C(C)(C)C12C=Cc1cc([N+](=O)[O-])ccc1O2]

Figure 34:
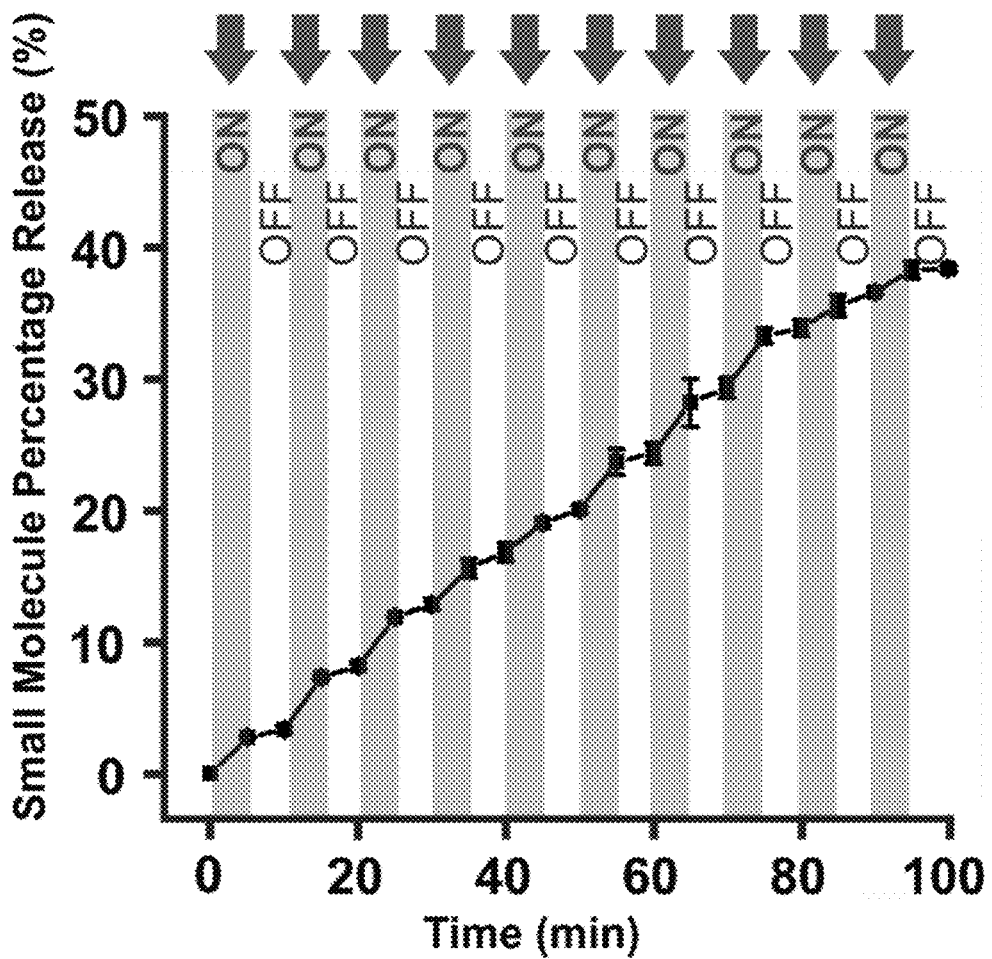
FIG. 34 is a graph of small molecule percentage release versus time, illustrating the small molecule release profile of the 808 nm NIR-mediated controlled release of fluorescein as model small molecule, and showing an observed "on-off" release pattern that demonstrates a temporal control ability.

The capping moiety may be selected to release at least a portion of the therapeutic agent upon exposure to UV and/or visible light, such as the light emitted by embodiments of the disclosed composition upon exposure to a suitable incident light, such as NIR. The capping moiety may continue to release the therapeutic agent while the disclosed composition is exposed to the incident light and may continue to release the agent after the light is removed, that is, the release is irreversible. However, in some embodiments, the capping moiety opens to release therapeutic agent in response to the composition being exposed to the incident light, and then closes or relaxes to inhibit or substantially prevent release when the incident light is removed, such that release and preventing release are reversible actions (FIG. 34 and Scheme 1).

Scheme 1

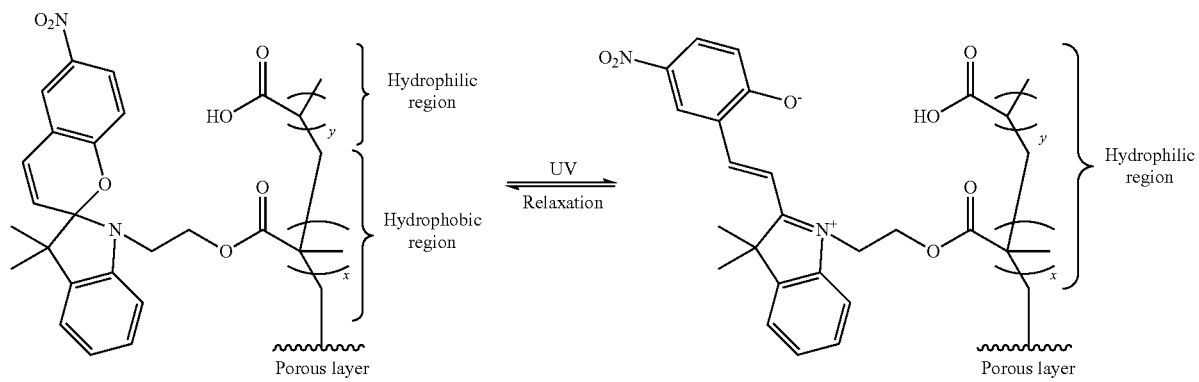

With respect to Scheme 1, an acrylic acid-based polymer comprising the spiropyran capping moiety is attached to the porous layer, such as a porous silica layer. The capping moiety forms a hydrophobic region adjacent to the porous layer, while free acid moieties on the polymer form a hydrophilic region above the hydrophobic region. The hydrophilic region interacts with the aqueous environment of a biological system to which the composition is exposed. However, the presence of the hydrophobic region substantially prevents the aqueous biological environment from interacting with the porous layer and thereby substantially prevents the therapeutic agent that is loaded in the porous layer from being released into the aqueous environment.

On exposure to NIR radiation, the disclosed composition emits UV radiation that causes the spiropyran moiety to open such that it may form a zwitterionic structure. This change in chemical structure results in the hydrophobic region becoming hydrophilic. Accordingly, the aqueous biological environment is able to interact with the porous layer thereby facilitating release of at least a portion of the therapeutic agent molecules into the biological environment. However, when disclosed composition is no longer exposed to NIR light, it stops emitting UV radiation and the capping moiety relaxes back to the closed form, thereby reestablishing the hydrophobic region and substantially stopping further release of the therapeutic agent.

The capping moiety may be attached to the silica layer via any suitable attaching moiety. In some embodiments, the attaching moiety is a silane attaching moiety and may be a silane moiety that provides a function group suitable to attach to the capping moiety, such as, but not limited to, (3-aminopropyl)triethoxysilane (APTES).

D. Therapeutic Agents

Therapeutic agents suitable for use with the disclosed composition include any therapeutic agent that can be loaded on the porous silica layer and released when the capping agent is activated. The therapeutic agent(s) may be loaded by any suitable technique known to a person of ordinary skill in the art. In some embodiments, a mixture of the disclosed composition comprising the porous layer and the therapeutic agent(s) in a suitable solvent is exposed to a first light suitable to open the capping moiety. The first light may be NIR light that results in the composition emitting UV light that causes the capping moiety to open. Or the first light may be UV light having wavelength sufficient to cause the capping moiety to open. In some embodiments, the mixture is exposed to the first light for a first time period suitable to facilitate opening of the capping moiety. The first time period may be from greater than zero to 2 minutes or more, such as from 30 seconds to 90 seconds, from 45 seconds to 75 seconds, or about 60 seconds. After exposure to the first light, the mixture is mixed, such as by stirring, sonication and/or shaking, for a second time period effective to facilitate loading. The second time period may be from greater than zero to 2 minutes or more, such as from 30 seconds to 120 seconds, or from 45 seconds to 90 seconds, and in certain embodiments, the second time period is 60 seconds. The first light may have a wavelength of from 300 nm to 400 nm, such as from 350 nm to 375 nm, and in certain embodiments, the first light has a wavelength of 365 nm. In other embodiments, the mixing proceeds while the mixture is being exposed to the first light.

After mixing, the capping moiety relaxes or closes, thereby substantially preventing the therapeutic agent(s) from being released from the composition. In some embodiments, the mixture is exposed to a second light having a wavelength sufficient to facilitate and/or aid the capping moiety to relax and/or close. The mixture may be exposed to the second light for a third time period sufficient to facilitate relaxation and/or closing of the capping moiety, such as from greater than zero to 3 minutes, from 60 seconds to 120 seconds, or from 75 seconds to 105 seconds, and in certain embodiments, the mixture is exposed to the second light for about 90 seconds. The second light may have a wavelength of from 500 nm to 600 nm, such as from 530 nm to 560 nm, and in certain embodiments, the second light has a wavelength of 543 nm.

Exemplary therapeutic agents include, but are not limited to, differentiation factors, such as Embryonic Stem Cell/induced Pluripotent Stem Cell factors (for example, Dorsomorphin, SB431542, Purmorphamine, CHIR99021, PluriSln #1, Epiblastin A, PD0325901, StemRegenin 1, SCI pluripotin, Forskolin, 2-methyl-5-hydroxytrypamine, D4476, Valproic acid, 616452, or Tranylcypromine), Hematopoietic Stem Cell factors (for example, Eltrombopag, Avatrompag, Plerixafor AMD 3100, 16,16-dimethyl-PGE2 FT1050, Pifithrin beta, MK1, H-8, 6-benzoyl-Camp, CW008, SKL2001), Neurogenesis/Neural Stem Cell/Neuronal Cell factors (for example, retinoic acid, SB216763, Kenpaullone, Neuropathiazole, Icaritin, Isobavachin, Y27632, Phenazopyridine, Aminodarone, DMH1, SB218078, LY294002, Neurodazine, DAPT, LB 205, Allopregnanolone, ICG-001, Benztropine, P7C3, P7C4A20, L-NAME, Sildenafil, KHS101, Isx, NAB2), Retinal Cell factors (for example, Nicotinamide, CKI-7, PD0325901, PS48, A83-01, WS3), Cardiac Cell factors (for example, KY02111, ITD-1, CW209E, IWR-1, Isx2, RG108, SB203580), Muscle Cell factors (for example, BIO, Lysophosphatidic acid, SQ22536, B25, BpV(phen), Q-VD-OPh, CalBio616452, "Trit"), Pancreatic Cell factors (for example, (−)-indolactam V, NECA, WS6);

Chemotherapeutic Agents, such as Alkylating Agents (for example, Mustard gas derivatives, Ethylenimines, Alkylsulfonates, Hydrazines, Triazines Nitrosureas, Cisplatin), Plant Alkaloids (for example, Vinca alkaloids, Taxanes, Podophyllotoxins, Camptothecan analogs), Antitumor Antibiotics (for example, Anthracyclines, Chromomycins), Antimetabolites (for example, Methotrexate, Pyrimidine antagonist, Purine antagonist, Adenosine deaminase inhibitor), Topoisomerase Inhibitors (for example, Ironotecan, Topotecan, Amsacrine, Etoposide, etoposide phosphate, teniposide, doxorubicin, Camptothecin), γ-Secretase Inhibitors (for example, DAPT (LY-374973), LY-685458, YO-01027, γ-Secretase Inhibitor XXI, Compound E, RO-4929097, MRK-003, MK-0752, PF-03084014);

Antiinflammatory agents, such as Ciprofloxacin, Alclofenac, Diclofenac, Fenclofenac, Indometacin, Sulindac, Fenbufen, Ibuprofen, Indoprofen, Ketoprofen, Naproxen;

Antibiotic agents, such as Piperacillin, Quinupristin, Penicillin, Clarithromycin, Nitrofurantoin, Ciprofloxacin, Telithromycin, Metronidazole, Theophylline, Levofloxacin, Gemifloxacin, Tetracycline, Azithromycin, Moxifloxacin, Erythromycin, Dalbavancin, Minocycline, Rifapentine, Clindamycin, Amoxicillin, Fidaxomicin, Tigecycline, Ceftazidime, Norfloxacin, Oritavancin, Ceftriaxone, Doxycycline, Cefuroxime, Cefotaxime, Tobramycin, Vancomycin, Telavancin, Ceftibuten, Daptomycin, Cephalexin, Gentamicin, Fosfomycin, Tedizolid, Aztreonam, Rifabutin, Meropenem, Nafcillin, Linezolid, Phenytoin, Ertapenem, Cefazolin Isoniazid,
Ofloxacin, Doripenem, Cefoxitin, Oxacillin, Neomycin, Warfarin, Rifampin, Cefepime, Digoxin;

Antiviral agents, such as Amantadine, Rimantadine, Zanamivir Oseltamivir, Ribavirin, Palivizumab, Lamivudine, Zidovudine, Didanosine Zalcitibine, Lamivudine, Stavudine, Abacavir, Tenofavir, Emtricitabine, Nevirapine, Delaviridine, Efavirenz, Saquinavir, Ritonavir, Indinavir, Nelfinavir, Amprenavir, Lopinavir/ritonavir, Atazanavir, Fosamprenavir, Efuviritide;

Anesthetic agents, such as Propofol, Etomidate, Ketamine, Methohexital;

antipyretics; antiseptics; hormones; stimulants; depressants; statins; beta blockers; anticoagulants; anti-fungals; growth factors; vaccines; diagnostic compositions; psychiatric medications/psychoactive compounds; or combinations thereof.

E. Uptake Enhancer

The composition may further comprise one or more uptake enhancers. The uptake enhancer(s) may be conjugated to the outer surface of the composition, by techniques disclosed herein and/or known to persons of ordinary skill in the art. The uptake enhancer may be any moiety suitable to increase and/or enhance the uptake of the composition by a biological system, such as a cell. In some embodiments, the uptake enhancer(s) is a peptide sequence, typically a short peptide sequence of from 2 to 10 amino acid residues, such as from 2 to 5 or from 2 to 3 amino acid residues. The peptide sequence may be selected to be specific to a particular receptor. Exemplary uptake enhancers include, but are not limited to, Arg-Gly-Asp (RGD), RGDSC, iRGD, cyclic-RGD, or a combination thereof.

II. Method for Making

Typically, the disclosed layered composition is made by synthesizing an initial layer, such as the first layer or core, and then sequentially adding the next layers onto that first layer. For example, nanoparticle compositions may be made by first synthesizing the nanoparticle core, and then synthesizing each subsequent layer onto the core. The layers typically are made by mixing substrate starting materials with a desired amount of the respective dopant in a solvent(s) suitable to facilitate nanoparticle synthesis. The solvent(s) may be comprise an organic acid, an alkene, an alcohol, or a combination thereof, and in certain disclosed embodiments, a mixture of oleic acid and octadecene was used. The starting materials for the substrate and/or dopant may be provided as a salt and/or complex, such as an acetate, ammonium, hydroxide, halide, carbonate, acetylacetonoate and/or pentadianoate, oleate, stearate, or a combination thereof.

For example, in embodiments where $NaYF_4$ is a substrate, a dopant salt, such as ytterbium acetate, is mixed with a yttrium salt, such as yttrium acetate, in a mixture of oleic acid and octadecene. After heating for a time suitable to initiate a reaction, such as from greater than zero to 2 hour or more, or from 0.5 hours to 1.5 hours, and at a suitable temperature, such as from 100° C. to 200° C., from 120° C. to 180° C. or from 130° C. to 150° C., the reaction mixture is cooled and a fluoride salt and sodium salt, such as ammonium fluoride and sodium hydroxide, are added in a suitable solvent, such as an alcohol, for example, methanol, ethanol, or propanol. The mixture is then heated slowly, such as stepwise, to remove volatile components such as the alcohol, and then heated at a temperature suitable to facilitate synthesis of the nanoparticle, such as from 200° C. to 400° C. or more, from 250° C. to 300° C., or at about 300° C. After cooling, the nanoparticles are collected. Additional information concerning the synthesis can be found in X. Xie, N. Gao, R. Deng, Q. Sun, Q.-H. Xu, X. Liu, *J. Am. Chem. Soc.* 2013, 135, 12608, which is incorporated herein by reference in its entirety.

The layers in planar embodiments may be made by techniques including chemical vapor deposition, sol-gel sedimentation, or sputtering, typically followed by high temperature (such as, for example, 1000-1500° C.) and annealing under an inert gas.

III. EXAMPLES

Example I

Materials

Erbium(III) acetate hydrate (99.9%), thulium(III) acetate hydrate (99.9%), ytterbium(III) acetate tetrahydrate (99.9%), yttrium(III) acetate hydrate (99.9%), oleic acid (technical grade, 90%), 1-octadecene (technical grade, 90%), ammonium fluoride (99.99+%), these chemicals were purchased from Sigma-Aldrich. A modified aptamer for selective binding to dopamine was custom ordered from IDT with the following sequence: 5'-Thiol GTCTCTGTGTGCGCCAGAGAACACTGGGGCAGA-TATGGG CCAGCACAGAATGAGGCCC-3' (SEQ ID NO: 1). All chemicals were used as received, without any further purification.

Methods

UV-vis absorption spectra were measured on a Varian Cary 50 spectrophotometer. Fluorescence spectra were measured on a Varian Cary Eclipse fluorescence spectrophotometer with external NIR lasers with a wavelength at 808 nm or 980 nm as excitation light sources (CNI high power fiber coupled diode laser system, FC-W-980 and FC-W-808). The total output powers for the lasers are tunable from 1 mW to 10 W. The power density was detected by 1916-R hand-held optical power meter with 818P thermophile detector (purchased from Newport Corporation, USA). All spectra were obtained from hexane dispersion of nanoparticles (1 wt %). Low resolution transmission electron microscopy (TEM) was performed on a Topcon 002B electron microscope at 200 kV. Scanning Transmission Electron Microscopy (STEM) and Electron Energy Loss Spectroscopy (EELS) spectrum were performed on a Nion Ultra-STEM 100 kV STEM with the Hermes electron monochromator. Sample preparation was carried out by placing a drop of the freshly prepared colloidal solution on a carbon-coated copper grid and allowing the solution to evaporate. Luminescence digital photographs were taken with a Nikon D3000 camera.

Measurement of luminescent lifetime: All particle containing solutions were sonicated before measurements to receive a homogenous diluted solution. For the measurement, 1 mL of particles solution was used. The concentration of all probes was 20 mg/ml. The temperature by the measurements was 21° C. The luminescence lifetime was measured by a homemade lifetime measurement setup consisting of 980 nm CW laser module of 200 mW, about 130 mW·cm$^{-2}$ from Picotronic (www.picotronic.com), an optical chopper (MC2000 with two slot chopper blade MC1F2) from Thorlabs (www.thorlabs.com) and a temperature-controlled cuvette holder with integrated magnetic stirrer. For each lifetime measurement graph, the mono-exponential-fit was used. And the values of the decay time comply the average of three measurements.

Example I-1

Synthesis of sensitizer doped core: β-NaYF$_4$: 20 mol % Yb$^{3+}$ nanoparticles (β-NaYF$_4$: Yb$^{3+}$). To a 100 mL round bottom flask, Yb(OAc)$_3$·xH$_2$O (0.4 mmol), Y(OAc)$_3$·xH$_2$O (1.6 mmol), Oleic Acid (12 mL), and octadecene (32 mL) were added. This mixture was slowly stirred, degassed, and heated to 140° C., followed by evacuating the flask atmosphere via vacuum. After 1 hour, the flask was cooled to 50° C. under argon and a solution of NH$_4$F (8 mmol) and NaOH (5 mmol) in methanol (10 mL) was added under argon gas with high speed stirring. The flask was then heated to 50° C. and maintained for 30 minutes. Then the flask was heated to 120° C. under vacuum to remove trace methanol and other volatile solvents. Finally, the flask was heated to 300° C. under argon gas and maintained for 1.5 hours. After the flask reached room temperature, the nanoparticles were centrifuged and washed with ethanol 3 times. The final particles were re-dispersed in hexane.

Example I-2

Synthesis of activator doped shell: β-NaYF$_4$: 20 mol % Yb$^{3+}$@ 2 mol % Er$^{3+}$ nanoparticles (β-NaYF$_4$: Yb$^{3+}$@β-NaYF$_4$: Er$^{3+}$). To a 100 mL round bottom flask, Er (OAc)$_3$·xH$_2$O (0.02 mmol), Y(OAc)$_3$·xH$_2$O (1.98 mmol), Oleic Acid (12 mL), and Octadecene (32 mL) were added. This mixture was slowly stirred, degassed and heated to 140° C. The flask was kept at 140° C. for 1 hour under vacuum. Later, the flask was cooled to 80° C. under argon gas. The sensitizer doped seed particles were injected via syringe and the solution was kept at 90° C. to remove hexane. Then the reaction was cooled down to 50° C. and a solution of NH$_4$F (7.2 mmol) and NaOH (4.5 mmol) in methanol (10 mL) was added under gas. The flask was kept at 50° C. for 30 minutes. After the methanol was evaporated, the flask was heated to 300° C. under argon gas and maintained for 1.5 hours. After the flask has reached room temperature, the nanoparticles were centrifuged and washed with ethanol 3 times. The final particles were re-dispersed in hexane.

Example I-3

Synthesis of sensitizer doped shell: —NaYF$_4$: 20 mol % Yb$^{3+}$@2 mol % Er$^{3+}$@ 20 mol % Yb$^{3+}$ nanoparticles (β-NaYF$_4$: Yb$^{3+}$@β-NaYF$_4$: Er$^{3+}$@ β-NaYF$_4$: Yb$^{3+}$). To a 100 mL round bottom flask, Yb(OAc)$_3$·xH$_2$O (0.4 mmol), Y(OAc)$_3$·xH$_2$O (1.6 mmol), Oleic Acid (12 mL), and Octadecene (32 mL) were added. This mixture was slowly stirred, degassed and heated to 140° C. And the flask was kept at 140° C. for 1 hour. Later, the flask was cooled 80° C. under argon gas. The activator shell coated nanoparticles synthesized above were injected via syringe and the solution is heated to 90° C. under vacuum. The reaction is the cooled down 50° C. and a solution of NH$_4$F (6.48 mmol) and NaOH (4.05 mmol) in methanol (10 mL) was added under argon gas. The flask was kept at 50° C. and maintained for 30 minutes. After the methanol was evaporated, the flask was heated to 300° C. under argon gas and maintained for 1.5 hours. After the flask reached room temperature, the nanoparticles were centrifuged and washed with hexanes 3 times. The final particles were re-dispersed in cyclohexane.

Example I-4

Construction of Aptamer based sensor: "Sandwich" structured upconversion nanoparticles (5 mg) were diluted with cyclohexane (8 ml) with IGEPAL CO-520 (400 µl) and NH$_4$OH (40 µl). And the mixture was sonicated for 30 minutes. Subsequently, TEOS (40 µl) was slowly added to this solution and it was stirred overnight at room temperature. The silica coated "sandwich" upconversion nanoparticles were then washed three times by ethanol. Once washed, a thiol-functional group was grafted on the silica surface using (3-mercaptopropyl) trimethoxysilane (20 µl) by stirring the mixture in absolute ethanol overnight. The particles were purified again via cycles of dispersing in water and centrifugation. The DNA based dopamine aptamer was conjugated by stirring with the particles in an aqueous solution for four hours followed by a similar purification step. Finally, graphene-oxide (36 µg) was coated on to the nanoparticle by adding it dropwise into the mixture solution.

Example I-5

Cell Culture and Differentiation: ReNcell VM Cells were used to achieve dopaminergic neurons. Specifically, on day 1, 1.5 million ReNcell VM Cells were placed in a 10 cm diameter TCP and treated with the medium (mixture of neurobasal medium and DMEM/F12 medium with ratio of 1:1) containing 20 ng/ml of EGF and 20 ng/ml of bFGF to generate neurospheres. After 7 days of incubation in normal culture condition (37° C., 5% CO2), neurospheres were spun down at 1.0 k rev/min for 60 sec and transferred to a laminin-coated TCP, followed by further incubation for 3 days with the medium supplemented with 20 ng/ml of EGF and bFGF. On day 10, cells were detached using Accutase detaching agent and re-plated at density of 10 million on poly-lysine and laminin-coated TCP. 2 ng/ml of GDNF and 1 mM of dibutyrl-cAMP were also introduced to cell culture media on day 10 for dopaminergic differentiation. On day 17, differentiation process was completed and after that, cell culture medium was replaced every 3 days without addition of growth factors and small molecules.

Figure 26:
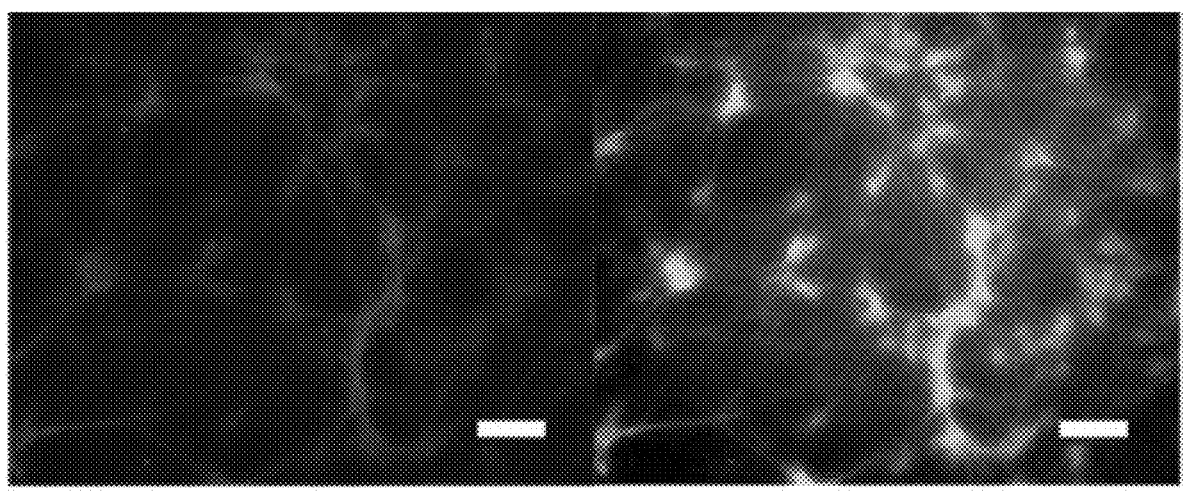
FIG. 26 is digital images of cells after cell differentiation, illustrating that these cells are dopaminergic, as shown by the green fluorescence in the right-side image after immunostaining with a dopaminergic-specific stain.
Figure 27:
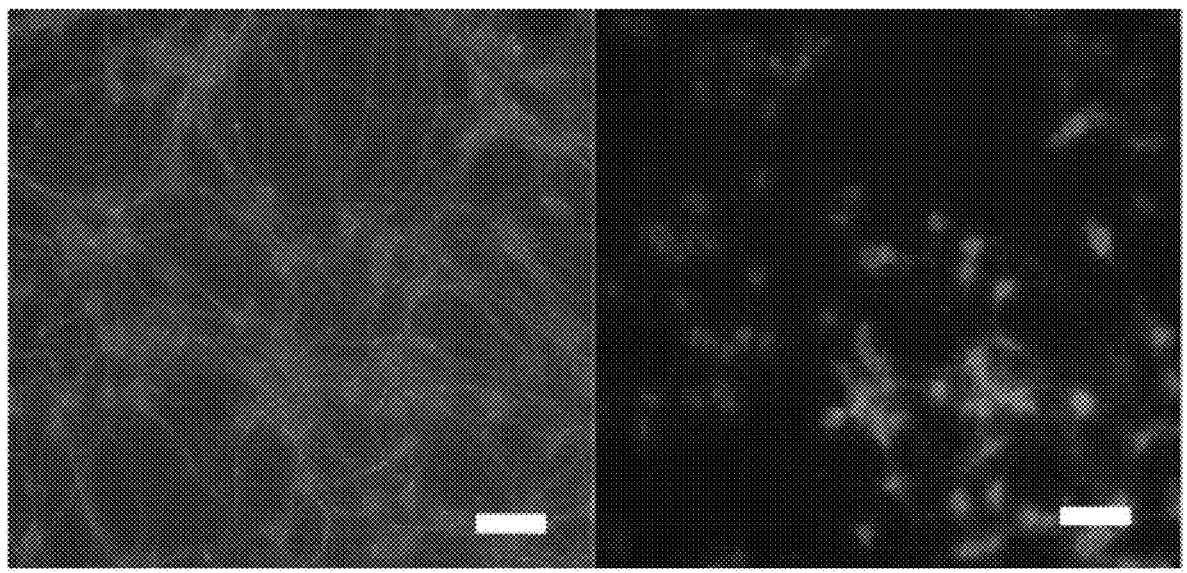
FIG. 27 is digital images of cells after cell differentiation, illustrating that these cells are not dopaminergic, as shown by the absence of green fluorescence in the right-side image after immunostaining with a dopaminergic-specific stain.

FIGS. 26 and 27 provide digital images of the cells that were immunostained to detect for dopamine, illustrating that the cell differentiation was successful. The dopaminergic cells stained positive for dopamine (green) as L-Dopa was converted to dopamine (FIG. 26, right-side image), but in the non-dopaminergic cells no dopamine staining was observed (FIG. 27, right-side image).

Figure 28:
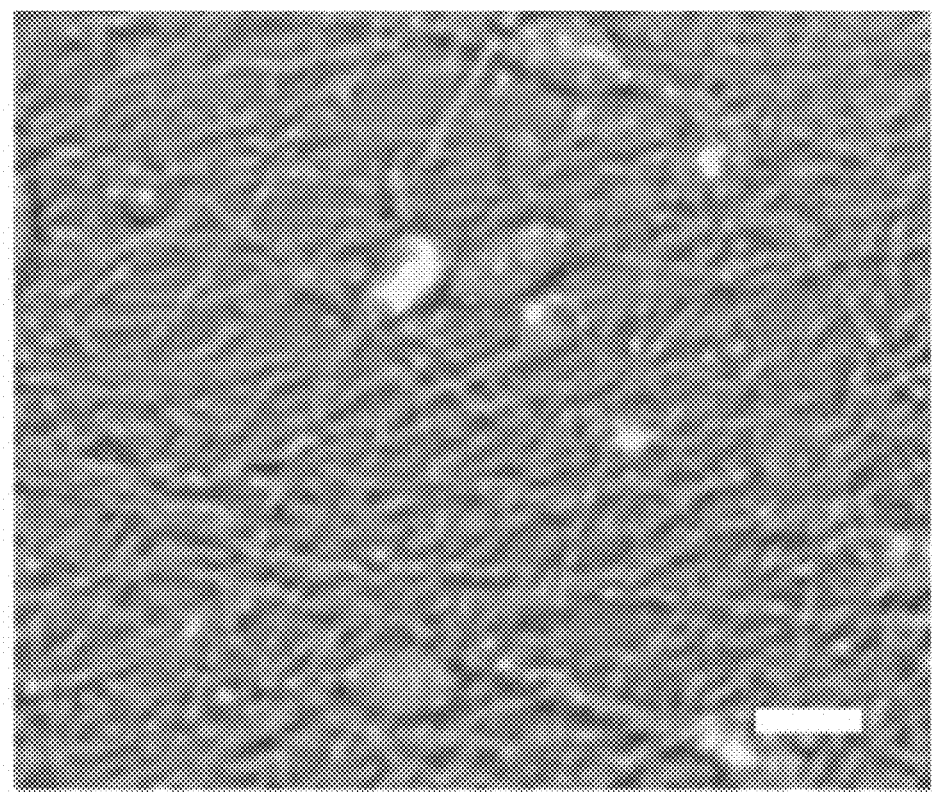
FIG. 28 is a digital image of dopaminergic cells after treatment with a biosensor comprising an embodiment of the disclosed composition, illustrating that upon exposure to incident light, a green emitted light was observed, demonstrating that dopamine was present in the cell culture.
Figure 29:
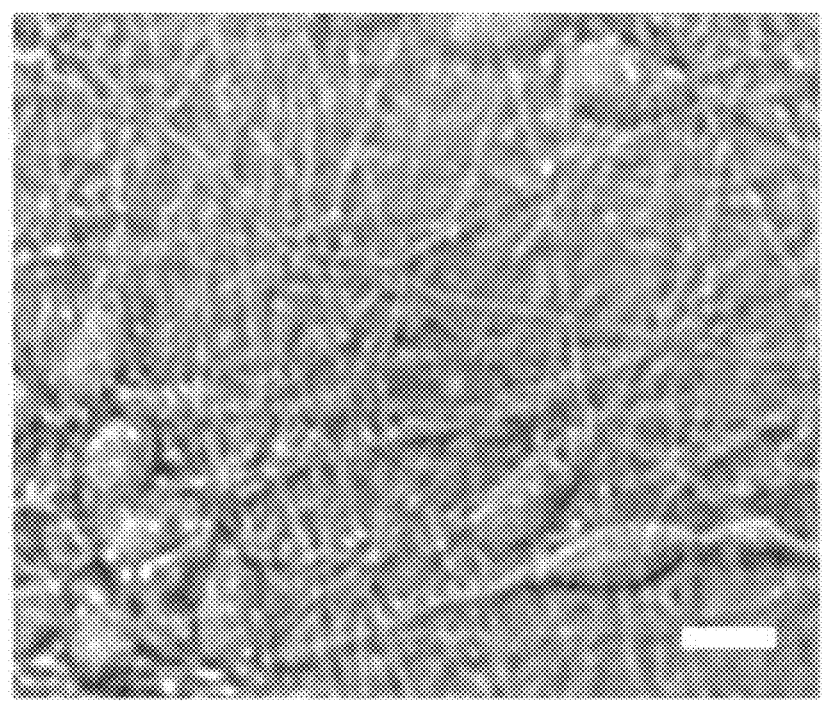
FIG. 29 is a digital image of non-dopaminergic cells after treatment with a biosensor comprising an embodiment of the disclosed composition, illustrating that upon exposure to incident light, no green emitted light was observed, demonstrating that no dopamine was present in the cell culture.

Both sets of cells were contacted with a biosensor comprising one embodiments of the disclosed composition comprising a dopamine aptamer detection moiety and graphene oxide as a quenching moiety. Upon exposure to the incident light, green emitted light was observed from the dopaminergic cells contacted with the biosensor (FIG. 28). However, in the cell culture comprising L-Dopa and non-dopaminergic cells, substantially no green emitted light was observed (FIG. 29). This illustrated how the disclosed composition comprising a detection moiety and a quenching moiety can be used to differentiate between different cell cultures, by indicating the presence or absence of a biomarker.

Example I-6

Described herein is the design and synthesis of a novel core-shell-shell structured β-NaYF$_4$: Yb$^{3+}$@ β-NaYF$_4$: Er$^{3+}$ @#β-NaYF$_4$: Yb$^{3+}$ (Yb@Er@Yb) "sandwich" structured UCNP. This Yb@Er@Yb architecture served to minimize the probability of energy back-transfer from excited state Er$^{3+}$ ions to adjacent Yb$^{3+}$ ions by spatially separating them in different layers to significantly enhance desired two photon emissions from the disclosed UCNPs in response to low power density NIR excitation, while discouraging the higher three photon energy pathways. The rationale for this architecture was based on two phenomena that are exhibited specifically in rare earth ion doped NaYF$_4$ upconversion nanoparticles. Firstly, while rare earth ions' virtual energy states have relatively long lifetimes, they are still limited, as they are for any energy states, and will deplete eventually. Secondly, resonant energy transfer (RET), the mechanism by which photon energy is transferred between the rare earth ions, is strongly affected by distance. Therefore, the disclosed design used spatial separation as a method of limiting RET to a two-photon process by making distances long enough so that three-photon processes were significantly decreased. This favored green emissions over blue emissions, as well as decreasing deleterious back-transfer based red emissions, which is a three-photon process. This was accomplished by isolating the sensitizers and activators in separate layers, decreasing the number of Yb$^{3+}$ ions in close proximity to emitting Er$^{3+}$ centers, and therefore, decreasing the probability of Er—Yb energy back transfer without decreasing Yb$^{3+}$ ion count. When compared to traditional co-doped cores structured β-NaYF$_4$: Yb$^{3+}$/Er$^{3+}$ (Yb/Er), and even co-doped cores coated with sensitizing shells β-NaYF$_4$: Yb$^{3+}$/Er$^+$ @β-NaYF$_4$: Yb$^{3+}$ (Yb/Er@Yb), the disclosed Yb@Er@Yb "sandwich" structured UCNPs provided significantly more intense, two-photon process emissions due to the mitigation of Er—Yb energy back transfer. This resulted in the disclosed UCNPs to produce intense upconversion emissions at a lower power excitations density than conventional Yb/Er and the Yb/Er@Yb UCNPs.

Figure 6:
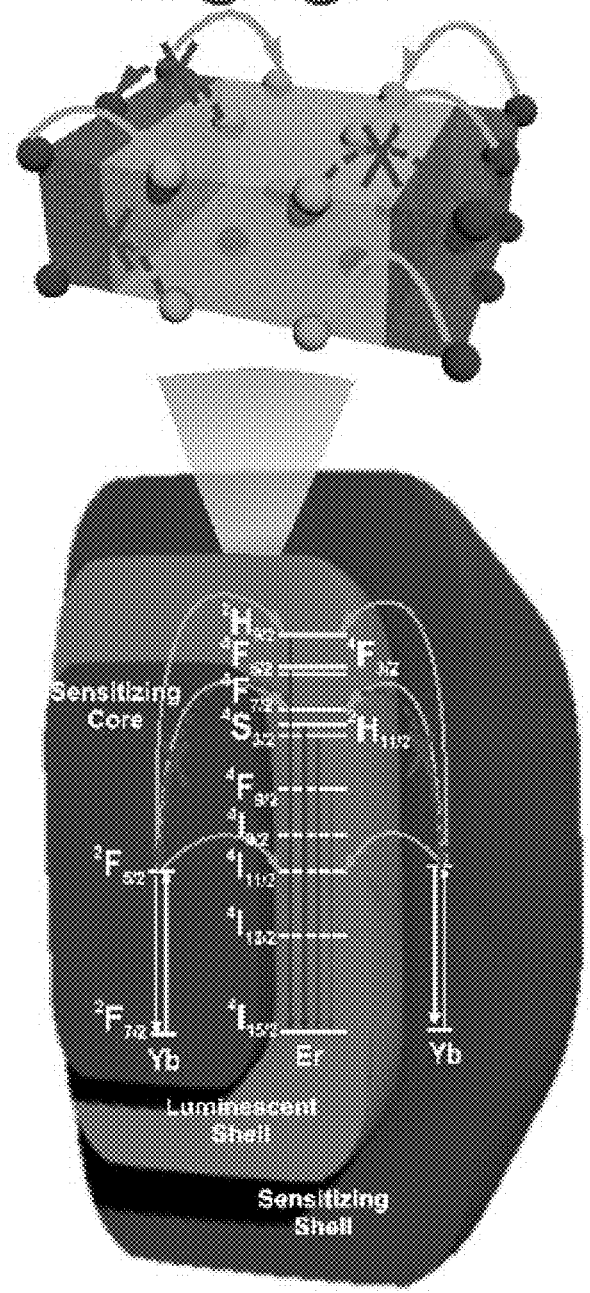
FIG. 6 is a schematic energy level diagram illustrating the energy migration mechanism for one embodiment of the disclosed novel "sandwich" structure, a Yb@Er@Yb UCNP, and showing that energy back transfer is blocked (dashed arrows with cross) due to the layered structure (sensitizing core @luminescent shell @ sensitizing shell) separation of $Er^{3+}$ and $Yb^{3+}$.

The general structure of the "sandwich" structured UCNP was composed of an activator (Er$^{3+}$) containing layer sandwiched between two sensitizing layers doped with Yb$^{3+}$, as shown in (FIG. 6). This architecture allowed for the inner and outer Yb$^{3+}$ doped sensitizing layers to efficiently harvest 980 nm NIR excitation, funneling it toward the activator containing luminescent layer where it promoted emissions from the higher energy emissive states of the activator ions. However, considering the shell's thickness, emissions requiring three or more photons were diminished due to the distance dependent nature of RET. Moreover, this specific arrangement of layers also minimized the number of nearest neighbors between the activating lanthanides in the luminescent shell (LS) and sensitizing Yb$^{3+}$ in the sensitizing core (SC) and sensitizing shell (SS), therefore minimizing the probability of Er$^{3+}$ to Yb$^{3+}$ energy back transfer (FIG. 6). Advantageously, this serves to enhance the multi-photon upconversion efficiency of the materials at low power density excitations.

Figure 7:
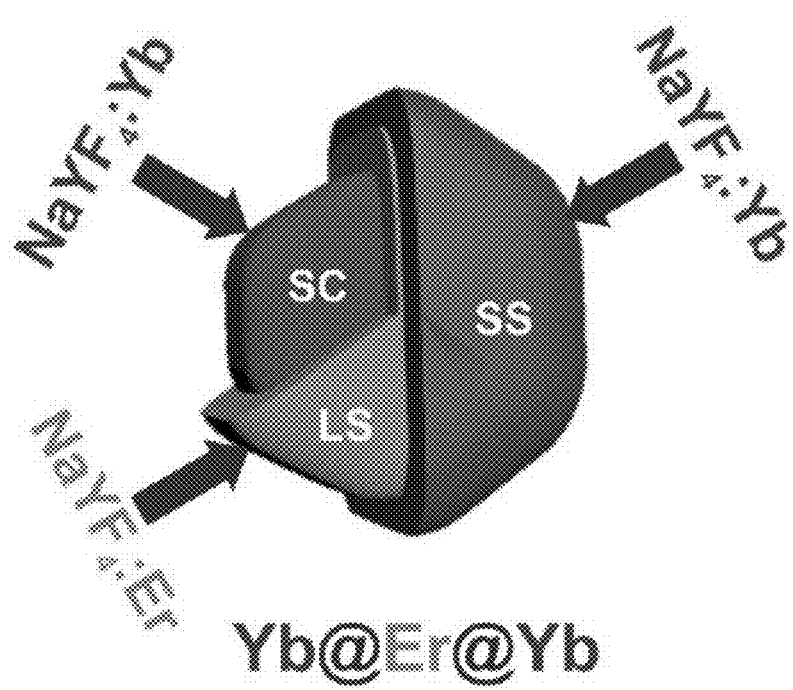
FIG. 7 is a schematic diagram of one embodiment of the disclosed three-layered composition, illustrating a Yb@Er@Yb "sandwich" structured UCNP.
Figure 8:
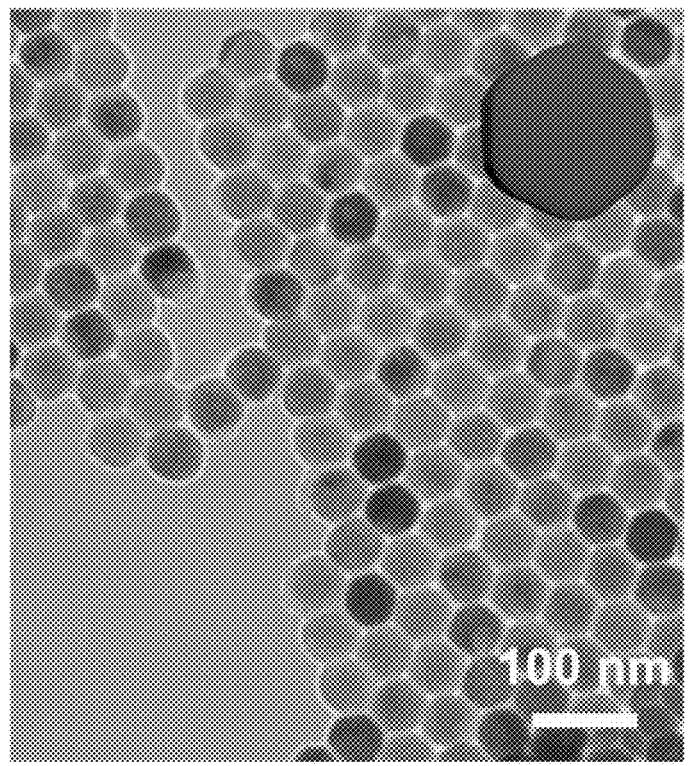
FIG. 8 is a TEM image illustrating the size and morphology of the core (i.e., first layer) of a synthesized Yb@Er@Yb "sandwich" structured UCNP.
Figure 9:
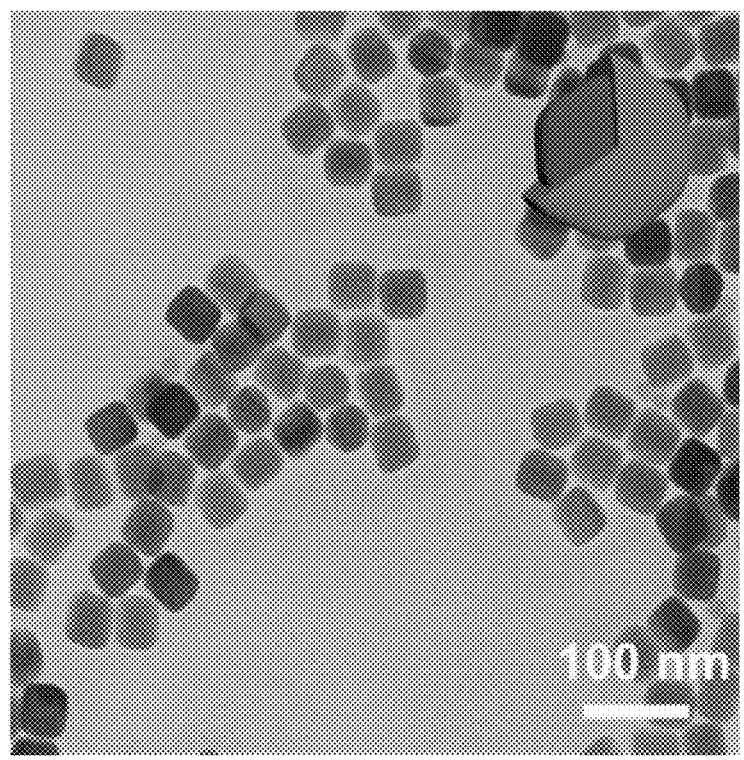
FIG. 9 is a TEM image illustrating the size and morphology of the second layer of a synthesized Yb@Er@Yb "sandwich" structured UCNP.
Figure 10:
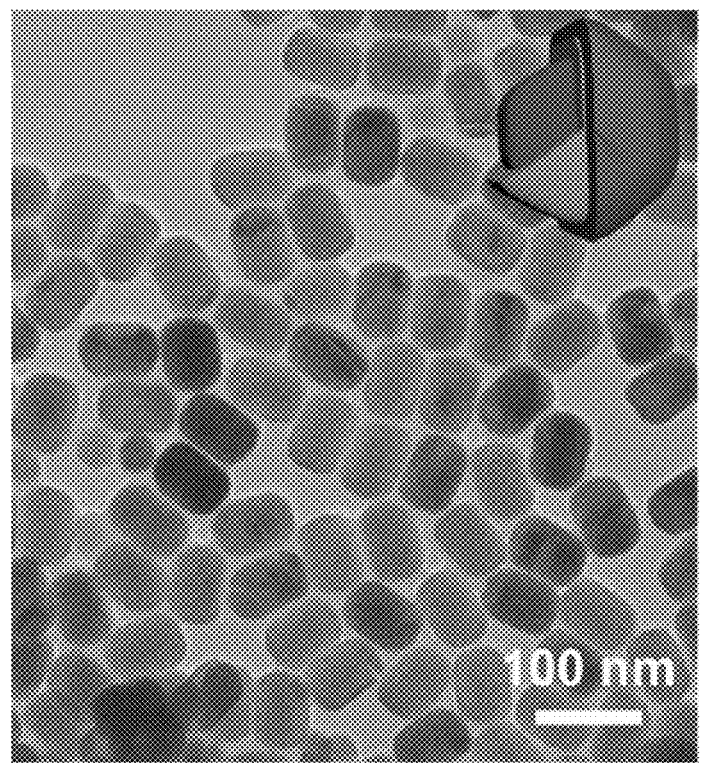
FIG. 10 is a TEM image illustrating the size and morphology of the third layer of a synthesized Yb@Er@Yb "sandwich" structured UCNP.

Following these general design considerations, NaYF$_4$ was selected as an exemplary host matrix due to its well-characterized nature, low lattice phonon energies, and relatively higher upconversion efficiencies as compared to other materials. To construct the Yb@Er@Yb "sandwich" structure, as illustrated in FIG. 7, a sensitizing core was synthesized that contained the NaYF$_4$ substrate doped only with Yb$^{3+}$ as a sensitizer (FIG. 8). This core first layer was then coated with a 10 nm thick activator or emitter layer containing a luminescent dopant (Er$^{3+}$) but no sensitizer (FIG. 9). This second layer was specifically designed to be 10 nm thick, as this put the innermost Ln ions (i.e., Er$^{3+}$) of this layer within 5 nm of the Yb$^{3+}$ doped layers, facilitating efficient energy migration to the luminescent Ln centers for up to two-photons while mitigating further transfer. Then, a 10 nm thick outer (third) sensitizing layer was grown over the particle, sandwiching the luminescent second layer between the Yb$^{3+}$ containing sensitizing core and sensitizing layer, thereby allowing for efficient energy migration to the luminescent lanthanide ions, and more intense upconversion emissions (FIG. 10).

Figure 11:
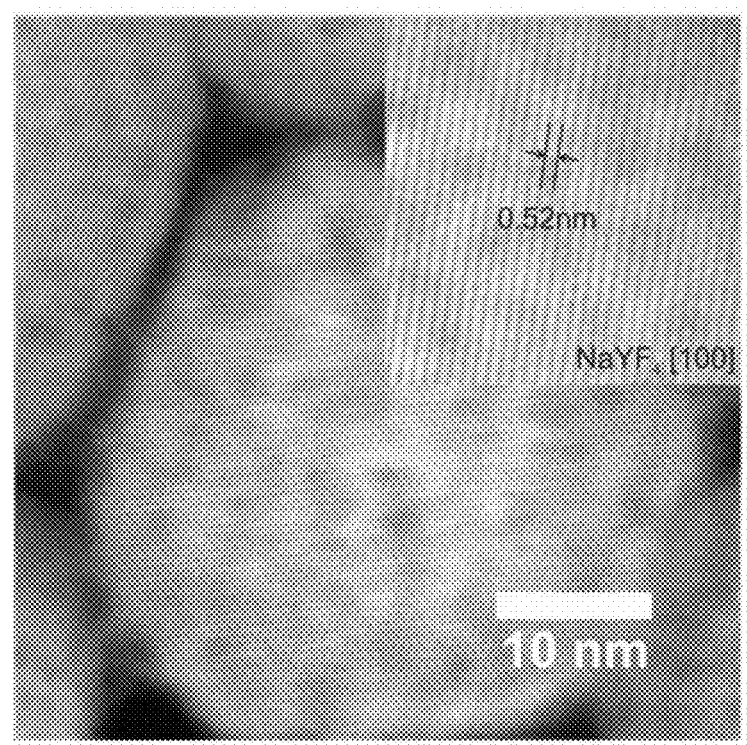
FIG. 11 is a high resolution TEM (HR-STEM) image of Yb@Er@Yb UCNPs, with the inset illustrating the typical 0.52 nm lattice spacing of (100) crystallographic planes of $\beta$-$NaYF_4$.

High-Resolution Scanning Transmission Electron Microscopy (HR-STEM) images show the monocrystalline nature of the as-synthesized Yb@Er@Yb "sandwich" UCNPs, which bear the characteristic lattice spacing off β-hexagonal NaYF$_4$ (FIG. 11). The anisotropic shape evolution of the UCNPs from semi-spherical to hexagonal nanorods is due to the preferential growth of the material along the (100) axis due to the thermodynamically favored capping of the (001) face by oleic acid during particle growth.

Figure 12:
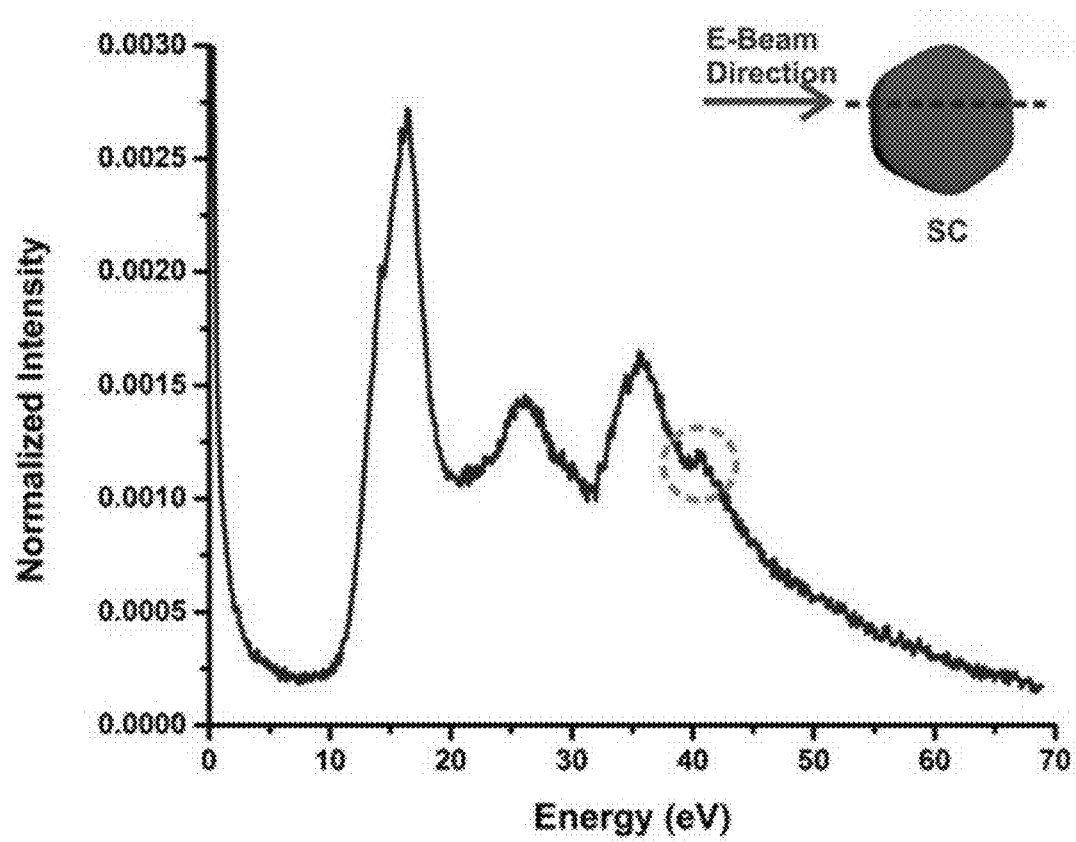
FIG. 12 is an Electron Energy Loss Spectroscopy (EELS) spectrum of sensitizing core (SC), with the circle at 40 eV illustrating the presence of $Yb^{3+}$ in the nanoparticle.
Figure 13:
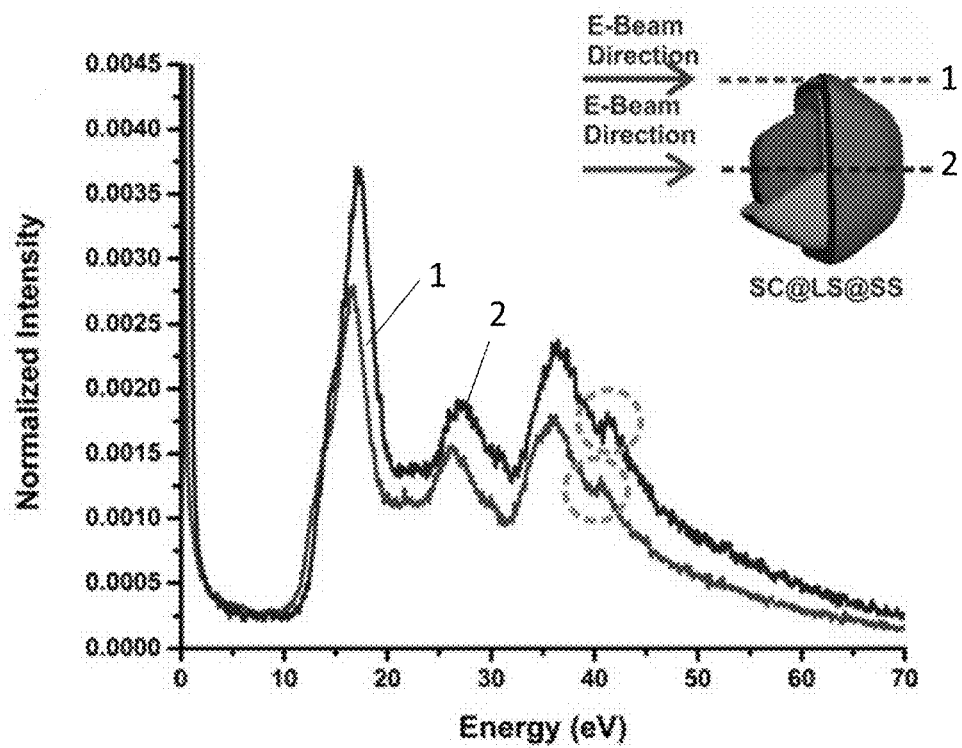
FIG. 13 is an EELS spectrum of Yb@Er@Yb "sandwich" structured UCNPs, illustrating that the Yb-specific peak at 40 eV was observed throughout the nanoparticle, since the electron probe always scans through $Yb^{3+}$ doped area after the SS layer growth.
Figure 14:
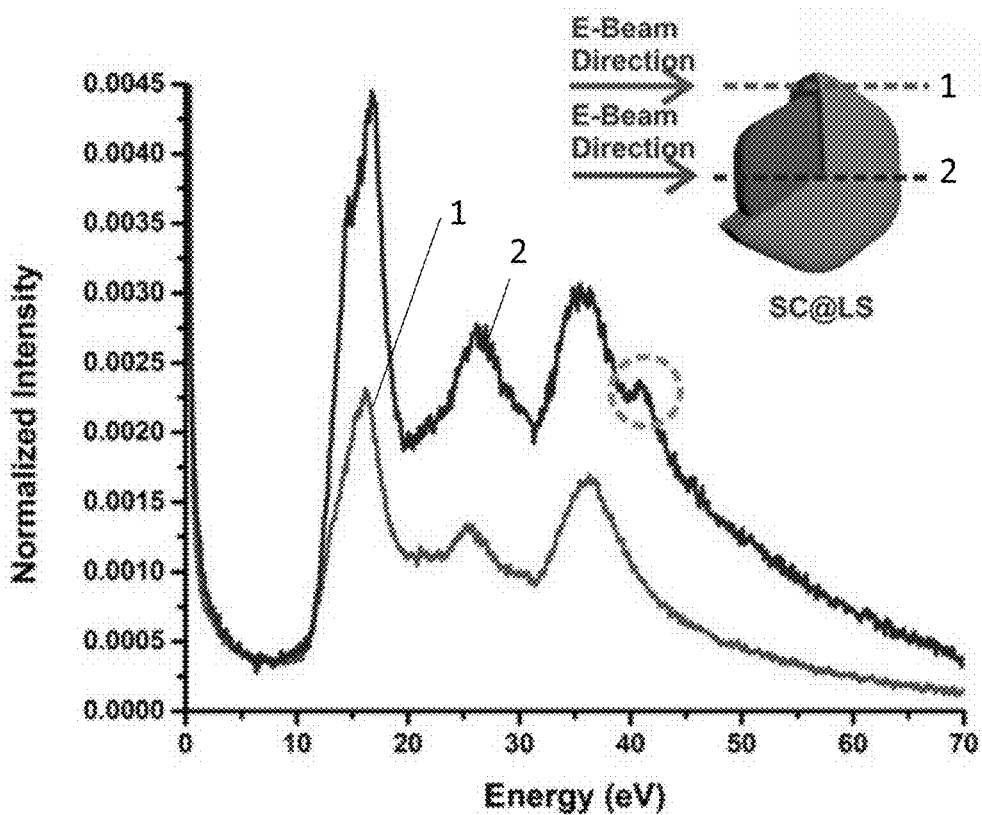
FIG. 14 is an EELS spectrum of the luminescent layer-coated sensitizing core (SC@LS), illustrating that the characteristic peak of $Yb^{3+}$ at 40 eV that is present when the center of the UCNP is exposed to the scanning electron probe (purple curve), and that the 40 eV $Yb^{3+}$ peak is absent when the scanning electron probe passes only edge (LS) of the nanoparticle, indicating the compositional separation of the two layers.

To confirm the structural and compositional integrity of the core-shell architecture, spatially-resolved step-by-step single particle Electron Energy Loss Spectroscopy (EELS) was performed in single UCNPs to verify that Yb$^{3+}$ was only detected in the sensitizing core (SC) and sensitizing shell (SS) of the Yb@Er@Yb "sandwich" structure. In the EELS spectrum of the Yb$^{3+}$ containing sensitizing core, the unique shoulder at 40 eV can be solely ascribed to the 5p to 5d transition of Yb$^{3+}$ (FIG. 12). Accordingly, this peak is only found when the EELS spectrum is taken in the SC and SS of the Yb@Er@Yb structured UCNPs, regardless of where in that layer the electron probe is scanned (FIG. 13). The EELS data illustrates the absence of the Yb$^{3+}$ in the luminescent shell (LS) (FIG. 14), which is of significance for the upconversion luminescence study.

Figure 15:
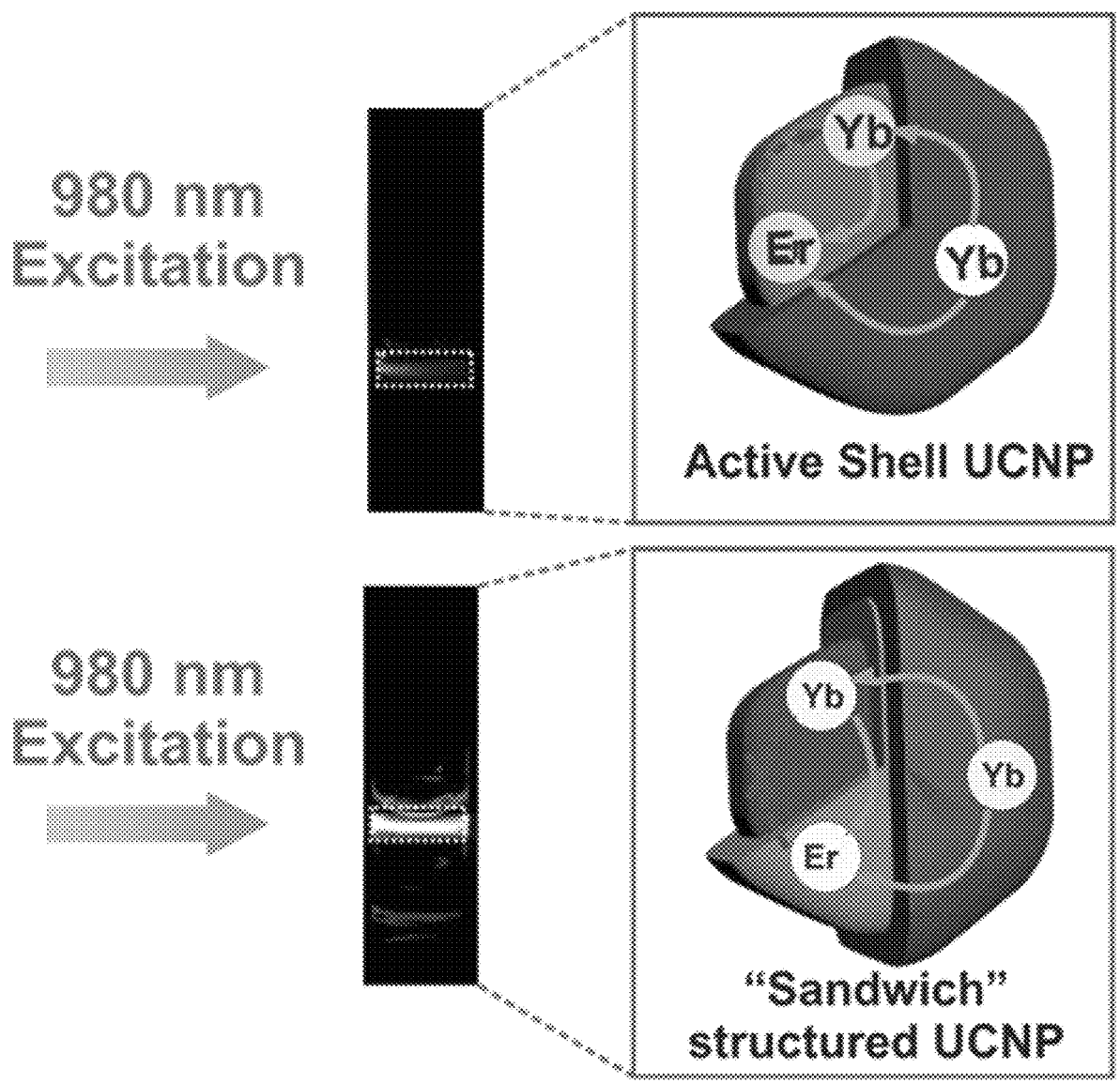
FIG. 15 provides two digital images illustrating the luminescence from Yb/Er@Yb (upper) and Yb@Er@Yb (lower) structured UCNPs in hexane solution (1 wt %) under same 980 nm laser excitation (25 W/cm$^2$), illustrating the greater luminescence from the Yb@Er@Yb structured UCNPs.
Figure 16:
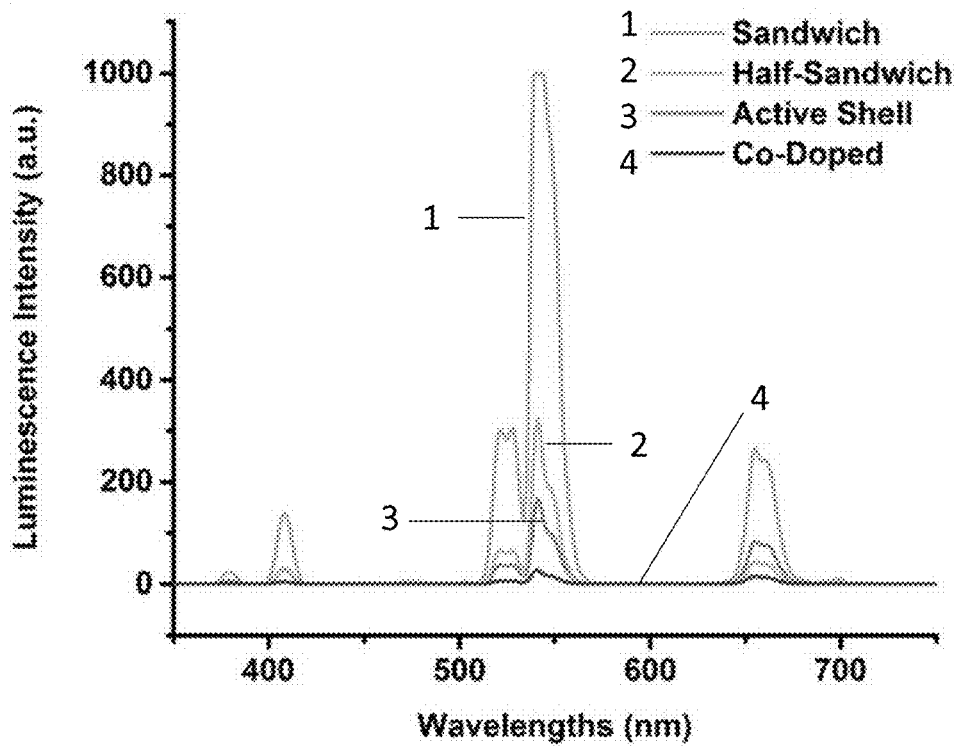
FIG. 16 is a graph of luminescence intensity versus wavelength, illustrating the greater intensity of the luminescence from Yb@Er@Yb (sandwich) UCNPs, compared with the luminescence obtained from Yb/Er (co-doped), Yb/Er@Yb (active shell), and Yb@Er (half-sandwich), when exposed to the same 980 nm NIR excitation (25 W/cm$^2$).
Figure 17:
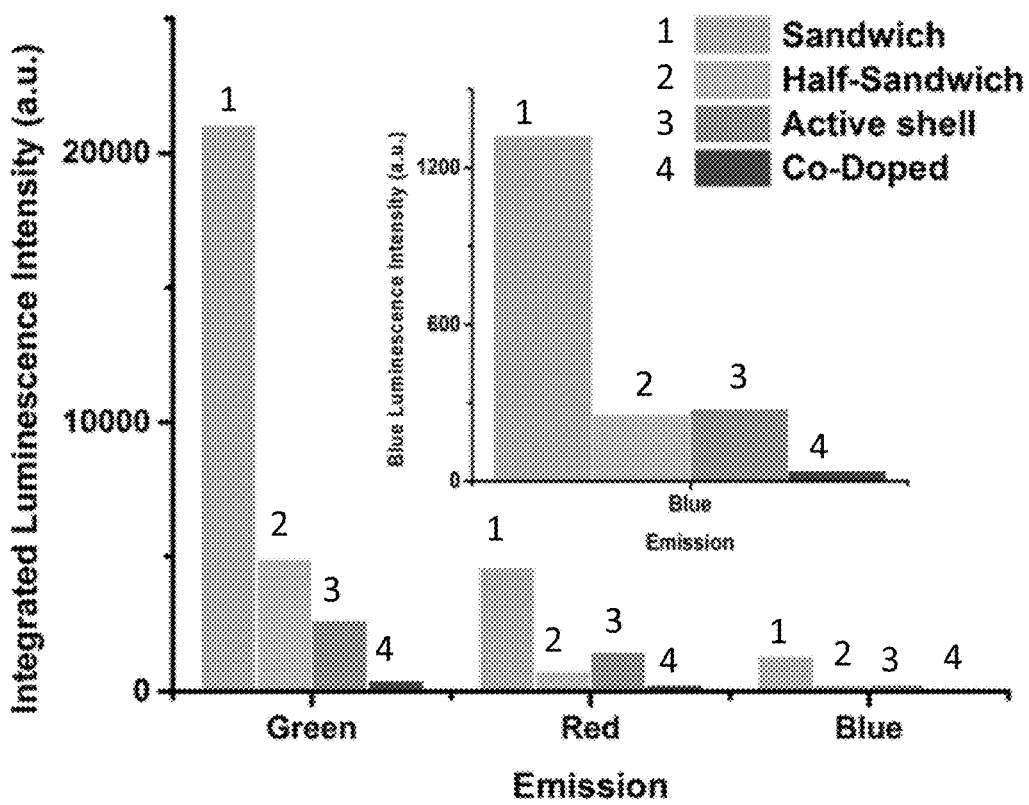
FIG. 17 is a graph of integrated luminescence intensity versus emission, illustrating the integrated luminescence intensity for the green, red, and blue emissions for the four types of UCNPs shown in FIG. 16, and showing the large increase in the green emission and green to red ratios for "sandwich" structured Yb@Er@Yb UCNPs.
Figure 18:
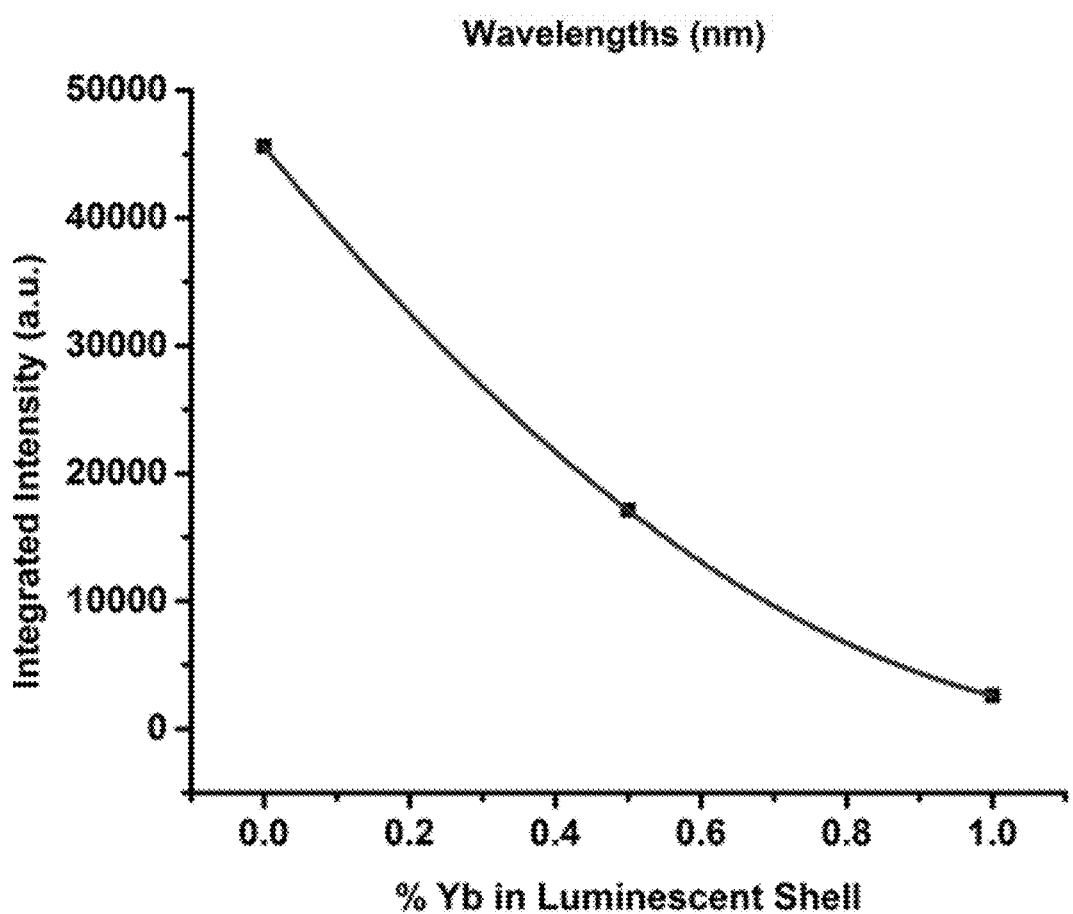
FIG. 18 is a graph of integrated intensity versus % Yb in the luminescent shell, illustrating the decrease in integrated luminescence intensity when $Yb^{3+}$ is included in the luminescent second layer in the Yb@Er@Yb "sandwich" structure UCNPs.

Next, the upconversion spectra of the synthesized Yb@Er@Yb UCNPs was investigated. By visual inspection, the Yb@Er@Yb structured UCNPs displayed a marked enhancement when compared to "active shell" Yb/Er@Yb NaYF$_4$ (FIG. 15). Similarly, when comparing the upconversion luminescence of the disclosed Yb@Er@Yb UCNPs with typical Yb/Er co-doped core UCNPs, they show a markedly enhanced luminescent output 63 times greater than the co-doped UCNPs (FIGS. 16 and 17). The structure also has a greater luminescent output than "active shell" Yb/Er@Yb nanoparticles as well, showing a 6 times total luminescence enhancement. Without being bound to a particular theory, this may be due to the mitigation of Er—Yb energy back transfer, which occurs to a much greater extent in Yb/Er co-doped core UCNP structures. Er—Yb energy back transfer has been shown to be responsible for a three-photon absorption based red emission of Yb/Er co-doped UCNPs, which proceeds through the relaxation of the population within the $^4G/^2K$ manifold, via energy back transfer, to the $Yb^{3+2}F_{7/2}$ ground state and the commensurate population of the $^4F_{9/2}$ state of $Er^{3+}$, resulting in red emission. As such, the energy back-transfer from Er—Yb can be concluded to depopulate the green emitting state in favor of red emissions, resulting in a larger ratio of red to green emissions. This observation holds true when comparing Yb/Er co-doped core UCNPs to "half sandwich" structured UCNPs (Yb@$Er^{3+}$) of the same composition (20 mol % $Yb^{3+}$ and 2 mol % $Er^{3+}$), where the only difference is the isolation of sensitizers and activators into separate shells, which mitigates the detrimental Er—Yb energy back transfer, resulting in a 35% increase in green emissions (FIG. 17). By further coating the Yb@Er "half sandwich" UCNPs with a sensitizing shell, to make Yb@Er@Yb UCNPs "sandwich" structured UCNPs, an 80 fold increase in green emissions was observed, compared to control Yb/Er co-doped UCNPs and an 8 fold increase over "active shell" Yb/Er@Yb UCNPs (FIG. 17). Moreover, to further support that back-transfer mitigation is responsible for the enhancement, the disclosed sandwich structure was synthesized with increasing $Yb^{3+}$ mol % in the middle layer (LS, the second layer) of the "sandwich" UCNPs. Significant luminescence intensity decreases were observed (FIG. 18). To further corroborate the initial hypothesis as well as to support the luminescent data, lifetime measurements were taken. Significant increases were expected due to the distance-dependent nature of RET which is utilized in the disclosed sandwich structure, designed allow for two-photon processes to occur via spatial separation by controlling shell thickness, so that the energy states deplete before the three-photon processes can occur. The lifetime measurements illustrated that Yb@Er@Yb UCNPs had lifetimes lasting as much as three times as long than more conventionally structured co-doped Yb/Er UCNPs (Table 1 and FIG. 19).

TABLE 1

Luminescent Lifetime of "sandwich" structured (Yb @ Er @ Yb) UCNPs comparing to conventional "active shell" structured (Yb/Er @ Yb) UCNP.

| Type | Lifetime by Wavelengths (μs) | | |
|---|---|---|---|
| | 420 nm | 543 nm | 660 nm |
| "Active Shell" Yb/Er @ Yb UCNPs | 210 ± 8 | 228 ± 14 | 345 ± 3 |
| "Sandwich" Yb @ Er @ Yb UCNPs | 642 ± 20 | 904 ± 5 | 979 ± 7 |

The remarkably enhanced emissions from the disclosed sandwich structured UCNPs in response to low power density excitations provided them with significant advantages over traditionally structured UCNPs, in fields such as bioimaging, sub-cellular labelling, as well as sensing due to the mitigation of the heating effect from 980 nm NIR excitation and the much higher signal-to-noise ratio achievable with the disclosed "sandwich" structure.

To demonstrate the utility of the disclosed designed UCNPs, a simple LRET-based sensor was constructed using the "sandwich" structured Yb@Er@Yb UCNPs to sensitively detect dopamine at extremely low detection limits (pM) illustrated by the schematic in (FIG. 20). With respect to FIG. 20, graphene oxide (GO) sheets cover the aptamer-functionalized silica coated surface of "sandwich" UCNP leading to a quenching of luminescence. Upon binding to analyte, dopamine in this case, the aptamer folding change releases GO from surface, resulting in recovery of upconversion luminescence. Dopamine is an important neurotransmitter which plays an important role in several neuronal circuits such as those involved in mood, emotions, behavior, motor coordination and addiction. Moreover, the loss of dopamine-producing cells is a hallmark of Parkinson's disease, which currently affects up to 10 million people worldwide. It is therefore important to develop a simple, robust, and sensitive biosensors capable of monitoring dopamine production and release from neurons.

Figure 21:
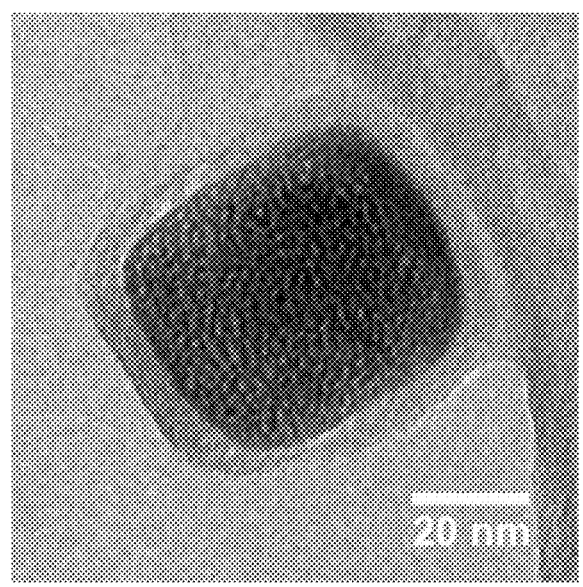
FIG. 21 is a TEM image of a silica-coated upconversion nanoparticle.
Figure 22:
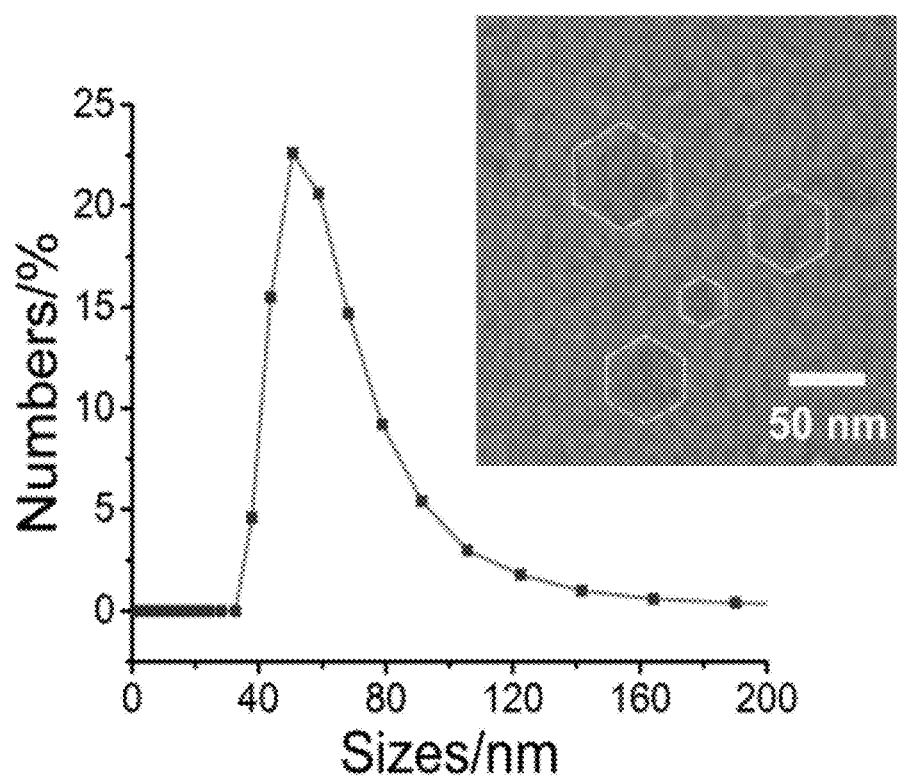
FIG. 22 is a graph of percentage versus size in nm, illustrating the sized of the graphene oxide sheets, with an insert providing a TEM image of the graphene oxide sheet.
Figure 23:
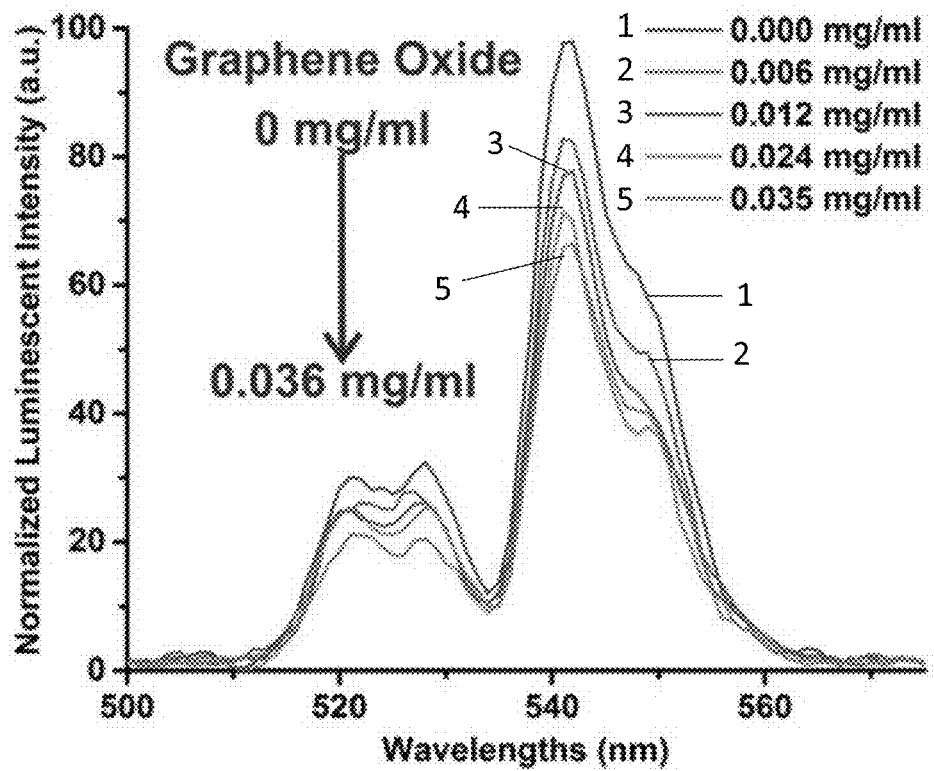
FIG. 23 is a graph of normalized luminescent intensity versus wavelength, illustrating the upconversion luminescence quenching in response to cumulative graphene oxide coating.
Figure 24:
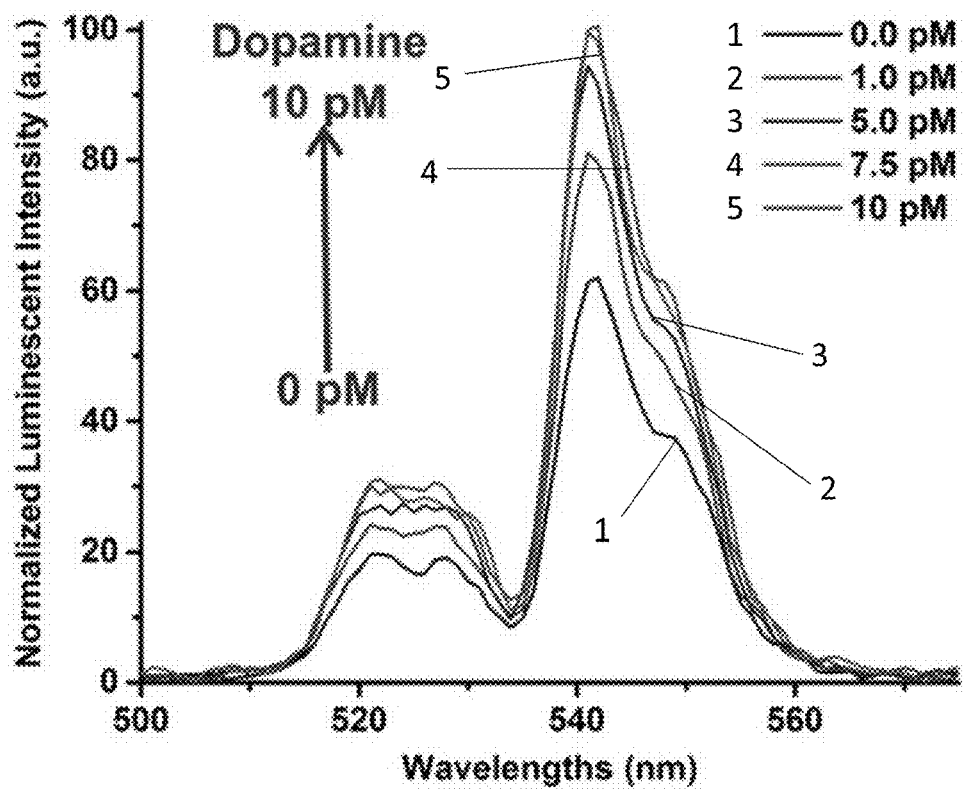
FIG. 24 is a graph of normalized luminescent intensity versus wavelength, illustrating the recovery of upconversion luminescence in response to dopamine binding.
Figure 25:
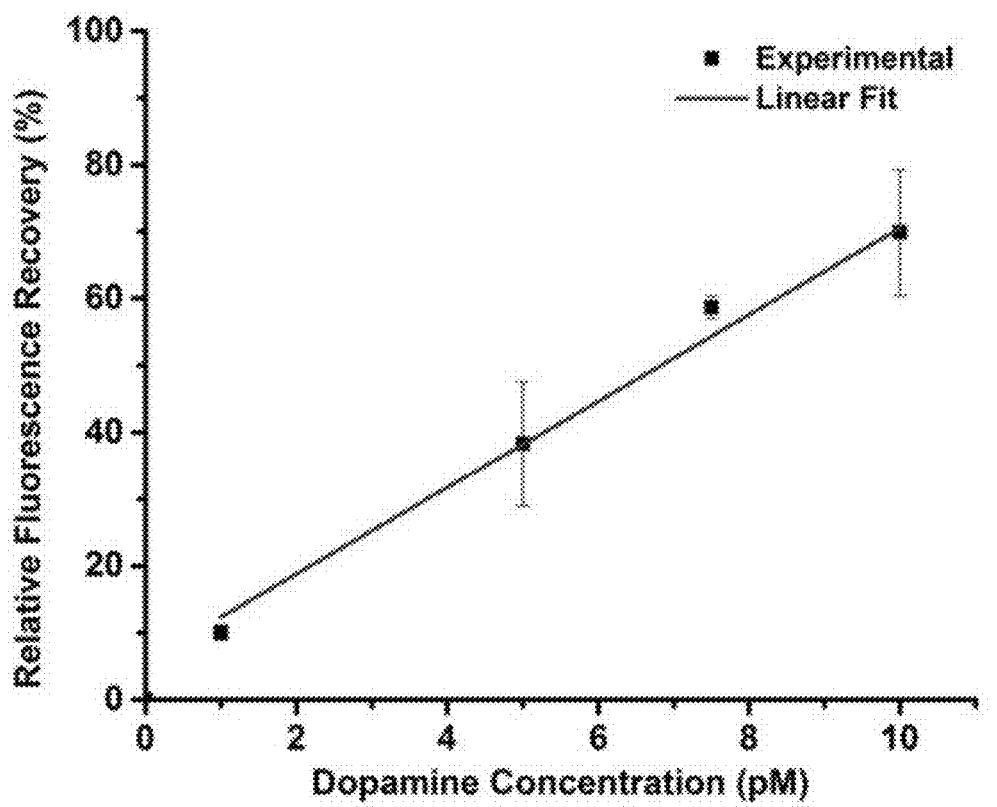
FIG. 25 is a graph of relative fluorescence recovery versus dopamine concentration, illustrating the linear relationship of the "sandwich" UCNP-based sensor's luminescence signal with different concentration of dopamine at pM concentration range.

To construct the biosensor, the sandwich structured UCNPs were first coated with a silica shell to allow for facile surface functionalization and protection from water-based luminescence quenching (FIG. 21). The silica shell was then functionalized with a modified aptamer specific for dopamine. Lastly, to finish the assembly of the biosensor, graphene oxide (GO) sheets were added (FIG. 22) at varying concentrations to the UCNP@$SiO_2$-Aptamer complex (FIG. 23). The dopamine aptamer interacted with the GO via pi-pi stacking between the GO and the nucleobases of the aptamer, thereby quenching the UCNP fluorescence in a concentration-dependent manner (FIG. 23). Upon the introduction and binding of dopamine, the aptamers resumed their 3-dimensional shape, abrogating the pi-pi interactions with GO, and thereby releasing the GO. With the release of the GO, the luminescence was again observed (FIG. 24). Due to the highly efficient upconversion process resulting from the disclosed "sandwich" structured UCNPs, detection of the dopamine was possible in a range of 1-10 pM with an $R^2=0.94$ (FIG. 25). This was three orders of magnitude more sensitive than previously demonstrated by UCNP-LRET based biosensors, which typically operate in the μM to nM range. This has significant implications for the ability of researchers to monitor the in situ production of dopamine in the cytoplasm of neurons study of related diseases such as Alzheimer's and Parkinson's, where it is present in much lower concentrations.

The unique design of the sandwich-structured three layered composition disclosed herein enabled an exemplary system to produce bright visible emissions, such as in the 500 nm to 560 nm range, in response to relatively low power density excitations. The use of low power density 980 nm NIR excitation to produce bright emissions is useful in biological applications, as it mitigates the heating effect of 980 nm NIR excitations which is a long-standing challenge of using 980 nm NIR mediated upconversion nanomaterials. Furthermore, the enhanced visible emission intensity demonstrated the composition's functional utility in the form a simple turn on sensor, capable of detecting dopamine in low pM concentrations. Hence, together with the enhanced luminescent property, the novel "sandwich" structured composition has great potential in not only bio-sensing applications but also broader applications of materials science and biological studies.

Example II

A. Introduction

Stem cell fate, function and plasticity are dynamically regulated in a spatiotemporally controlled manner by multiple cues including biomolecules and physical signals. Understanding the spatiotemporal functions of specific signals and further achieving precise control of stem cell behaviors in both spatially and temporally controlled manner are of great significance for studying physiological mechanisms, identifying pathogenic pathways, and developing stem cell-based treatments for devastating diseases. For instance, neurogenesis is a complicated biological process including several key stem cell behaviors such as adhesion, proliferation, differentiation, migration, axonal growth and synapse formation. To investigate as well as further regulate the complex process of neurogenesis, light, especially in the near-infrared (NIR) region, is an ideal stimulus for probing and modulating the spatiotemporal dynamics of signals in living cells and organisms with high resolution. For example, the optogenetic research method has provided several interesting demonstrations of light-controlled genome editing and gene activation. Other interesting approaches include utilizing photo-caged and photo-switching molecules for light-dependent biological regulations. In this regard, photo-responsive nanomaterials have gained increasing scientific interests in achieving cell behavior control attributed to their exceptional photo-physical properties. Photo-switching nanomaterial constructs, which display reversible chemical and structural properties, have specifically been incorporated into functional biological machinery to manipulate protein functionalities, dissecting molecular biological pathways, as well as modulating cellular behaviors. However, current approaches as well as applications of light-mediated biological manipulation are heavily dependent on ultraviolet and visible (UV-Vis) light as the main excitation source, which is intrinsically limited by its phototoxicity, low tissue penetration depth due to phenomena including light scattering and tissue absorption.

The disclosed technology concerns compositions that convert long wavelength NIR light into UV-Vis emissions, in a process known as photon upconversion. Based on this phenomenon, constructing an upconversion nanoparticle (UCNP)-based NIR controlled small molecule release system is a useful approach with significantly reduced phototoxicity and better tissue penetration capability than systems using UV-Vis light. However, 980 nm NIR excitation light can cause a severe heating effect owing to water absorption at this wavelength, thereby incurring thermal cytotoxicity. Accordingly, there is a need for a UCNP system that uses a different excitation light, such as 808 nm that does not produce the significant heating effect in water.

Disclosed herein are embodiments of the disclosed technology that use neodymium (Nd) and ytterbium (Yb) co-sensitized UCNPs that are demonstrated to have an 808 nm sensitization capability, and a minimal heating effect. Moreover, compared to conventional 980 nm excitation, 808 nm excitation demonstrates at least 50% deeper tissue penetration depth [about 2.0 cm (980 nm) vs. about 3.4 cm (808 nm)]. Nevertheless, a major challenge for utilizing 808 nm-excitation-UCNPs for bio-applications falls on the detrimental cross-relaxation from activator dopants to co-sensitizer ($Nd^{3+}$), leading to lower overall emission output as well as a lower UV emission ratio. The disclosed strategy to overcome this limitation utilized the core-shell structure to separate the $Nd^{3+}$ from the activators.

Additionally, disclosed embodiments can generate intense UV emissions sufficient to trigger the isomerization of a photo-switching capping system, such as the exemplary poly-spiropyran (pSP) moieties. Certain embodiments of the disclosed 808 nm-excited UCNP construct were designed with a multi-shell structure suitable for 808 nm to UV upconversion. Subsequently, this UCNP construct was coated with a mesoporous silica shell (UCNP@mSi) suitable for use as a small molecule reservoir, and further functionalized with a photo-responsive polymeric shell containing spiropyran groups (UCNP@mSi@pSP). In conjunction with the UCNP@mSi@pSP system, a neurogenic differentiation factor named retinoic acid (RA), which is highly involved in various developmental processes including neurogenesis, was delivered to human induced pluripotent stem cell-derived neural stem cells (hiPSC-NSCs) to promote neuronal differentiation in a spatiotemporally controlled manner. Human-induced pluripotent stem cells (hiPSCs) can be generated from patients with neurodegenerative diseases to present the mechanistic profiles during patient genotypic and phenotypic changes associated with neurological disorders. Therefore, hiPSC-NSCs provides an excellent platform that closely mimics the human brain and central nervous system (CNS) for disease modeling and drug screening. For example, studying the differentiation of hiPSC-NSCs into neural cell lineages and mature neural networks could provide insights into developmental biology as well as the detailed progression of neurodegenerative diseases. While RA was used as a proof-of-concept (POC) small molecule for neuronal differentiation, other differentiation factors can easily be incorporated into the UCNP@mSi@pSP platform to regulate a broad range of stem cell lineage commitments as well. Thus, the disclosed 808 nm NIR-mediated spatiotemporal stem cell fate control method can be easily extended to a variety of potential applications in stem cell therapy, neuroscience, and regenerative medicine.

B. Materials

Lanthanide chloride hexahydrates (>99.9%) were purchased from Sigma Aldrich and Treibacher Industrie AG. Oleic acid and 1-octadecene (both technical grade, 90%) were obtained from Alfa Aesar. Ammonium fluoride, 2-bromoisobutyryl bromide (BiBB), CuCl, dimethyl sulfoxide (DMSO), dichloromethane (DCM), methanol, N, N-dimethylformamide (DMF), 2,3,3-trimethyl-3H-indole, 1-iodopropane and 2-hydroxy-5-nitrobenzaldehyde, tetraethyl orthosilicate (TEOS), (3-Aminopropyl)triethoxysilane (APTES), N-cetyltrimethylammonium bromide (CTAB), paraformaldehyde, 1,1,4,7,10,10-Hexamethyltriethylenetetramine (HMTETA), sodium hydroxide (NaOH), methacryloyl chloride, tert-Butyl acrylate (tBA), trifluoroacetic acid (TFA), tetraethylorthosilicate (TEOS), N-hydroxysuccinimide (NHS), N-(3-Dimethylaminopropyl)-N'-ethylcarbodiimide hydrochloride (EDC HCl) were purchased from Sigma-Aldrich. Ethyl Acetate were purchased from Fisher Scientific. 1-(2-Hydroxyethyl)-3,3-dimethyl-6-nitrospiro(2H-1-benzopyran-2,2-indoline) (SP—OH) was purchased from TCI America. Sylgard 184 was purchased from Ellsworth Adhesive. All chemicals were used as received, without any further purification. Solvents for NMR analysis (Cambridge Isotope Laboratories) were used as received.

C. Material Characterizations

Transmission electron microscopy (TEM) was implemented with a 120 kV Philips CM12 (www.fei.com) microscope. A Malvern Zetasizer was used for dynamic light scattering (DLS). X-ray powder diffraction (XRD) patterns with a resolution of 0.005° (2θ) were collected using a Huber Guinier G670 diffractometer (www.xhuber.com) with a Cu source (Kα radiation, λ=1.54060 Å) operating at 40 kV and 30 mA. For the determination of the composition and concentration of the UCNPs a flame-EOP inductively coupled plasma optical emission spectrometer (ICP-OES) from Spectro (www.spectro.com) was used. Luminescence spectra of UCNPs were measured with an Aminco Bowman Series 2 luminescence spectrometer (Thermo Electron Corporation). The spectrometer was equipped with an external continuous wave 808 nm laser module (300 mW, ~15 mW cm$^{-2}$), obtained from Picotronic. The luminescence lifetime was measured by a homemade lifetime measurement setup consisting of 808 nm laser cw laser module (200 mW, ~15 mW cm$^{-2}$), optical chopper, temperature-controlled cuvette holder with integrated magnetic stirrer, collection lens filter wheel and mount for optical fiber. UV-vis absorption spectra were recorded on a Varian Cary 50 spectrophotometer. Fluorescence spectra were record on a Varian Cary Eclipse fluorescence spectrophotometer with external NIR lasers with a wavelength at 808 nm or 980 nm as excitation light source (CNI high power fiber coupled diode laser system, FC-W-980 and FC-W-808). The total output powers for the lasers are tunable from 1 mW to 10 W. The power density was detected by 1916-R handheld optical power meter with 818P thermophile detector (purchased from Newport corporation, USA) Unless otherwise stated, all spectra were obtained from hexane dispersion of nanoparticles (1 wt %). Fluorescence emission decays of UCNPs were collected on an Edinburgh FLS920 fluorescence spectrometer with an external continuous 980 nm NIR LED laser diode (1.5 W), which was coupled with a chopper to modulate the excitation into pulse mode. $^1$H NMR was acquired on Varian 300 MHz NMR spectrometer.

Example II-1

Synthesis of core particles β-NaYF$_4$: m % Yb, 0.3% Tm: For the synthesis of 1 mmol β-NaYF$_4$: m % Yb, 0.3% Tm particles with specific dopants molar ratio, corresponding molar ratios of the lanthanide chlorides were dissolved in methanol (5 mL) and transferred into a 50 ml three neck round bottom flask. Under nitrogen flow, oleic acid (8 mL) and 1-octadecene (15 mL) was added into the 50 mL three necked round bottom flask. This solution was then heated to 160° C. and put under vacuum for 30 minutes to reach a clear solution. The solution was cooled down to room temperature. Subsequently, a 10 mL methanol solution of 4 mmol NH$_4$F and 2.5 mmol NaOH were added into the flask and the suspension was kept at 120° C. for 30 minutes before heating to reflux (about 320° C.). The heating-time was controlled by the appearance of upconversion luminescence from the synthesis flask via illumination with a 980 nm cw laser (200 mW). As soon as the upconversion luminescence could be seen by eye, the solution was kept at reflux for additional 8 minutes. To obtain the fully transformation of the nanocrystals from the α- to the β-phase, a heating time of 15 minutes was adopted. The particles were precipitated by the addition of excess of ethanol and collected by centrifugation at 1,000 g for 5 minutes. The precipitate was washed with chloroform/ethanol (1:10 v/v) two times and five times with cyclohexane/acetone (1:10 v/v) by repeated redispersion-precipitation-centrifugation cycles. To remove aggregates, the particles were dispersed in 10 mL cyclohexane, centrifuged at 1,000 g for 3 minutes and the supernatant was collected.

Example II-2

Synthesis of core-shell β-NaYF$_4$: m % Yb, 0.3% Tm @NaYF$_4$: n % Yb, n % Nd and core-shell-shell β-NaYF$_4$: m % Yb, 0.3% Tm @NaYF$_4$: n % Yb, n % Nd @NaYF$_4$: The synthesis of shell-precursor material α-NaYF$_4$: n % Yb, n % Nd was performed by a method similar to the synthesis of β-NaYF$_4$: m % Yb, 0.3% Tm particles in Example II-1, except for the composition of the lanthanide chlorides and the last heating step under reflux (320° C.). In the present method, the solution was kept at 240° C. for 30 minutes to obtain the cubic crystal lattice. The synthesized shell-precursors were collected following similar procedures as described in Example I-1. The as-synthesized core UCNP β-NaYF$_4$: m % Yb, 0.3% Tm was transferred into 50 mL three necked round bottom flasks under N$_2$. Per 1 mmol total content of UCNP core particles, 5 mL oleic acid and 5 mL 1-octadecene were added. The flask was heated to 100° C. under vacuum for 1 hour to obtain a clear solution. After this, the β-NaYF$_4$ particles were heated to reflux at 320° C. The shell precursor α-NaYF$_4$: n % Yb, n % Nd was dispersed into 1 ml oleic acid/1-octadecene mixture (½ v/v). The shell precursor was quickly injected into the reaction flask. The reaction temperature dropped to about 300° C. The solution was kept for another 10 minutes at reflux. Then the solution was cooled down to room temperature. The same protocol was used for growing a second inert shell of NaYF$_4$ around the β-NaYF$_4$:25% Yb, 0.3% Tm@NaYF$_4$: 10% Yb, 10% Nd particles. The precipitation and purification of the synthesized nanoparticles was performed as previously described.

Example II-3

Mesoporous Silica Shell Coating: 15 mg of synthesized NaYF$_4$:25% Yb, 0.3% Tm@NaYF$_4$:10% Yb, 10% Nd @NaYF$_4$ in cyclohexane (600 μl) were mixed with CTAB solution (25 mL, 500 mg). The mixture solution was sonicated for 30 minutes by a probe sonicator, resulting in a transparent solution. Thereafter, the mixture solution was transferred to a dry 100 ml round bottom flask with addition of 150 μl 2M NaOH aqueous solution. The mixture was stirred at 60° C. for 30 minutes followed by 50 μl TEOS in 1.5 ml ethyl acetate addition in a drop-wise manner. The mixture was allowed for further stirring at 60° C. for 24 hours. Further amine functional group functionalization was achieved via grafting with (3-aminopropyl)triethoxysilane. 6.3 μl of (3-aminopropyl)triethoxysilane was added in to the reaction vessel and allowed to react for 8 hours. The final amine functionalized mesoporous silica coated UCNPs (UCNP@MSN-NH$_2$) were collected by centrifugation (6000 rpm) and washed with water 3 times.

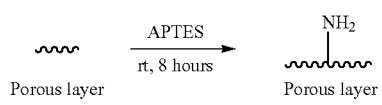

Example 1-4

Spiropyran Polymer Coating Through Atomic Transfer Radical Polymerization

Synthesis of UCNP@MSN-Br Initiator

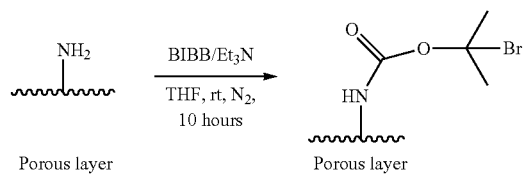

A mixture containing UCNP@MSN-NH$_2$ (0.8745 g, 1 mmol), Et$_3$N (0.1518 g, 1.5 mmol), and dry THF (15 mL) was cooled to 0° C. under N$_2$ atmosphere. BiBB (0.2759 g, 1.2 mmol) in dry THF (10 mL) was then added dropwise over 0.5 hour. The mixture was magnetically stirred for 10 hour at room temperature. After the reaction was completed, the mixture was filtered and evaporated by a rotary evaporator. CH$_2$Cl$_2$ (100 mL) was added, and the reaction mixture was washed three times with distilled water (10 mL×3).

Synthesis of Spiropyran Methacrylate Monomer (SPMA)

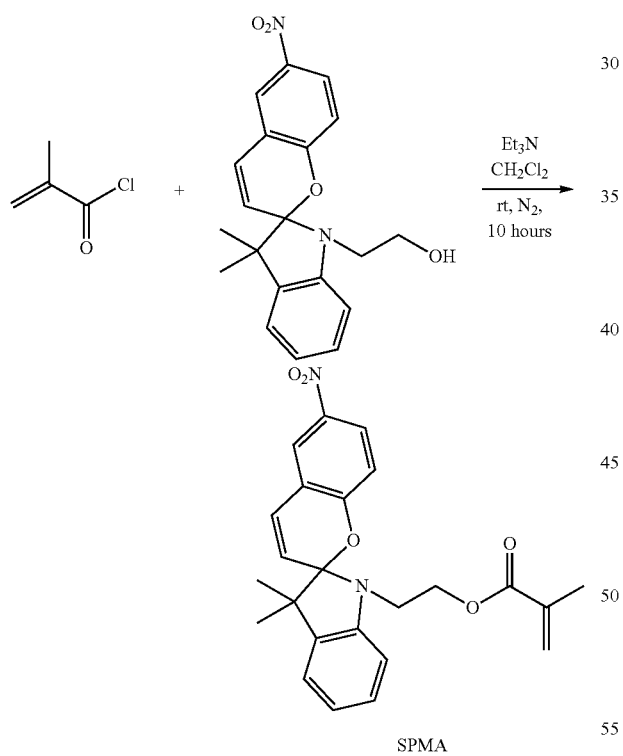

SPMA

A mixture containing 1-(2-hydroxyethyl)-3,3-dimethyl-6-nitrospiro(2H-1-benzopyran-2,2-indoline) (SP—OH) (1 g, 2.84 mmol), Et$_3$N (1.44 mL, 9.94 mmol), and dry CH$_2$Cl$_2$ (15 mL) was cooled to 0° C. under N$_2$ atmosphere and protection against visible light exposure. Methacryloyl chloride (0.83 mL, 8.52 mmol) in dry CH$_2$Cl$_2$ (5 mL) was then added dropwise over 0.5 hours. After stirring for 10 hours at room temperature, the solvent was removed by a rotary evaporator. The residue was purified by silica gel column chromatography (100-200 mesh).

Surface Initiated Atomic Transfer Radical Polymerization (ATRP)

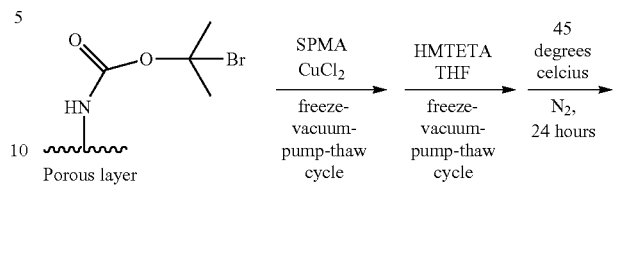

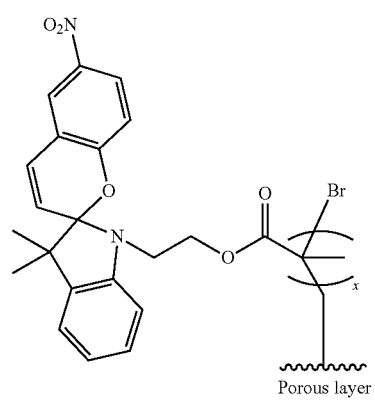

Polymer coated UCNP was synthesized via ATRP using UCNP@MSN-Br as an initiator. A typical polymerization procedure was as follows: a 50 mL flask, connected to a standard Schlenkline system with highly pure nitrogen, was charged with UCNP@MSN-Br (0.0244 g, 0.0238 mmol), SPMA (0.2 g, 0.4757 mmol), and CuCl (0.0024 g, 0.0238 mmol). Three exhausting-refilling nitrogen cycles were performed to remove oxygen from the system. Then HMTETA (0.0066 g, 0.0285 mmol), THF (3 mL), and methanol (1 mL) were injected into the flask using a syringe, followed by three freeze-vacuum-pump-thaw cycles to remove oxygen from the solution. The flask was sealed under a nitrogen atmosphere and kept in an oil-bath at 45° C. The polymerization was carried out for 24 hours.

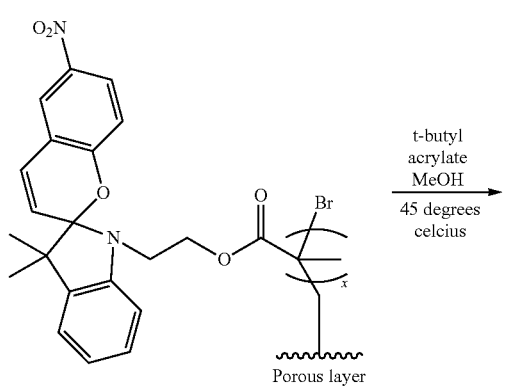

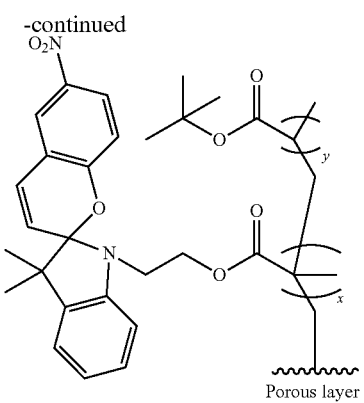

Subsequently, a solution of tBA (0.0067 g, 0.476 mmol) in 1 ml methanol was injected into the reaction vessal. The reaction was allowed to react for 12 hours at 45° C. The reaction was terminated by letting oxygen into the system. Hydrolysis of the Poly (t-Butyl Acrylate) Blocks

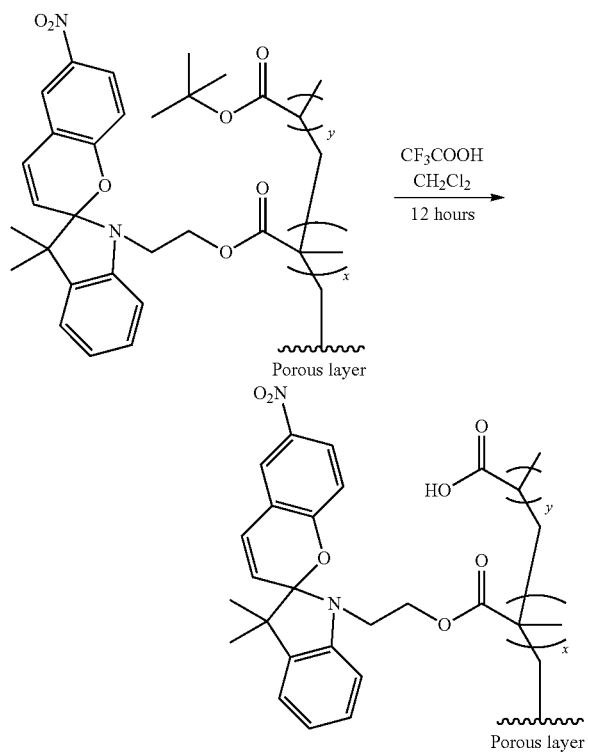

The reaction solvent was removed through rotavapor. The polymer coated nano-constructs were re-dissolved in CH$_2$Cl$_2$. And a five-fold molar excess of CF$_3$COOH was added to induce the hydrolysis. The reaction mixture was stirred at room temperature for 12 hours. The reaction solvent was removed through centrifugation (7000 rpm, 10 minutes). The resultant nanoparticle constructs were washed with CH$_2$Cl$_2$ and water for 4 times respectively.

Example II-5 hiPSC-NSC Culture: Tissue culture vessels were coated with Matrigel (Corning) 1:200 dilution with DMEM (Invitrogen) at 37° C. for 1 hour. hiPSC-NPCs were derived from hiPSCs (WT126 clone 8; and WT33 clone 1). iPSC-NPCs were expanded in a proliferation media containing DMEM/F12 with Glutamax (Invitrogen), B27-supplement w/o Vitamin A (Invitrogen), N2 (Stem Cells), and 20 ng/ml FGF2 (Invitrogen). Fresh media was exchanged every other day.

Example II-6

Cell Viability Characterization: Cell viability assays were conducted in 96-well plates coated with Matrigel (Corning) 1:200 dilution with DMEM (Invitrogen) at 37° C. for 1 hour. 20k of human induced pluripotent stem cell derived neural stem cell (hiPSC-NSCs) in 100 μL growth medium were seeded into each well. For nanoparticle concentration-dependent viability, increasing nanoparticle concentrations (0 mg/ml to 200 mg/ml) were added into well plate for 24 hour incubation. Subsequently, a resazurin-based viability reagent: PrestoBlue™ was introduced into each well with 30-minute incubation. Fluorescence intensity was determined through microplate reader at 590 nm emission with 530 nm excitation. For NIR intensity-based viability, increasing 808 nm laser power density (0 W/cm$^2$ to 8.42 W/cm$^2$) with irradiation diameter (6 mm) were applied to each well. The well plate was store in incubator for 24 hours followed by PrestoBlue™ based viability assay as described above.

Example II-7

808 nm NIR-mediated hiPSC-NSC Differentiation: 808 nm NIR-mediated hiPSC-NSC differentiation experiments were conducted in 48-well plates. The 48-well plate was coated with Matrigel (Corning) 1:200 dilution with DMEM (Invitrogen) at 37° C. for 1 hour. 30 k of human induced pluripotent stem cell derived neural stem cell (hiPSC-NSCs) in 200 μL growth media were seeded into each well.

A nanoparticle constructs solution was prepared by exposing the nanoparticles to 2 μM retinoic acid (RA) solution in DMSO. The mixture was then exposed to UV light for a time period suitable to open the capping moiety, such as 365 nm UV light for about 60 seconds, and mixed for about 60 seconds. After mixing, the mixture was exposed to green light, at a wavelength and for a time period suitable to close the capping moiety, such as light at a wavelength of 543 nm, and for about 90 seconds, to form the nanoparticle constructs solution.

After 24 hours with cell attachment on the culture plate, the culture media were changed to the nanoparticle constructs solution. After 8 hour of nanoparticle incubation, a NIR illumination with 1.05 W/cm$^2$ power density was utilized to trigger the uncapping and release of neurogenic factor (RA) (3×5 minute illumination with 5 minute interval).

Example II-8

3×3 iPSC-NSCs 2D Colony Culture and Formation: 3×3 PDMS hole array fabrication. A well-mixed PDMS pre-polymer (Sylgard 184, A and B in 15 to 1 ratio respectively) was poured into Petri dish to give a 2-mm-thick PDMS layer followed by curing in an 80° C. oven overnight. Subsequently, the PDMS layer was cut into 15 mm×15 mm squares. A 3×3-hole array was generated using 3 mm diameter puncher.

3×3 iPSC-NSCs 2D colony culture and formation. 12-well cell culture plate was first coated with Matrigel (Corning) dissolved in DMEM/F12 (Gibco) (1:200) in the incubator for 1 hour. With aspiration of the coating media, the PDMS 3×3-hole array mold (ethanol washed) was placed into well. hiPSC-NPCs media suspension (1 million/ml) was added into each well (3 µl/hole). The seeded culture plate with PDMS mold was carefully located into incubate to allow cell attachment for 2 hours. The PDMS mold was removed with tweezers. The culture well was filled with 1 ml culture media for prolonged culture to form hiPSC-NPCs colony pattern.

Example II-9

Immunohistochemistry: Cells were washed twice with DPBS (pH 7.4) and treated with 4% formaldehyde solution for fixation for 20 minutes, followed by DPBS wash three times. Subsequently, the cells were permeabilized and blocked for non-specific binding with blocking buffer containing 0.1% Triton X-100 and 5% normal goat serum (NGS, Life Technologies) in PBS for 1 hour. To characterize the extent of neuronal differentiation, the cells were fixed, blocked and stained with a primary mouse antibody against TUJ1 (1:500 dilution, Cell Signaling). Specifically, the fixed samples were incubated 2.5 hours at 4° C. in an anti-body dilution buffer (PBS containing 10% NGS) with TUJ1 primary antibody. With 3 times PBS washing, the cells were incubated for 1 hour at room temperature in antibody dilution buffer containing Hoeschst (3 g/mL, Life Technologies) and anti-mouse secondary antibody labeled with Alexa Flour 594 (1:500, Life Technologies). Followed by 3-time PBS washing, all the sample were imaged using Nikon T2500 inverted fluorescence microscope. For mature neuronal markers (MAP2 and Synapsin) characterization, primary rabbit antibody against MAP2 (Cell Signaling) and Synapsin (EMD Millipore) were used at 1:500 dilution. Subsequently, anti-rabbit secondary antibody Alexa Fluor 488 (1:500, Life Technologies) was utilized to visualize the mature neuronal markers using Nikon T2500 inverted fluorescence microscope.

Example II-10

Gene Expression Analysis: The expression level of target genes was quantified by quantitative reverse transcription PCR (RT-qPCR) of mRNA extracted from tissue culture. The total RNA, including mRNA of interest, was extracted using TRIzol Reagent (Life Technologies). The total RNA (1 µg) was used as template for a reverse transcription reaction to generate the first-strand complementary DNA (cDNA) using the Superscript III First-Strand Synthesis System (Life Technologies), following the manufacturer's protocol. The first-strand cDNA was subsequently used for qPCR reaction with gene-specific primers in the presence of Power SYBR Green PCR Master Mix (Applied Biosystems) on a StepOnePlus Real-Time PCR System (Applied Biosystems). The resulting $C_t$ values were normalized to endogenous control (GAPDH). The Standard cycling conditions were used for all reactions with a melting temperature of 60° C. All gene-specific primers were obtained from the PrimerBank database and listed in Table 2.

TABLE 2

The primer sequences for the genes which are analyzed in this study through RT-qPCR.

| Gene | Forward Primer (5' to 3') (SEQ ID NO:) | Reverse Primer (3' to 5') (SEQ ID NO:) |
|---|---|---|
| GAPDH | CCGCATCTTCTTTTGCGTCG (2) | GCCCAATACGACCAAATCCGT (3) |
| TUJ1 | GGTGTCCGAGTACCAGCAGT (4) | TTCGTACATCTCGCCCTCTT (5) |

Example II-11

Calcium Imaging: Differentiated neurons were incubated with 5 µM Fluo-4-AM (Life Technologies) media for 30 minutes. Subsequently, the treated cells were washed with HBSS (Life Technologies) and incubated for 30 minutes in culture media for de-esterification process of the dye. Media was changed to HBSS for initiation of the calcium imaging session. Under the movie mode of Nikon Eclipse Ti-E microscope, concentrated KCl solution in PBS (50 mM, 0.1 ml) was added to the cells, and the movie was taken for 10 minutes with 60 frames per seconds.

Example II-12

Results and Discussion

Figure 30:
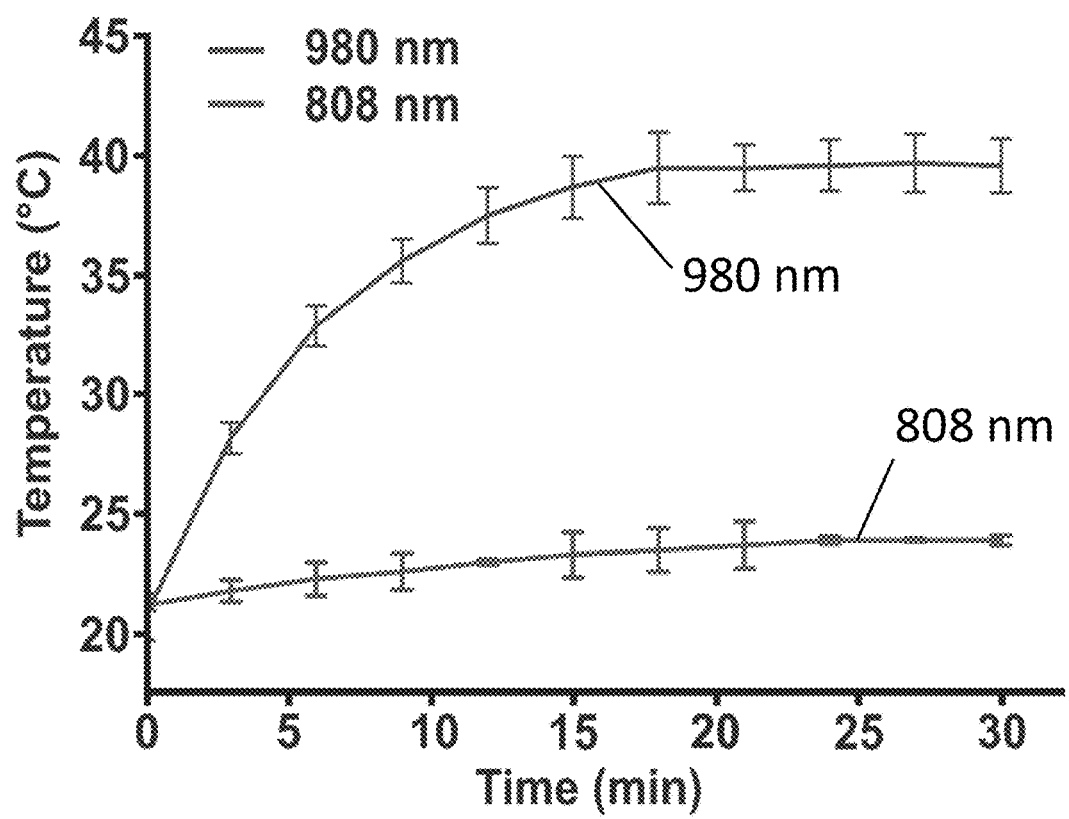
FIG. 30 is a graph of temperature versus time, illustrating the heating effects of exposing colloidally stable aqueous solution of core-shell UCNPs $NaYF_4$:25% Yb, 0.3% Tm @$NaYF_4$:10% Yb, 10% Nd @PAA to 980 nm and 808 nm lasers.
Figure 31:
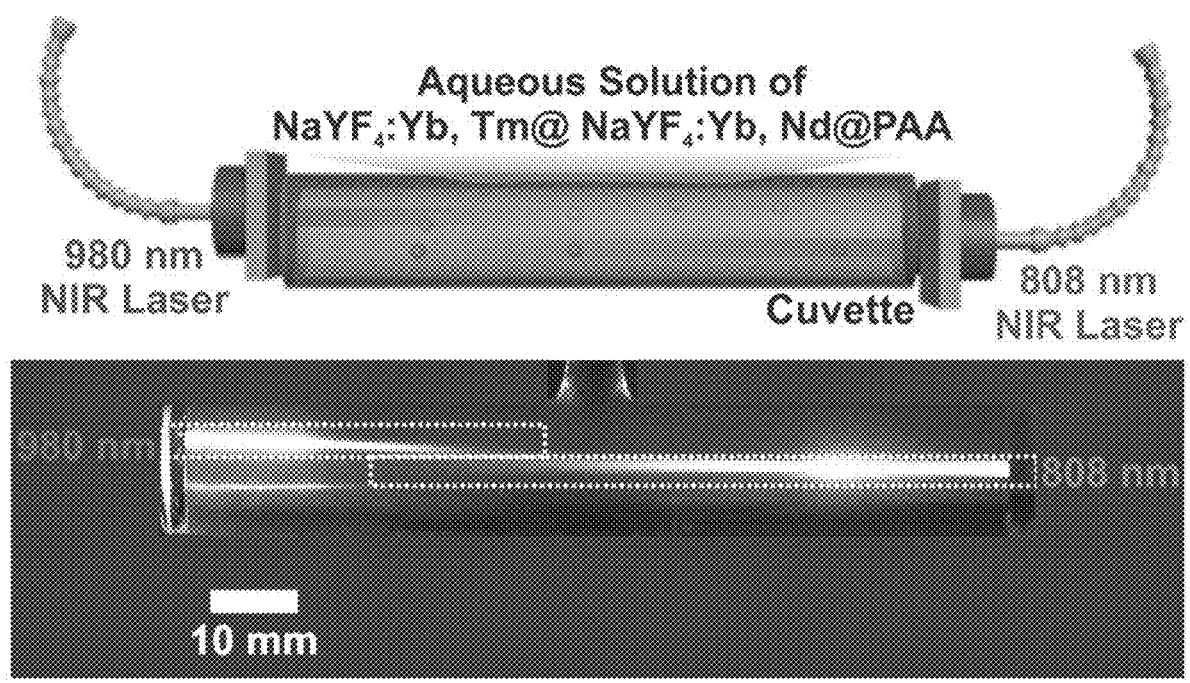
FIG. 31 provides digital images illustrating the penetration depth comparison using a 10 cm glass tube filled with an aqueous dispersion (2 mg/mL) of core-shell UCNPs $NaYF_4$:25% Yb, 0.3% Tm@$NaYF_4$:10% Yb, 10 Nd@PAA and illuminated by 980 nm (left) and 808 nm (right) lasers.

Maximizing tissue penetration depth and minimizing heating effect by developing 808 nm-excited UCNPs: Before examining the photoluminescent properties of the synthesized UCNPs and the capability of UCNP@mSi@pSP to control stem cell differentiation, the usefulness of Nd-facilitated 808 nm excitation was demonstrated for this particular application, compared to that of Yb-mediated 980 nm excitation. It is known that both 808 nm and 980 nm NIR fall into NIR-I region of 700 nm-1000 nm, while only the 808 nm NIR locates into the first biological optical window (640 nm-960 nm). As a result, Nd-mediated 808 nm upconversion may be more suitable than 980 nm upconversion systems for certain applications in aqueous and biological environments because of the reduced heating effect (FIG. 30) as well as increased penetration depth (FIG. 31). Without being bound to a particular theory, these effects may be due, at least in part, to $Nd^{3+}$ ions having a 10-times higher absorption cross-section of about $10^{-19}$ $cm^2$ compared to $Yb^{3+}$, and because water shows a significantly lower absorption for 808 nm light compared to 980 nm. Consequently, since both absorption and scattering dictate light-tissue interaction, 808 nm excitation possesses a deeper tissue-penetration capability, which is favorable for certain in vitro/in vivo therapeutic applications. For example, a 10 cm glass cuvette containing a 2 mg/ml aqueous solution of $NaYF_4$:25% Yb, 0.3% Tm@$NaYF_4$; 10% Nd, 10% Yb@$NaYF_4$@PAA UCNPs was irradiated with 980 nm laser (left) and 808 nm laser (right) under same power density. The 808 nm excitation showed a 6.6 cm penetration depth comparing to 980 nm excitation, which only showed a 3.7 cm penetration (FIG. 31).

Figure 32:
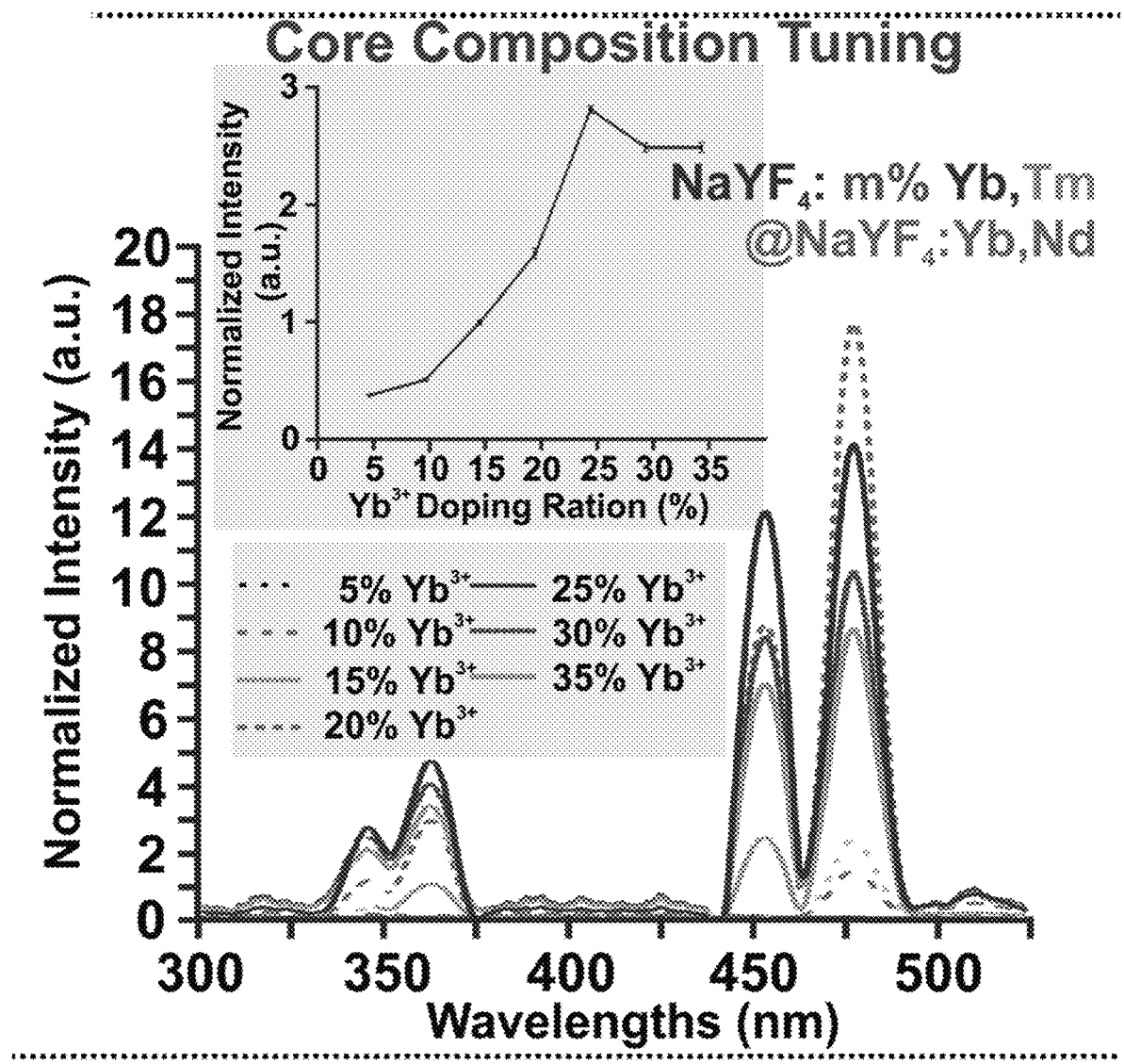
FIG. 32 is a graph of normalized intensity versus wavelength illustrating the relative upconversion luminescence of different sensitizer ($Yb^{3+}$) concentrations in the core (0-35 mol %), with an insert illustrating the quantitative comparison of UV emission (368 nm) peak intensity of different $Yb^{3+}$ concentrations.
Figure 33:
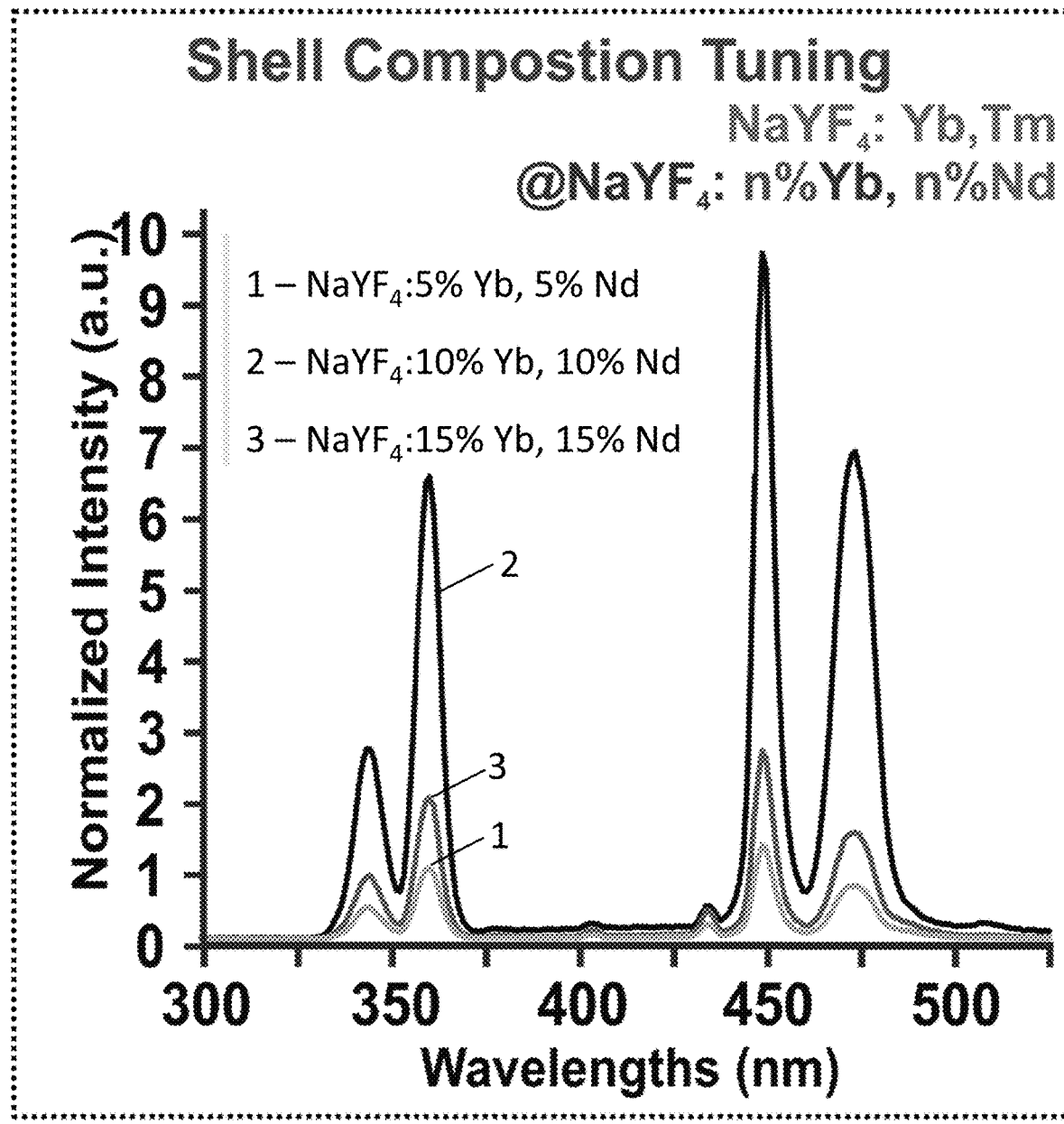
FIG. 33 is a graph of normalized intensity versus wavelength illustrating the relative upconversion luminescence of different co-sensitizers' ($Nd^{3+}$ and $Yb^{3+}$) concentrations in the sensitizing shell.

Achieving a highly efficient UV emission by designing core-shell structured 808 nm UCNPs: To achieve efficient 808 nm NIR to UV/Vis upconversion suitable for use in a photo-switching application, such as in the disclosed pSP capping system, core-shell-shell UCNPs were designed and synthesized that possessed 1) tandem-sensitization from $Nd^{3+}/Yb^{3+}$ to $Yb^{3+}/Tm^{3+}$ dopants, and 2) cross-relaxation mitigation by spatial separation of $Tm^{3+}$ and $Nd^{3+}$ into the nanoparticle core and shell respectively. $NaYF_4$ was selected as a host material due to its low lattice phonon energy of 350 $cm^{-1}$. The disclosed core-shell-shell design comprised a $NaYF_4$: Yb/Tm core and two outer shells with different functions: the first shell located on the core ($NaYF_4$: Yb/Nd) as an 808 nm photon-absorbing layer, and the second shell as inert coating ($NaYF_4$) on top of the first shell, thereby protecting against surface quenching. Core-shell UCNPs ($NaYF_4$: m % Yb, 0.3% Tm@$NaYF_4$; 10% Nd, 10% Yb) with variations in core $Yb^{3+}$ doping ratio of from 5-35% and fixed shell composition ($NaYF_4$; 10% Nd, 10% Yb) were synthesized and tested for efficient UV upconversion. Detailed luminescence characterization regarding size and doping-ratio of the core and shells were performed to assess efficiency for UV emissions suitable to trigger the release of the small molecule in the following studies. The data suggested that the highest emission at 345 nm ($^1I_6 \rightarrow ^3F_4$ transition) and 368 nm ($^1D_2 \rightarrow ^3H_6$ transition) upon 808 nm excitation was obtained by a doping ratio of 25% $Yb^{3+}$ and 0.3% $Tm^{3+}$ in the core according to luminescence (FIG. 32) and lifetime measurements (data not shown). The sensitizing shell composition was also investigated by varying the doping ratio of $Yb^{3+}$ (5-15%) and $Nd^{3+}$ (5-15%). The results indicated that 10% $Yb^{3+}$ and 10% $Nd^{3+}$ may provide a beneficial UV upconversion efficiency (FIG. 33).

A second shell was grown on the core-shell UCNPs ($NaYF_4$:25% Yb, 0.3% Tm @$NaYF_4$; 10% Nd, 10% Yb) to reduce surface defect-based quenching, which provided an additional 33% increase of the upconversion emission at 368 nm (data not shown). As a result, core-shell-shell UCNPs ($NaYF_4$:25% Yb, 0.3% Tm@$NaYF_4$; 10% Nd, 10% Yb@$NaYF_4$) with enhanced 808 nm-mediated UV emissions were obtained. The developed 808 nm sensitizing core-shell-shell UCNPs showed a higher efficiency for UV emissions, resulting in a peak ratio ($I_{368\,nm}/I_{475\,nm}$) of 0.53. The mono-dispersity of each nanoparticle structure through the synthetic steps of the core-shell-shell UCNPs was verified through TEM as well as dynamic light scattering (DLS) (data not shown). The crystallinity of each synthetic step was confirmed by XRD measurements to show a β-hexagonal phase. The final core-shell-shell UCNPs' dimensional information was determined by TEM and is provided in Table 3. Calculations and measurements using inductively coupled plasma optical emission spectrometry provided a nanoparticle composition of $NaYF_4$: 24.5% Yb, 0.27% Tm @$NaYF_4$: 9.9% Nd, 10.5% Yb@$NaYF_4$.

TABLE 3

Overview of the lanthanide contents in the core, core-shell and core-shell-shell nanoparticles determined by inductively coupled plasma optical emission spectroscopy (n = 3).

| theoretical composition | radius/ nm | lanthanide content [%] | | | |
|---|---|---|---|---|---|
| | | $Y^{3+}$ | $Tm^{3+}$ | $Yb^{3+}$ | $Nd^{3+}$ |
| core $NaYF_4$:25% Yb, 0.3% Tm | 12.65 | 75.5 ± 0.12 | 0.27 ± 0.01 | 24.46 ± 0.09 | |
| shell1 $NaYF_4$:10% Yb, 10% Nd | 4.15 | 79.6 ± 0.22 | | 10.48 ± 0.11 | 9.89 ± 0.07 |
| shell2 $NaYF_4$ | 1.80 | 101 ± 0.05 | | | |

Developing a photo-switching capping system by UCNP surface modification with poly-spiropyran (pSP): To efficiently deliver the neurogenic factor (RA), a mesoporous silica (mSi) layer was further coated on the disclosed UCNPs. With the mesoporous silica coating, the nanoparticle diameter reached about 83.7±3.9 nm. To synthesize the pSP-based shell, a photo-responsive monomer spiropyran methacrylate (SPMA) was prepared and confirmed through $H^1$-NMR. The pSP polymer shell containing spiropyran-based moieties was formed on the mesoporous silica shell (UCNP@mSi) through surface-initiated Atomic Transfer Radical Polymerization (ATRP). Due to the existence of active initiator sites on the poly-spiropyran, a colloidal stabilizing polymer layer (poly-acrylic acid) was further grafted onto the spiropyran polymer coated UCNPs. The resulting nanoparticles were characterized by TEM and FTIR. With the polymer coating, the final UCNP@mSi@pSP nanoparticle constructs possessed a diameter of 96.1±6.6 nm under TEM and a hydrodynamic size of 144 nm (polydispersity index (PDI=0.204) through dynamic light scattering (DLS) analysis.

Demonstrating spatiotemporally controlled release of small molecules using 808 NIR-mediated photo-switching UCNP@mSi@pSP: To assess the efficiency of the nanoparticle's cellular uptake and its ability to deliver the neurogenic factor (RA) in a spatiotemporally controlled manner, UCNP@mSi@pSP were loaded with RA and transfected into hiPSC-NSC. To improve the cellular uptake efficiency, Arg-Gly-Asp (RGD) peptides were conjugated onto the surface of UCNP@mSi@pSP, promoting transfection via RGD-mediated integrin binding to the cellular membrane receptors (e.g., $βv β_3$ and $αv β_5$) which further facilitates receptor-mediated endocytosis. $βv β_3$ and $αv β_5$ integrin subunits, which are well-known RGD binding receptors, are highly expressed during the neurogenic developmental process (neural tube). The RGD peptides were conjugated using EDC-NHS coupling. Briefly, 0.025 g UCNP@mSi@pSP was dispersed in PBS solution of EDC (1-ethyl-3-[3-dimethylaminopropyl]carbodiimide) (0.011 g) and NHS (N-hydroxysuccinimide) (0.016 g). The mixture was allowed to react for 1 hour. Subsequently, a PBS solution of peptide RGDSC (7 mg) was mixed with the nanoparticle solution and allowed to react for 3 hours. The conjugated nanoparticle constructs were collected though centrifugation and PBS wash 3 times.

Figure 35:
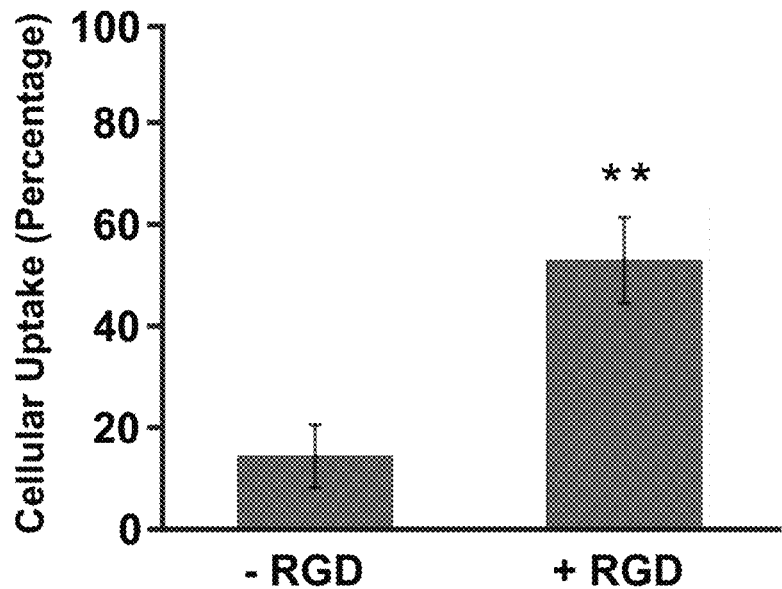
FIG. 35 is a graph of cellular uptake versus construct, illustrating the significant increase in uptake achieved by the RGD-labeled construct (+RGD), compared to the unlabeled construct (−RGD).

Upconversion luminescence (UCL) and fluorescence microscope images demonstrated that the ligand-targeted UCNP constructs' (RGD-modified UCNP@mSi@pSP) upconversion emissions significantly overlapped with the hiPSC-NSCs' cytoplasm, compared to non-specific UCNP constructs (non-RGD-modified UCNP@mSi@pSP) where little overlap was observed. And quantification of these results provided the percentage of hiPSC-NSCs with UCL positive signal demonstrated that significantly more (about 54%) RGD-modified UCNP@mSi@pSP taken up by hiPSC-NSCs, compared with the uptake of non-RGD-modified constructs (about 15%) (FIG. 35).

Figure 36:
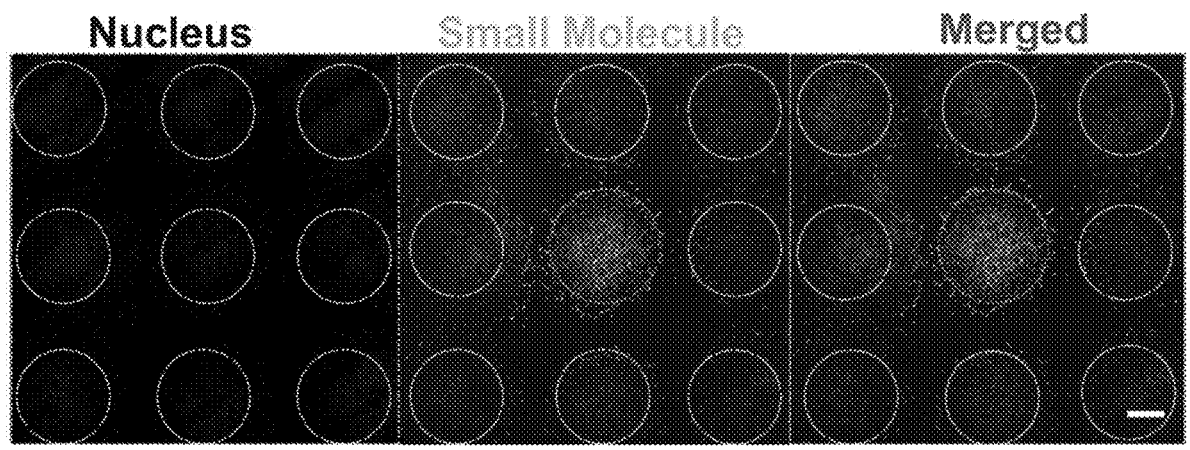
FIG. 36 is a digital image illustrating fluorescence microscopy characterization of fluorescein spatial controlled release in live hiPSC-NSCs colony culture and showing that only the center cell that was exposed to 808 nm light produced a fluorescence signal (scale bar: 1000 µm).

Meanwhile, the cell viability under 808 nm laser irradiation and transfection conditions were fully characterized for subsequent NIR-mediated neuronal differentiation experiments. A decreasing trend in hiPSC-NSC's viability was observed, as the power density of 808 nm laser was increased. For the NIR-mediated differentiation experimental conditions, a low power density (allowing for 90.75% cell viability) of 1.05 $W/cm^2$ was chosen. Minimal cytotoxicity was also observed from the nanoparticle constructs for concentrations up to 500 g/ml. The desired spatial and temporal controlled release capability was demonstrated using fluorescein as model molecule. Temporally controlled "on/off" release profile was demonstrated in FIG. 34, using the designed UCNP@mSi@pSP, triggered via 808 nm light. Specifically, an average of 4% of payload release was achieved within 5 minutes by 808 nm NIR illumination (1.05 W/cm$^2$). The merocyanine form reverts to the spiropyran form once the 808 nm excitation is removed, reforming a hydrophobic layer that blocks the release of small molecules, as shown in Scheme 1, above. The UCNP@mSi@pSP's ability of spatial small molecule release in response to 808 nm NIR stimulation has also been demonstrated. Specifically, to highlight the ability to spatially control small molecule release, a 3×3 colony array of hiPSC-NSCs was constructed using a PDMS mold, as shown in FIG. 36. The small molecule was locally released in the central colony where 808 nm NIR excitation was applied, illustrated by the green fluorescence signal emanating from the irradiated colony. These results showcase the UCNP@mSi@pSP-mediated small molecule releasing capability under 808 nm excitation within a 2D neural stem cell network in a spatiotemporal manner.

Figure 37:
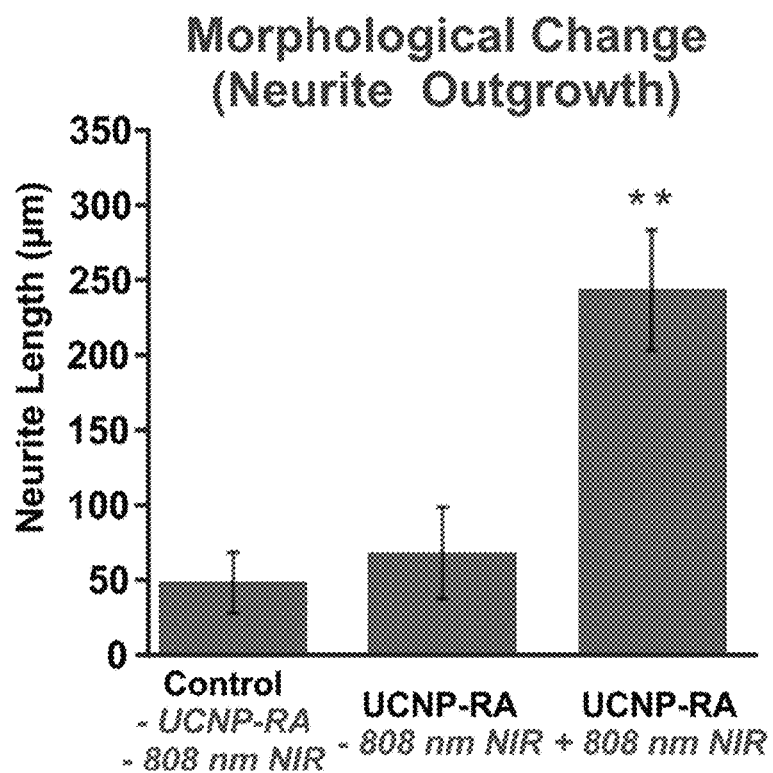
FIG. 37 is a graph of neurite length versus treatment group, illustrating the morphological changes (neurite growth) of the three treatment groups.
Figure 38:
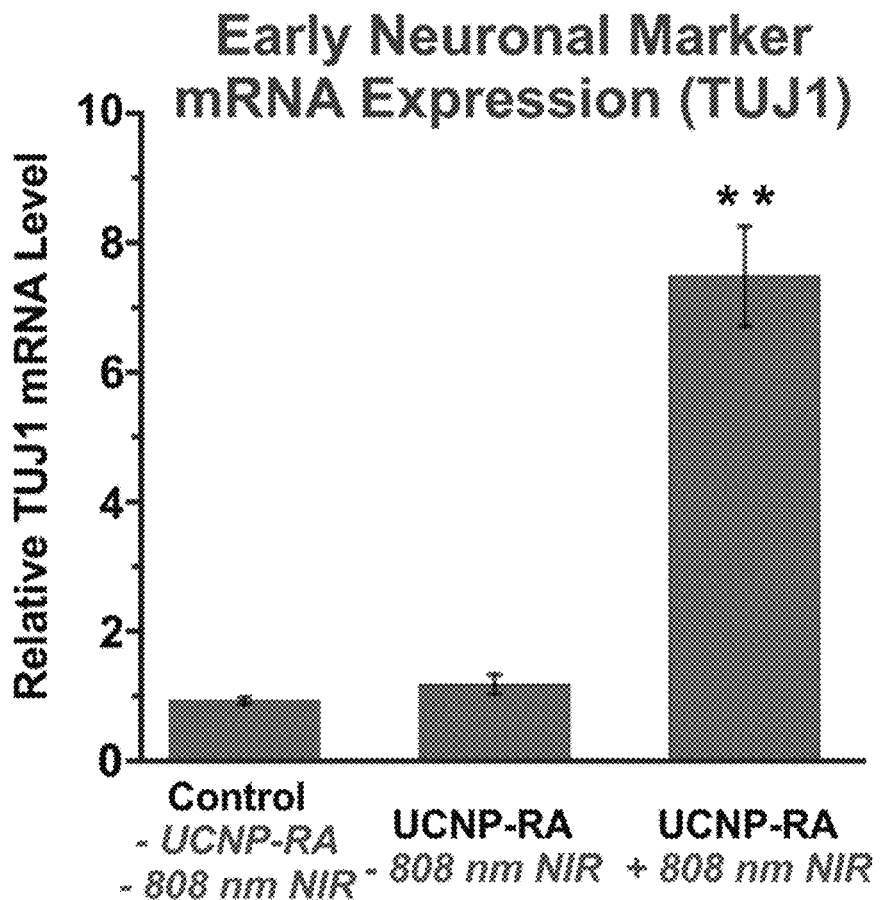
FIG. 38 is a graph of relative TUJ1 mRNA level versus treatment group, illustrating the gene expression observed using qPCR quantifying of the TUJ1 mRNA expression levels in hiPSC-NSCs in the three treatment groups.

Investigating 808 nm NIR-controlled hiPSC-NSC neuronal differentiation using neurogenic factor loaded UCNP@mSi@pSP: Recent advances in stem cell biology hold great potential for developing new approaches for the treatment of many devastating neuro-generative diseases and genetic disorders. Stem cell-based therapies for regenerating functional neurons and restoring neuronal functions to damaged CNS areas can be very beneficial for realizing stem cell therapy for neurodegenerative diseases. Such approaches, however, inevitably require the robust generation of engraftable cell sources of functional neural cells and better control of stem cell neuronal differentiation in a spatiotemporally controlled and safe manner. Thus, upon the construction of the small molecule delivery system, ability for the spatiotemporally controlled release of RA (a small molecule neurogenic factor) to induce neuronal differentiation of hiPSC-NSCs was evaluated under 808 nm excitation. hiPSC-NSCs were seeded and treated with RGD-modified UCNP@mSi@pSP containing RA molecules followed by 808 nm light exposure (1.05 W/cm$^2$) for 15 minutes (5-minute exposure intervals) prior to further culturing and characterization assays. After 5 days of stem cell culture, immunohistochemistry and qPCR analytical methods were performed to evaluate the hiPSC-NSCs neuronal differentiation. The control group and the nanoparticle constructs treated group (UCNP-RA) presented a significantly lower expression of early neuronal markers such as neuron-specific class III β-tubulin (TUJ1) compared with the group treated with 808 nm NIR and the UCNP constructs (UCNP-RA+808 nm NIR). Furthermore, a dramatic neuronal morphological change was observed from the "UCNP-RA+808 nm NIR" group compared to the control and "UCNP-RA" groups, demonstrating a typical neurite outgrowth morphology indicating neuronal lineage commitment (FIG. 37). Such neuronal morphological change was quantified by measuring neurite length according to the TUJ1 immunohistochemistry staining, with the "UCNP-RA+808 nm NIR" group showing significantly increased quantity and length of neurite outgrowths compared to the control and "UCNP-RA" groups (FIG. 37). Furthermore, this controlled neurogenesis process was corroborated with TUJ1 mRNA expression level through qPCR (FIG. 38), with a 7-fold TUJ1 upregulation in the "UCNP-RA+808 nm NIR" group compared to the control group. As a result, the neuronal differentiation from human neural stem cells (hiPSC-NSCs) was successfully controlled using the UCNP@mSi@pSP system in a NIR-mediated manner.

Figure 39:
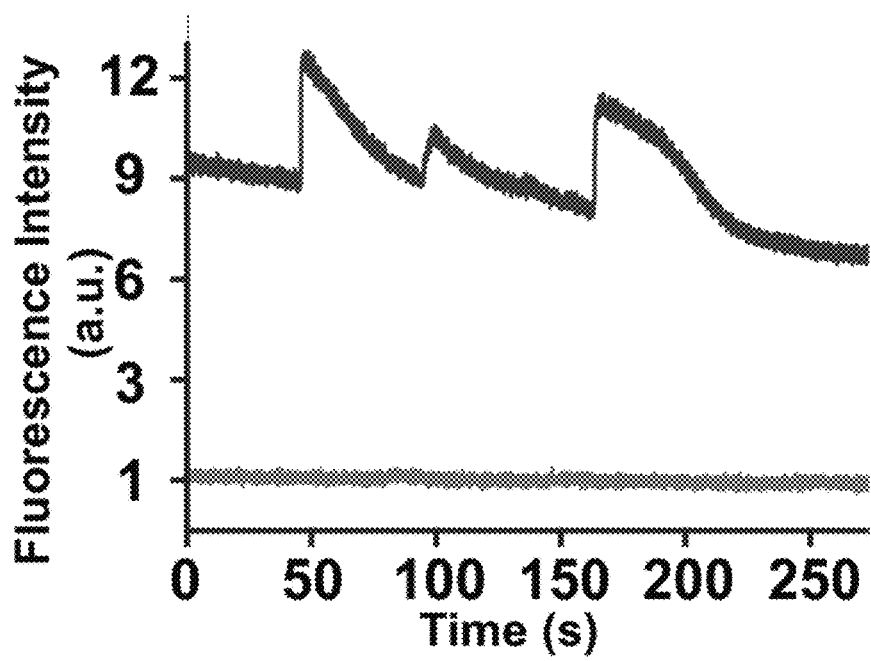
FIG. 39 is a graph of fluorescence intensity versus time, illustrating time traces for the fluorescence intensity change representing spontaneous calcium ion influx for an active neuron (dark grey line—top) and an inactive neuron (light grey line—bottom).

Confirming maturation and functionality of the hiPSC-NSC-derived neurons: To further evaluate the maturity and functionality of the differentiated neurons from hiPSC-NSCs, the experimental group was maintained under differentiation condition for up to 14 days for characterizing mature neuronal markers and functional activities. Immunohistochemistry results showed that the UCNP@mSi@pSP-based RA delivery system was a robust and effective method for the induction of mature neuronal differentiation in hiPSC-NSCs. Specifically, neuron-specific microtubule-associated proteins (MAP2), which is associated with nerve functions as well as neuronal cell structures, was found highly expressed in the differentiated neurons. Moreover, as an indicator of mature neuronal network synaptogenesis, Synapsin was selected and found highly expressed in the differentiated neurons. To characterize the differentiated neurons' functionality, calcium imaging was performed to test their response to potential differences. Functionally active neurons spontaneously fire action potentials that allow for the influx of cations including calcium. Using a commercially available calcium indicator dye, Fluo-4, changes in intracellular calcium concentrations were visualized. Furthermore, the fluorescence changes were quantified (FIG. 39) and observed for spontaneous fluctuations of calcium ions in active neuron over a 250 second period while the inactive control neuron did not show any changes in fluorescence intensity.

CONCLUSION

In summary, the first 808 nm to UV upconversion-mediated photo-switching nanosystem (UCNP@mSi@pSP) for NIR-based spatiotemporal stem cell fate control was demonstrated. The core-shell-shell structured UCNP design and synthesis enabled improvement in the UV upconversion luminescence significantly. Furthermore, the spiropyran-based gate-keeping system achieved small molecule release in a spatiotemporally controlled manner. The disclosed 808 nm NIR mediated photo-switching nanosystem can provide an innovative extension of nanotechnology to stem cell biology and neuro-regenerative medicine. Particularly, the application of NIR-mediated small molecule delivery to modulate key signaling pathways is important not only for selective stem cell fate control but also for dissecting signaling cascades affected by other stem cell microenvironments such as cell-cell interactions and biophysical/mechanical cues in vitro as well as in vivo.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A composition, comprising:

a first layer comprising a first substrate and a first dopant;

a second layer in direct physical contact with the first layer, the second layer comprising a second substrate and a second dopant; and a third layer in direct physical contact with the second layer and not in direct physical contact with the first layer, the third layer comprising a third substrate and optionally a third dopant;

wherein each of the first, second and third dopants, if present, independently comprises a lanthanide ion, NIR emitting dye, or a combination thereof, and the second dopant is different from the first and third dopants, if present; and wherein each of the first, second, and third dopants, if present, independently is either an emitter dopant or a sensitizer dopant, and the sensitizer and emitter dopants are in separate layers such that none of the first, second or third layers comprises both an emitter dopant and a sensitizer dopant.

2. The composition of claim 1, wherein each of the first, second and third substrate independently is selected from $NaYF_4$, $CaF_2$, $ZrO_2$, $YVO_4$, $Y_2O_2S$, $GdOCl$, $GdOF$, $Y_2O_3$, $NaPrF_4$, $NaPmF_4$, $NaSmF_4$, $NaEuF_4$, $NaGdF_4$, $NaTbF_4$, NaDyF$_4$, NaHoF$_4$, NaTmF$_4$, NaErF$_4$, NaCeF$_4$, NaNdF$_4$, NaLuF$_4$, NaYbF$_4$, or a combination thereof.

3. The composition of claim 1, wherein the first dopant is an emitter dopant and the second dopant is a sensitizer dopant.

4. The composition of claim 1, wherein the first dopant and the third dopant are sensitizer dopants, and the second dopant is an emitter dopant.

5. The composition of claim 3, wherein the third layer does not comprise the third dopant.

6. The composition of claim 1, wherein:
the sensitizer dopants are selected to absorb light having a wavelength of from 600 nm to 1300 nm;
the emitter dopant is selected to emit light having a wavelength of from 500 nm to 560 nm;
or a combination thereof.

7. The composition of claim 1, wherein:
each of the sensitizer dopants independently is a ytterbium ion, neodymium ion, an NIR emitting dye, or a combination thereof;
the emitter dopant is a praseodymium ion, promethium ion, samarium ion, europium ion, terbium ion, dysprosium ion, holmium ion, erbium ion, thulium ion, ytterbium ion, or a combination thereof;
or a combination thereof.

8. The composition of claim 1, wherein:
the first layer comprises from greater than zero to 50 mol % of the first dopant;
the second layer comprises from greater than zero to 50 mol % of the second dopant;
the third layer comprises from zero to 50 mol % of the third dopant; or
any combination thereof.

9. The composition of claim 1, wherein the composition is a particle where the first layer is a particle core, the second layer is an inner layer at least partially coating the core, and the third layer is an outer layer at least partially coating the inner layer.

10. The composition of claim 1, wherein:
the first layer comprises NaYF$_4$ doped with 25 mol % Yb$^{3+}$ and 0.3 mol % Tm$^{3+}$, the second layer comprises NaYF$_4$ doped with 10 mol % Yb$^{3+}$ and 10 mol % Nd$^{3+}$, and the third layer comprises NaYF$_4$ without a dopant; or
the first layer and the third layer each comprise NaYF$_4$ doped with 20 mol % Yb$^{3+}$, and the second layer comprises NaYF$_4$ doped with 2 mol % Er$^{3+}$.

11. The composition of claim 1, further comprising a fourth layer in direct physical contact with the third layer, wherein the fourth layer comprises silica, an amphiphilic polymer, NaYF$_4$, CaF$_2$, ZrO$_2$, YVO$_4$, Y$_2$O$_2$S, GdOCl, GdOF, Y$_2$O$_3$, NaPrF$_4$, NaPmF$_4$, NaSmF$_4$, NaEuF$_4$, NaGdF$_4$, NaTbF$_4$, NaDyF$_4$, NaHoF$_4$, NaTmF$_4$, NaErF$_4$, NaCeF$_4$, NaNdF$_4$, NaLuF$_4$, NaYbF$_4$, or a combination thereof.

12. The composition of claim 11, wherein the composition further comprises:
a capping moiety;
a therapeutic agent;
an uptake enhancer;
a detection moiety;
a quenching moiety selected to absorb at least a portion of light emitted from the composition; or
a combination thereof.

13. The composition of claim 12, wherein:
the capping moiety comprise an azo derivative, heteroaryl azo derivative, diarylethene, imines derivative, acylhydrazone, hydrazone, hemithioindigo derivative, donor-acceptor Stenhouse adduct, or a combination thereof;
the therapeutic agent comprises a differentiation factor, chemotherapeutic agent, anti-inflammatory agent, antibiotic, antiviral, anesthetic agent, antipyretic, antiseptic, hormone, stimulant, depressant, statin, beta blocker, anticoagulant, anti-fungal, growth factor, vaccine, diagnostic composition, psychiatric medication, psychoactive compound, or a combination thereof;
the uptake enhancer is a peptide;
the detection moiety comprises an oligonucleotide, a polypeptide, antibody, antigen, or a combination thereof;
the quenching moiety comprises graphene; or
a combination thereof.

14. The composition of claim 12, wherein:
the capping moiety comprises

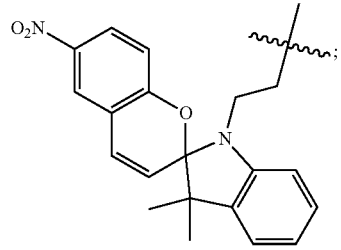 [SMILES: *CCN1c2ccccc2C(C)(C)C12C=Cc1cc([N+](=O)[O-])ccc1O2]

the therapeutic agent is retinoic acid;
the oligonucleotide is a dopamine aptamer;
the quenching moiety is graphene oxide;
the uptake enhancer is Arg-Gly-Asp; or
a combination thereof.

15. The composition of claim 12, wherein the quenching moiety is adsorbed onto the detection moiety.

16. The composition of claim 1, comprising:
a first layer comprising NaYF$_4$ doped with Yb$^{3+}$ and Tm$^{3+}$;
a second layer comprising NaYF$_4$ doped with Yb$^{3+}$ and Nd$^{3+}$;
a third layer comprising NaYF$_4$ without a dopant;
a fourth layer comprising mesoporous silica;
a spiropyran capping moiety conjugated to the fourth layer; and
an uptake enhancer conjugated to the fourth layer.

17. The composition of claim 1, comprising:
a first layer comprising NaYF$_4$ doped with Yb$^{3+}$;
a second layer comprising NaYF$_4$ doped with Er$^{3+}$;
a third layer comprising NaYF$_4$ doped with Yb$^{3+}$;
a fourth layer comprising non-porous silica;
a detection moiety conjugated to the fourth layer; and
a quenching agent adsorbed to the detection moiety.

18. A method, comprising exposing the composition according to claim 1 to incident light having a wavelength of from 600 nm to 1300 nm.

19. The method of claim 18, further comprising administering the composition to a subject prior to exposing the composition to the incident light, wherein:
the composition comprises a capping moiety and a therapeutic agent, and administering the composition comprises administering the composition to a subject in need of the therapeutic agent; or
the composition comprises a detection moiety, and administering the composition to a subject comprises administering the composition to a particular site on the subject's body that is suspected of containing a target recognizable by the detection moiety, and the method further comprises determining the presence or absence of the target based on the presence or absence of emitted light.

20. The method of claim 18, wherein the composition comprises a detection moiety, and the method comprises exposing a sample suspected of containing a target recognizable by the detection moiety to the composition prior to exposing the composition to the incident light, and determining the presence or absence of the target based on the presence or absence of emitted light.

\* \* \* \* \*

SEQUENCE LISTING

<160> NUMBER OF SEQ ID NOS: 5

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
gtctctgtgt gcgccagaga acactggggc agatatgggc cagcacagaa tgaggccc        58

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ccgcatcttc ttttgcgtcg        20

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
gcccaatacg accaaatccg t        21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ggtgtccgag taccagcagt        20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ttcgtacatc tcgccctctt        20